United States Patent
Collingwood et al.

(10) Patent No.: US 12,281,077 B2
(45) Date of Patent: Apr. 22, 2025

(54) SOLID FORMS OF N-TERT-BUTYL-4 [[2-(5-CHL-ORO-2-HYDROXY-PHENYL)ACETYL]AMINO] PYRIDINE-2-CARBOX-AMIDE

(71) Applicant: TMEM16A LIMITED, Welwyn Garden (GB)

(72) Inventors: Stephen Collingwood, Brighton (GB); Robert Melling, Abingdon (GB)

(73) Assignee: TMEM16A LIMITED (GB)

( * ) Notice: Subject to any disclaimer, the term of this patent is extended or adjusted under 35 U.S.C. 154(b) by 723 days.

(21) Appl. No.: 17/582,539

(22) Filed: Jan. 24, 2022

(65) Prior Publication Data

US 2022/0220074 A1 Jul. 14, 2022

Related U.S. Application Data

(63) Continuation of application No. PCT/GB2020/051779, filed on Jul. 24, 2020.

(30) Foreign Application Priority Data

Jul. 25, 2019 (GB) .................................. 1910664

(51) Int. Cl.
*C07D 213/81* (2006.01)

(52) U.S. Cl.
CPC ........ *C07D 213/81* (2013.01); *C07B 2200/13* (2013.01)

(58) Field of Classification Search
CPC .......................... C07D 213/81; C07B 2200/13
See application file for complete search history.

(56) References Cited

U.S. PATENT DOCUMENTS

2005/0176767 A1 8/2005 Kong et al.
2020/0383988 A1* 12/2020 Collingwood ....... C07D 405/12

FOREIGN PATENT DOCUMENTS

| CL | 2020001945 A1 | 1/2021 |
| WO | 2005042524 A1 | 5/2005 |
| WO | 2008002671 A2 | 1/2008 |
| WO | WO-2016042114 A1 | 3/2016 |
| WO | 2018195127 A1 | 10/2018 |
| WO | 2019145726 A1 | 8/2019 |

OTHER PUBLICATIONS

International Search Report and Written Opinion for Application No. PCT/GB2020/051779, mailed on Oct. 9, 2020, 10 pages.
Namkung et al. (2011) "TMEM16A Inhibitors Reveal TMEM16A as a Minor Component of Calcium-activated Chloride Channel Conductance in Airway and Intestinal Epithelial Cells", The Journal Of Biological Chemistry, 286 (3):2365-2374.
Bernstein, Joel, et al., Bioavailability, Polymorphism of Molecular Crystals, Bioavailability, 2007, pp. 324-330, chapter 7.3.2, Moscow: Nauka.
Bryn et al., Pharmaceutical Solids: A strategic Approach to Regulatory Considerations, Pharmaceutical Research, 1995, vol. 12, No. 7, pp. 945-954.
Caira et al., Crystalline Polymorphism of Organic Compounds, Topics in Current Chemistry, 1998, vol. 198, pp. 163-208.
Guo et al., TMEM16A: A type of Calcium-activated Chloride Channel, Chinese Journal of Biochemistry and Molecular Biology, Dec. 2017, vol. 33, No. 12, pp. 1187-1194.
Kunzelmann et al., TMEM16A in Cystic Fibrosis: Activating or Inhibiting?, Frontiers in Phrmacology, Jan. 29, 2019, vol. 10, Article 3, 18 pages.
Liu et al., Research progress on the role of calcium-activated chloride channel protein A in tumor formation, Med J Qilu, Feb. 28, 2017, vol. 32, No. 1, pp. 114-119. English abstract.
Namkung et al., Small-molecule activators of TMEM16A, a calcium-activated chloride channel, stimulate epithelial chloride secretion and intestinal contraction, The FASEB Journal Research Communication, Nov. 2011, vol. 25, pp. 4048-4062.
Pinto et al., Thermoanalytical studies of carbamazepine: hydration/dehydration, thermal decomposition, and solid phase transitions, Brazilian Journal of Pharmaceutical Sciences, Oct./Dec. 2014, vol. 50, No. 4, pp. 877-884.
Reichardt, C., Solvents and Solvent effects in Organic Chemistry, Mir Publishing House, 1991, pp. 611-614, section A5. (Translation is not available.)
Rodriguez-Spong et al., General principles of pharmaceutical solid polymorphism: A supramolecular perspective, Advance Drug Delivery Reviews, Feb. 23, 2004, vol. 56, No. 3, pp. 241-274, Abstract.
Yu, Lian, Amorphous pharmaceutical solids: preparation, characterization and stabilization, Advanced Drug Delivery Reviews, 2001, vol. 48, pp. 27-42.

\* cited by examiner

*Primary Examiner* — Timothy R Rozof
(74) *Attorney, Agent, or Firm* — Mintz, Levin, Cohn, Ferris, Glovsky & Popeo, P.C.

(57) ABSTRACT

The invention relates to novel forms of N-tert-Butyl-4-[[2-(5-chloro-2-hydroxy-phenyl)acetyl]amino]pyridine-2-carboxamide (Compound 1). In particular, the invention relates to the Form A and Form B crystalline polymorphs and the amorphous form.

18 Claims, 42 Drawing Sheets

SOLID FORMS OF N-TERT-BUTYL-4[[2-(5-CHLORO-2-HYDROXY-PHENYL)ACETYL]AMINO]PYRIDINE-2-CARBOXAMIDE

This application is a continuation of the International Application No. PCT/GB2020/051779, filed Jul. 24, 2020, which claims the benefit of GB Application No. 1910664.0, filed Jul. 25, 2019, which are incorporated hereby by reference in their entirety for all purposes.

FIELD OF THE INVENTION

The present invention relates to novel forms, including crystalline forms, of a compound which has activity as a positive modulator of the calcium-activated chloride channel (CaCC), TMEM16A. The invention also relates to methods of preparing the novel forms and pharmaceutical compositions containing them as well as to their use in treating diseases and conditions in which TMEM16A plays a role, particularly respiratory diseases and conditions.

BACKGROUND OF THE INVENTION

Humans can inhale up to 12,000 L of air each day and with it comes the potential for airborne pathogens (such as bacteria, viruses and fungal spores) to enter the airways. To protect against these airborne pathogens, the lung has evolved innate defence mechanisms to minimise the potential for infection and colonisation of the airways. One such mechanism is the mucus clearance system, whereby secreted mucus is propelled up and out of the airways by the coordinated beating of cilia together with cough clearance. This ongoing 'cleansing' of the lung constantly removes inhaled particles and microbes thereby reducing the risk of infection.

In recent years it has become clear that the hydration of the mucus gel is critical to enable mucus clearance (Boucher 2007; Matsui et al, 1998). In a normal, healthy airway, the mucus gel is typically 97% water and 3% w/v solids under which conditions the mucus is cleared by mucociliary action. The hydration of the airway mucosa is regulated by the coordinated activity of a number of ion channels and transporters. The balance of anion ($Cl^-/HCO_3^-$) secretion mediated via the Cystic Fibrosis Transmembrane Conductance Regulator (CFTR) and the Calcium Activated Chloride Conductance (CaCC; TMEM16A) and $Na^+$ absorption through the epithelial $Na^+$ channel (ENaC) determine the hydration status of the airway mucosa. As ions are transported across the epithelium, water is osmotically obliged to follow and thus fluid is either secreted or absorbed.

In respiratory diseases such as chronic bronchitis and cystic fibrosis, the % solids of the mucus gel is increased as the hydration is reduced and mucus clearance is reduced (Boucher, 2007). In cystic fibrosis, where loss of function mutations in CFTR attenuates the ability of the airway to secrete fluid, the % solids can be increased to 15% which is believed to contribute towards the plugging of small airways and failure of mucus clearance. Strategies to increase the hydration of the airway mucus include either the stimulation of anion secretion and thereby fluid secretion or the inhibition of $Na^+$ absorption. To this end, stimulating the activity of TMEM16A channels will increase anion secretion and therefore increase fluid accumulation in the airway mucosa, hydrate mucus and enhance mucus clearance mechanisms.

TMEM16A, also referred to as Anoctamin-1 (Ano1), is the molecular identity of calcium-activated chloride channels (Caputo et al, 2008; Yang et al, 2008). TMEM16A channels open in response to elevation of intracellular calcium levels and allow the bidirectional flux of chloride, bicarbonate and other anions across the cell membrane. Functionally TMEM16A channels have been proposed to modulate transepithelial ion transport, gastrointestinal peristalsis, nociception and cell migration/proliferation (Pedemonte & Galietta, 2014).

TMEM16A channels are expressed by the epithelial cells of different organs including the lungs, liver, kidney, pancreas and salivary glands. In the airway epithelium TMEM16A is expressed at high levels in mucus producing goblet cells, ciliated cells and in submucosal glands. Physiologically TMEM16A is activated by stimuli which mobilise intracellular calcium, particularly purinergic agonists (ATP, UTP), which are released by the respiratory epithelium in response to cyclical shear stress caused by breathing and other mechanical stimuli such as cough. In addition to increasing anion secretion leading to enhanced hydration of the airways, activation of TMEM16A plays an important role in bicarbonate secretion. Bicarbonate secretion is reported to be an important regulator of mucus properties and in controlling airway lumen pH and hence the activity of native antimicrobials such as defensins (Pezzulo et al, 2012).

Indirect modulation of TMEM16A, via elevation of intracellular calcium, has been clinically explored eg. denufosol (Kunzelmann & Mall, 2003). Although encouraging initial results were observed in small patient cohorts this approach did not deliver clinical benefit in larger patient cohorts (Accurso et al 2011; Kellerman et al 2008). This lack of clinical effect was ascribed to only a transient elevation in anion secretion, the result of a short half-life of denufosol on the surface of the epithelium and receptor/pathway desensitisation, and unwanted effects of elevating intracellular calcium such as increased release of mucus from goblet cells (Moss, 2013). Compounds which act directly upon TMEM16A to enhance channel opening at low levels of calcium elevation are expected to durably enhance anion secretion and mucociliary clearance in patients and improve innate defence. As TMEM16A activity is independent of CFTR function, TMEM16A positive modulators have the potential to deliver clinical benefit to all CF patients and non-CF respiratory diseases characterised by mucus congestion including chronic bronchitis and severe asthma.

TMEM16A modulation has been implicated as a therapy for dry mouth (xerostomia), resultant from salivary gland dysfunction in Sjorgen's syndrome and radiation therapy, dry eye, cholestasis and gastrointestinal motility disorders.

The present inventors have developed novel compounds, and novel forms of these compounds, which are positive modulators of TMEM16A and which are therefore of use in the treatment of diseases and conditions in which TMEM16A plays a role, particularly respiratory diseases and conditions. These compounds were described for the first time in our earlier application WO2019/145726, the contents of which are hereby incorporated by reference in their entirety. In particular, WO2019/145726 discloses N-tert-Butyl-4-[[2-(5-chloro-2-hydroxy-phenyl)acetyl]amino]pyridine-2-carboxamide (Compound 1), which has the following structural formula:

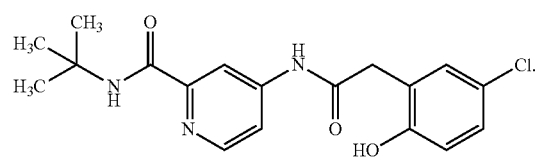 [SMILES: CC(C)(C)NC(=O)c1cc(NC(=O)Cc2cc(Cl)ccc2O)ccn1]

SUMMARY OF THE INVENTION

The inventors have now developed novel forms of Compound 1.

In a first aspect of the invention there is provided Compound 1 in the form of its Form A anhydrous solid crystalline polymorph.

In a second aspect of the invention there is provided Compound 1 in the form of its Form B hydrate solid crystalline polymorph, in particular the Form B(I) hydrate solid crystalline pseudopolymorph or the Form B(II) hydrate solid crystalline pseudopolymorph.

In a third aspect of the invention there is provided anhydrous solid amorphous Compound 1.

BRIEF DESCRIPTION OF THE FIGURES

FIG. 1b is a zoomed in view of FIG. 1a.

FIG. 3a is a DVS isotherm plot, where ■ represents desorption and ♦ represents sorption; and FIG. 3b is a change in mass plot.

DETAILED DESCRIPTION OF THE INVENTION

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All literature and patent documents referred to herein are incorporated by reference to the fullest extent possible.

Where the specification refers to a volume of solvent per unit mass of Compound 1, this refers to mg of Compound 1 and μL of solvent such that 50 mg of Compound 1 in 20 volumes of solvent is a sample of 1 mL volume; 30 mg of Compound 1 in 60 volumes of solvent is a sample of 1.8 mL volume and 30 mg of Compound 1 in 70 volumes of solvent is sample 2.1 mL volume.

In the present specification, references to "pharmaceutical use" refer to use for administration to a human or an animal, in particular a human or a mammal, for example a domesticated or livestock mammal, for the treatment or prophylaxis of a disease or medical condition. The term "pharmaceutical composition" refers to a composition which is suitable for pharmaceutical use and "pharmaceutically acceptable" refers to an agent which is suitable for use in a pharmaceutical composition. Other similar terms should be construed accordingly.

Compound 1 disclosed herein is N-tert-Butyl-4-[[2-(5-chloro-2-hydroxy-phenyl)acetyl]amino]pyridine-2-carboxamide, which has the structure shown above. This compound is exemplified in our earlier application WO2019/145726 and the method exemplified in that document results in the production of Compound 1 as a mixture of at least two crystalline forms (see Example 1).

The present inventors have found a number of different crystalline and non-crystalline forms of Compound 1, namely forms A, B, C, D, E, F, G and H and an amorphous form. Polymorphic Forms A and B are particularly useful as they are thermodynamically stable.

Figure 1A:
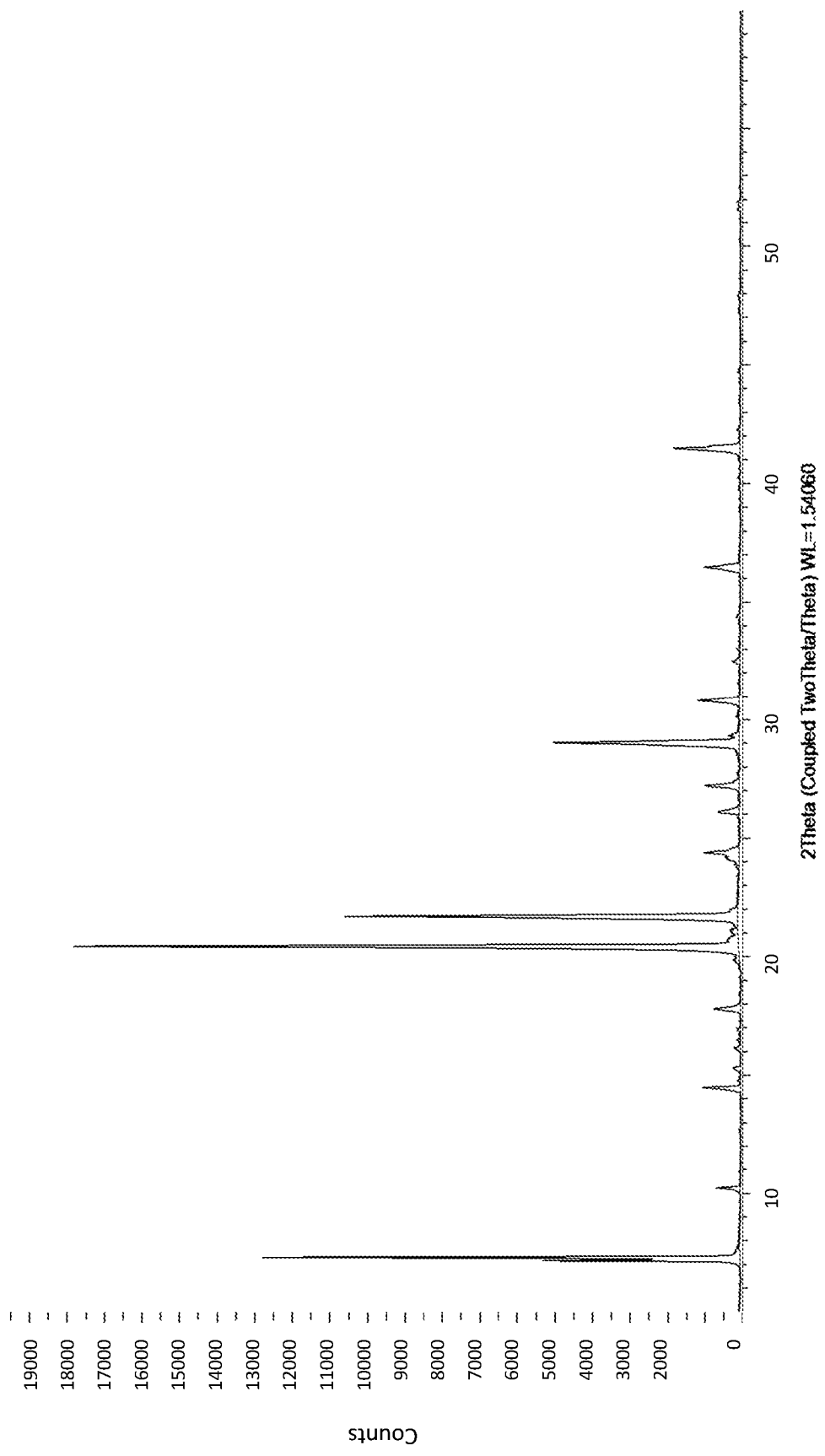
FIG. 1a is an XRPD diffractogram of solid crystalline polymorphic form A of Compound 1 in the range of 5 to 60 2-theta, step size 0.02 s (reflection mode, offset 500 counts).
Figure 1B:
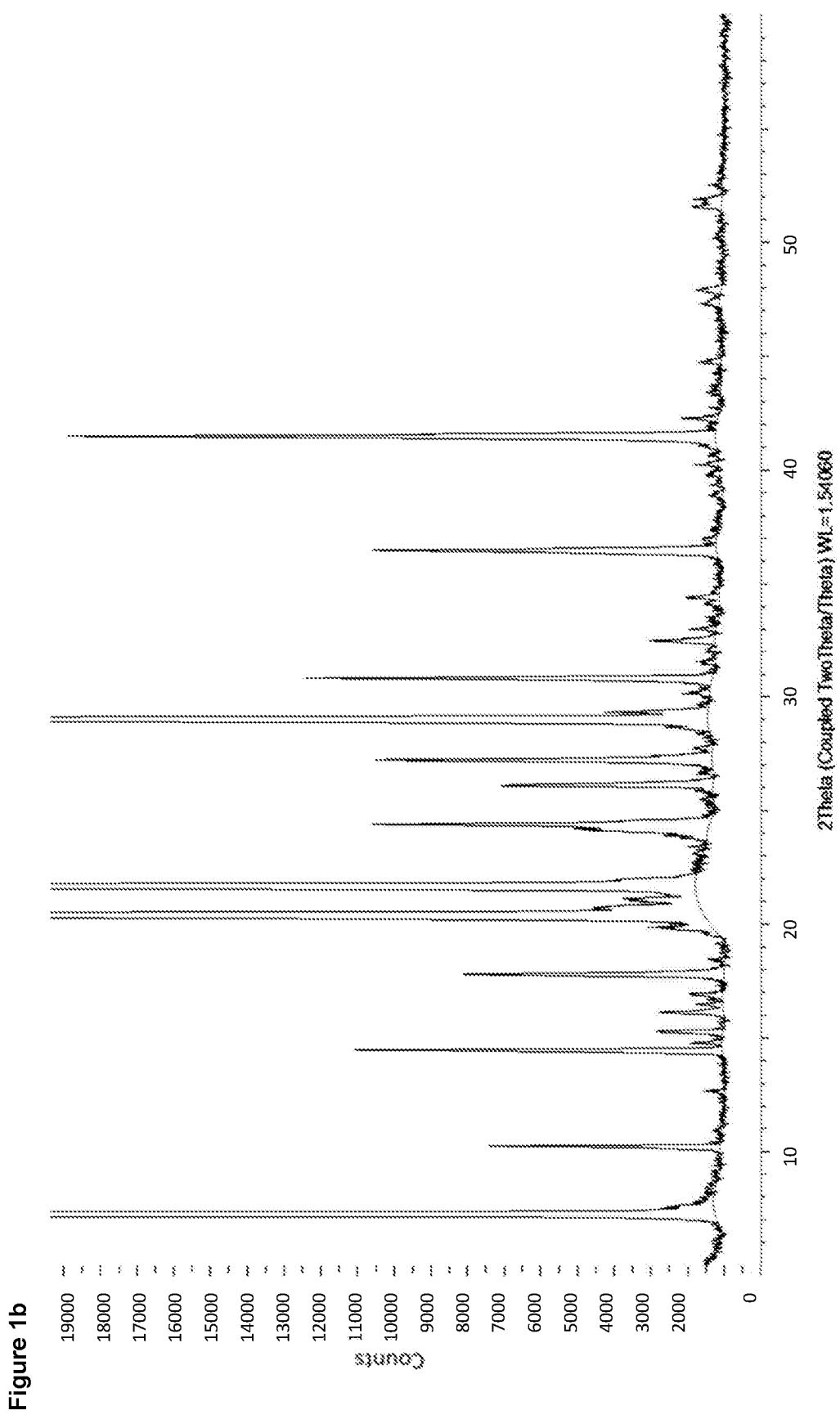

Therefore, in one aspect of the invention, there is provided Compound 1 in the form of its Form A anhydrous solid crystalline polymorph (the Form A polymorph), for example as characterised by an XRPD diffractogram substantially as shown in FIGS. 1a and 1b.

A peak at position 7.25 (±0.2 degrees, 2-theta value) in the XRPD diffractogram of the Form A polymorph of Compound 1 is particularly useful for distinguishing it from the Form B hydrate solid crystalline polymorph of Compound 1.

Suitably, the major peak at 7.25 (±0.2 degrees, 2-theta value) and at least three further peaks (for example three, four, five, six, seven, eight or all nine) selected from the peaks at positions 14.44, 20.42, 21.68, 24.38, 27.21, 29.01, 30.82, 36.46 and 41.49 (±0.2 degrees, 2-theta values) are observable in the XRPD diffractogram of the Form A polymorph of Compound 1.

Of these, the peaks at positions 21.68 and 29.01 (±0.2 degrees, 2-theta values) are also especially characteristic of the Form A crystalline polymorph and therefore it is typical that at least one and preferably both of these are observable.

Suitably, a cluster of peaks at 24.09, 24.22 and 24.38 (±0.2 degrees, 2-theta values) is also observable in the XRPD diffractogram as this is also characteristic of the From A crystalline polymorph.

More usually, the major peak at 7.25 (±0.2 degrees, 2-theta value) and at least three further peaks (for example three, four, five, six, seven, eight, nine, ten, eleven, twelve, thirteen or all fourteen) selected from the peaks at positions 10.20, 14.44, 17.79, 20.42, 20.69, 21.68, 24.22, 24.38, 26.13, 27.21, 29.01, 30.82, 36.46 and 41.49 (±0.2 degrees, 2-theta values) are observable in the XRPD diffractogram of the Form A polymorph of Compound 1.

Again, it is typical that at least one and preferably both of the peaks at positions 21.68 and 29.01 (±0.2 degrees, 2-theta values) and suitably also the cluster of peaks at 24.09, 24.22 and 24.38 (±0.2 degrees, 2-theta values) are observable.

In some cases, the major peak at 7.25 (±0.2 degrees, 2-theta value) and at least three further peaks (for example three, four, five, six, seven, eight, nine, ten, eleven, twelve, thirteen, fourteen, fifteen, sixteen, seventeen, eighteen or all nineteen) selected from the peaks at positions 10.20, 14.44, 16.13, 17.79, 20.42, 20.69, 21.07, 21.68, 24.09, 24.22, 24.38, 26.13, 27.21, 29.01, 29.30, 30.82, 32.50, 36.46 and 41.49 (±0.2 degrees, 2-theta values) are observable in the XRPD diffractogram of the Form A polymorph of Compound 1.

Again, it is typical that at least one and preferably both of the peaks at positions 21.68 and 29.01 (±0.2 degrees, 2-theta values) and suitably also the cluster of peaks at 24.09, 24.22 and 24.38 (±0.2 degrees, 2-theta values) are observable.

The XRPD diffractogram of the Form A polymorph has peaks at 7.25, 10.20, 12.64, 14.44, 14.81, 15.27, 16.13, 16.47, 16.90, 17.79, 19.86, 20.42, 20.69, 21.07, 21.68, 24.09, 24.22, 24.38, 25.46, 26.13, 26.69, 27.21, 27.71, 29.01, 29.30, 30.16, 30.82, 31.55, 32.50, 33.02, 34.14, 34.42, 36.46, 36.96, 38.92, 39.82, 40.26, 41.49, 42.28, 44.76, 47.34, 47.92, 51.61 and 51.84 (±0.2 degrees, 2-theta values) and suitably, the peak at 7.25 and at least three, (for example three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two or all forty-three) of the remaining peaks are observable in the resulting XRPD diffractogram.

Again, it is typical that at least one and preferably both of the peaks at positions 21.68 and 29.01 (±0.2 degrees, 2-theta values) and suitably also the cluster of peaks at 24.09, 24.22 and 24.3801 (±0.2 degrees, 2-theta values) are observable.

The 2-theta values of the XRPD peaks for Form A and their intensities are as shown in Table 1 below.

TABLE 1

| 2-theta values for Form A | | | | |
|---|---|---|---|---|
| Angle | d value | Net intensity | Gross intensity | Rel. intensity |
| 7.251562 | 12.18066 | 5239.937 | 5315.917 | 0.3025107 |
| 10.1966 | 8.668229 | 499.0941 | 561.1417 | 0.02881358 |
| 12.63753 | 6.998919 | 26.0892 | 73.99069 | 0.001506175 |
| 14.44414 | 6.127335 | 767.3766 | 823.38 | 0.044302 |
| 14.8052 | 5.978704 | 72.98463 | 130.3546 | 0.004213531 |
| 15.2693 | 5.798016 | 163.221 | 217.4684 | 0.009423036 |
| 16.12721 | 5.491459 | 174.3389 | 226.2095 | 0.01006489 |
| 16.46675 | 5.378986 | 65.45334 | 120.451 | 0.003778736 |
| 16.90075 | 5.241822 | 71.15353 | 125.6468 | 0.004107819 |
| 17.7908 | 4.981534 | 660.2592 | 711.8703 | 0.03811793 |
| 19.85568 | 4.467897 | 169.8164 | 251.9603 | 0.0098038 |
| 20.42344 | 4.344954 | 17321.49 | 17427.89 | 1 |
| 20.68812 | 4.28996 | 291.5545 | 406.3246 | 0.01683195 |
| 21.07078 | 4.212908 | 183.1013 | 306.6645 | 0.01057076 |
| 21.68274 | 4.095368 | 9554.02 | 9683.525 | 0.5515704 |
| 24.091 | 3.691149 | 274.1138 | 370.372 | 0.01582507 |
| 24.2245 | 3.671108 | 304.4359 | 398.6893 | 0.01757562 |
| 24.3786 | 3.648251 | 903.7159 | 995.0638 | 0.05217311 |
| 25.45634 | 3.496186 | 24.17885 | 103.4759 | 0.001395887 |
| 26.12567 | 3.408113 | 550.0715 | 631.1149 | 0.0317566 |
| 26.68727 | 3.337654 | 37.45216 | 116.6506 | 0.002162179 |
| 27.20708 | 3.275055 | 846.9998 | 931.5104 | 0.04889879 |
| 27.7149 | 3.216189 | 42.49388 | 125.2368 | 0.002453247 |
| 29.0088 | 3.07561 | 4687.926 | 4784.333 | 0.2706422 |
| 29.29712 | 3.045996 | 219.7664 | 315.2301 | 0.0126875 |
| 30.16241 | 2.960554 | 33.78499 | 123.798 | 0.001950467 |
| 30.81519 | 2.89931 | 1103.351 | 1187.295 | 0.0636984 |
| 31.55083 | 2.833367 | 40.47586 | 114.1987 | 0.002336743 |
| 32.50196 | 2.75259 | 176.9755 | 254.0596 | 0.01021711 |
| 33.02495 | 2.710186 | 66.46635 | 139.8932 | 0.003837219 |
| 34.13988 | 2.624184 | 38.61419 | 102.3695 | 0.002229265 |
| 34.42226 | 2.603301 | 81.95594 | 147.2012 | 0.004731461 |
| 36.46003 | 2.46234 | 891.7058 | 963.7139 | 0.05147975 |
| 36.95838 | 2.430273 | 35.77224 | 108.3649 | 0.002065194 |
| 38.91542 | 2.312442 | 20.60205 | 75.85722 | 0.001189392 |
| 39.81746 | 2.26211 | 21.9453 | 86.78886 | 0.001266941 |
| 40.26387 | 2.238053 | 27.66707 | 94.44741 | 0.001597269 |
| 41.48539 | 2.174933 | 1731.975 | 1807.205 | 0.09998996 |
| 42.27512 | 2.136112 | 97.53069 | 166.3153 | 0.005630618 |
| 44.76455 | 2.02293 | 44.91547 | 104.2081 | 0.002593049 |
| 47.33979 | 1.918715 | 33.17021 | 97 | 0.001914975 |
| 47.9173 | 1.89693 | 67.51047 | 126.3937 | 0.003897498 |
| 51.60581 | 1.769679 | 64.77835 | 123.1883 | 0.003739768 |
| 51.84337 | 1.762127 | 51.15655 | 108.2122 | 0.002953358 |

The Form A polymorph may be micronised and the inventors have demonstrated that the crystal structure is maintained on micronisation. Micronisation suitably results in particles with D50 of 5 μm, more suitably 3 μm, and D90 of ≤10 μm, more suitably ≤5 μm. For example, D50 may be about 1-5 μm, more suitably about 1-3 μm;

D50 represents the median particle diameter on a volume basis; such that 50% of the total volume of particles have a particle diameter less than or equal to D50. Similarly, D90 is defined such that 90% of the volume of particles have a particle diameter less than or equal to D90.

A number of suitable methods are available for the measurement of D50 and D90, for example laser diffraction methods. These methods are well known and are familiar to those of skill in the art.

Some of the peaks of the XRPD diffractogram may either increase or decrease in intensity on micronisation. In particular, the peaks at 14.44 and 29.01 (±0.2 degrees, 2-theta values) may decrease in intensity, while the peaks at 17.79 and 27.21 (±0.2 degrees, 2-theta value) may increase in intensity. This is thought to arise from orientation effects as well as changes in texture and crystallite size and distribution.

XRPD analysis may be carried out using a Bruker D2 Phaser powder diffractometer equipped with a LynxEye detector.

Suitably, the Form A polymorph is substantially free from other forms of Compound 1, such that, for example, in a sample of Compound 1, at least 97%, 97.5%, 98%, 98.5%, 99%, 99.5%, 99.6% 99.7%, 99.8% or 99.9% by weight of Compound 1 is present as the Form A polymorph.

The inventors have found that the Form A polymorph may be obtained, for example by crystallising from any one of a number of solvents including acetone, butanol, ethanol, ethyl formate, isopropyl acetate, methyl acetate, nitromethane, 2-propanol, propionitrile and acetonitrile. A number of crystallisation conditions may be used.

Crystallisation may be achieved by a heat-up cool-down method comprising the steps of:
i. preparing a saturated solution of Compound 1 in a solvent at a temperature of about 50 to 70° C.;
ii. cooling the solution to a temperature of about 5 to 20° C.;
iii. allowing the cooled solution to stand until crystals of Compound 1 form; and
iv. isolating the crystallised product;
wherein the solvent is selected from acetone, butanol, ethanol, ethyl formate, isopropyl acetate, methyl acetate, nitromethane, 2-propanol, propionitrile and acetonitrile.

More suitably, the solvent is acetonitrile, ethanol, ethyl acetate, methyl acetate, butanol, 2-propanol or isopropyl acetate.

Ethanol, butanol and 2-propanol are suitably used in an amount of 4 to 7, more suitably about 4 to 6 volumes per unit mass of Compound 1.

Methyl acetate, ethyl acetate and isopropyl acetate are suitably used in an amount of 10 to 20, volumes per unit mass of Compound 1. For example, methyl acetate may be used in an amount of about 10 to 12 volumes, especially about 10.5 to 11.5 volumes, for example 11 volumes per unit mass of Compound 1. Ethyl acetate may be used in an amount of about 19 to 21 volumes, especially about 19.5 to 20.5 volumes, for example about 20 volumes per unit mass of Compound 1 and isopropyl acetate may be used in an amount of about 15 to 17 volumes, especially about 15.6 to 16.5 volumes, for example about 16 volumes per unit mass of Compound 1.

Most suitably, the crystallisation solvent is ethanol, ethyl acetate or methyl acetate, suitably at the concentrations set out above.

Crystallisation is suitably not carried out in anisole, butylmethyl ether, cumene, chlorobenzene, ethyl acetate, methylethyl ketone, propionitrile, toluene, trifluorotoluene tetrahydrofuran, dichloromethane or dichloromethane/heptane as these lead to the production of other forms of Compound 1.

Crystallisation is also suitably not carried out in an aqueous solvent as this leads to the production of the Form B hydrate solid crystalline polymorph of Compound 1.

Suitably, the Compound 1 used to prepare the saturated solution in step (i) is amorphous Compound 1.

Alternatively, crystallisation may be via a diffusion method from a binary solvent in a method comprising the steps of:

i. preparing a saturated solution of Compound 1 is prepared in a less volatile solvent; and
ii. transferring the saturated solution to a first vessel;
iii. placing the first vessel inside a second vessel which is larger than the first vessel and which contains a second solvent, which is more volatile than the first solvent;
iv. covering the vessel and allowing to stand for 1 to 10 days at a temperature of 15 to 25° C., preferably 18 to 23° C. such that the second solvent diffuses into the first vessel and crystallisation of Compound 1 takes place in the first vessel; and
v. isolating the crystallised product from the first vessel;
wherein the first solvent is ethanol and the second solvent is pentane.

Alternatively, the Form A polymorph may be prepared by a cold crystallisation method comprising heating amorphous Compound 1 to a temperature of greater than 97° C. and allowing to cool.

A particularly suitable crystallisation method comprises:
i. preparing a mixture of Compound 1 in ethyl acetate;
ii. Heating the mixture to 55 to 70° C., especially 55 to 65° C. and more especially about 60° C. and stirring until a solution of Compound 1 in ethyl acetate is obtained;
iii. Allowing the solution to cool to 40 to 50° C., especially about 45 to 49° C. and more especially about 47° C.;
iv Concentrating the solution;
v. cooling at a constant rate over 1 to 4 hours, especially about 2 to 3 hours, to about 15 to 30° C., especially about 20 to 25° C. and more especially about 23° C. and leaving to stand for 4 to 6 hours, for example 5 hours;
vi. adding n-heptane over a period of 0.75 to 2.5 hours, for example 1 to 2 hours at a temperature of 15 to 30° C., especially about 20 to 25° C. and more especially about 23° C. and leave to stand for 20 to 80 minutes, for example about 30 to 60 minutes;
vii. cooling the mixture at a constant rate over 1 to 5 hours, especially about 2 to 4 hours and typically about 3 hours, to a temperature of −5 to 10° C., especially about 0 to 5° C. and more especially about 2.5° C. and leaving to stand to obtain solid crystalline Form A polymorph of Compound 1;
viii. isolating and drying the solid crystalline Form A polymorph of Compound 1.

In this method, in step (i), the volume of ethyl acetate per unit mass of Compound 1 is suitably about 15 to 25, more suitably about 20 volumes of ethyl acetate per unit mass of Compound 1.

Suitably, in step (ii), stirring takes place for at least 10 minutes. The solution of Compound 1 is a hazy solution and after step (iii), the solution may be clarified by filtration, for example through a 1 μm filter. The method suitably contains an additional step of rinsing with ethyl acetate. Suitably, the rinsing volume is about 10 to 20%, for example about 15% by volume of the original amount of ethyl acetate used in step (i).

In step (iv), the solution will suitably be concentrated to about 40 to 60%, for example about 50%, of the volume of ethyl acetate used in step (i). Concentration may be achieved using vacuum distillation and is suitably carried out at temperature of about 40 to 50° C., typically about 45° C.

Figure 2:
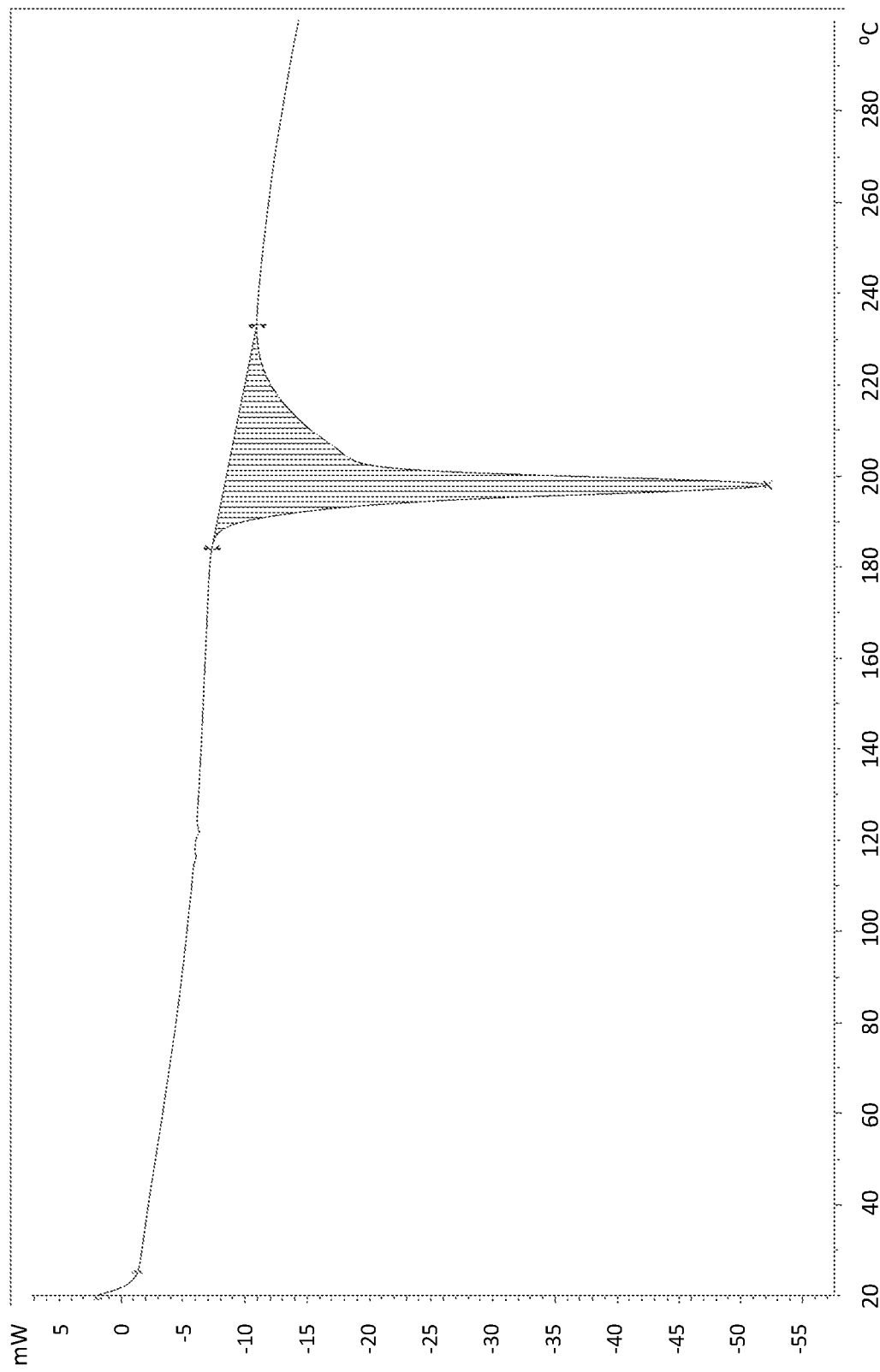
FIG. 2 is a DSC thermogram of polymorphic Form A of Compound 1 acquired at a ramp rate of +10° C./minute with an input weight of 12.7 mg of Compound 1, Form A and showing: integral −378.65 mW° C., a melt onset of 192.94° C. and endset of 202.19° C.

Polymorphic Form A is the most thermodynamically stable form of Compound 1. It has a relatively high melting point, where melt onset occurs at about 193° C. as can be seen from the DSC thermogram of FIG. 2.

Figure 3A:
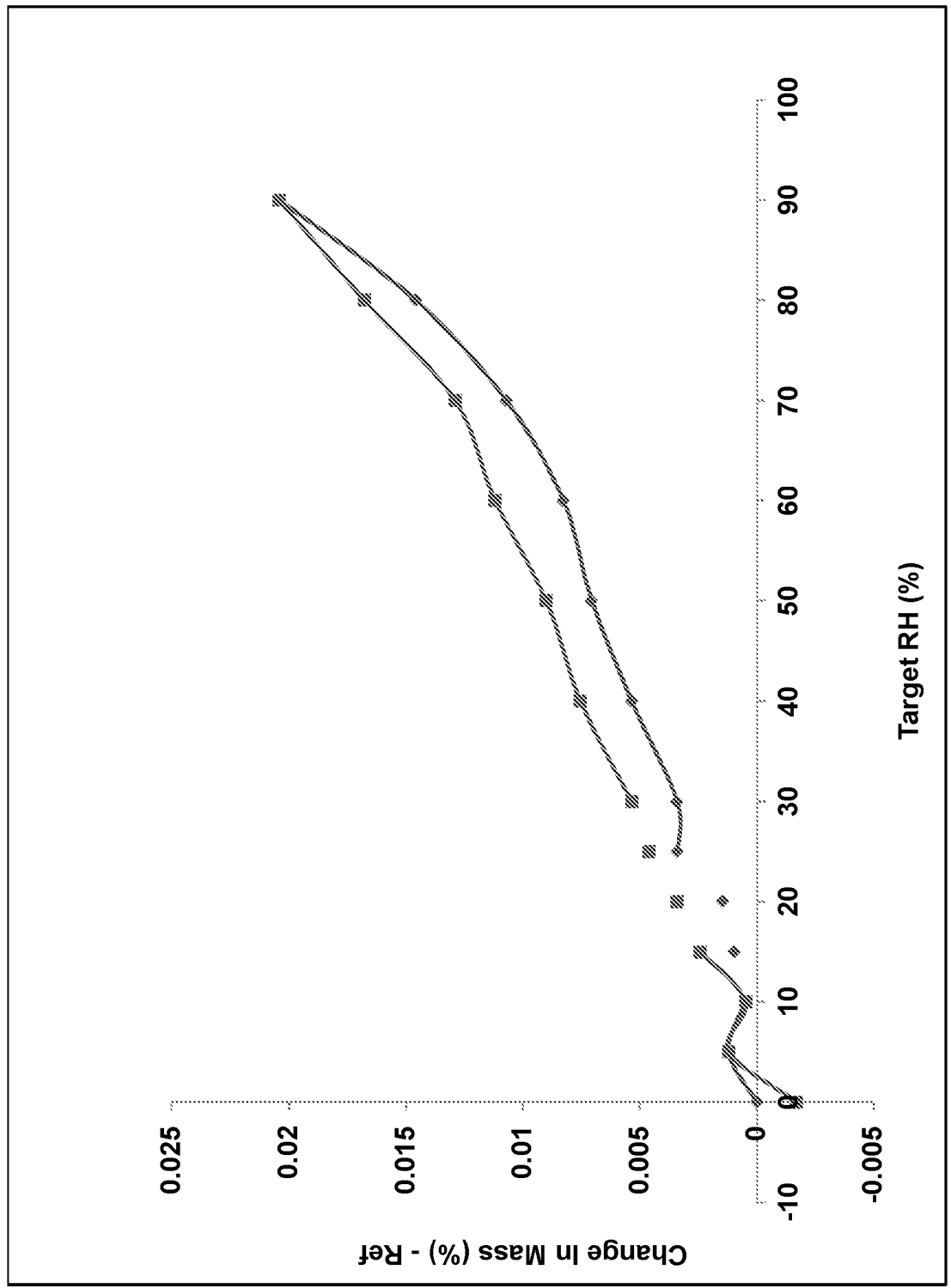
FIGS. 3a and 3b are dynamic vapour sorption (DVS) plots for polymorphic Form A of Compound 1.
Figure 3B:
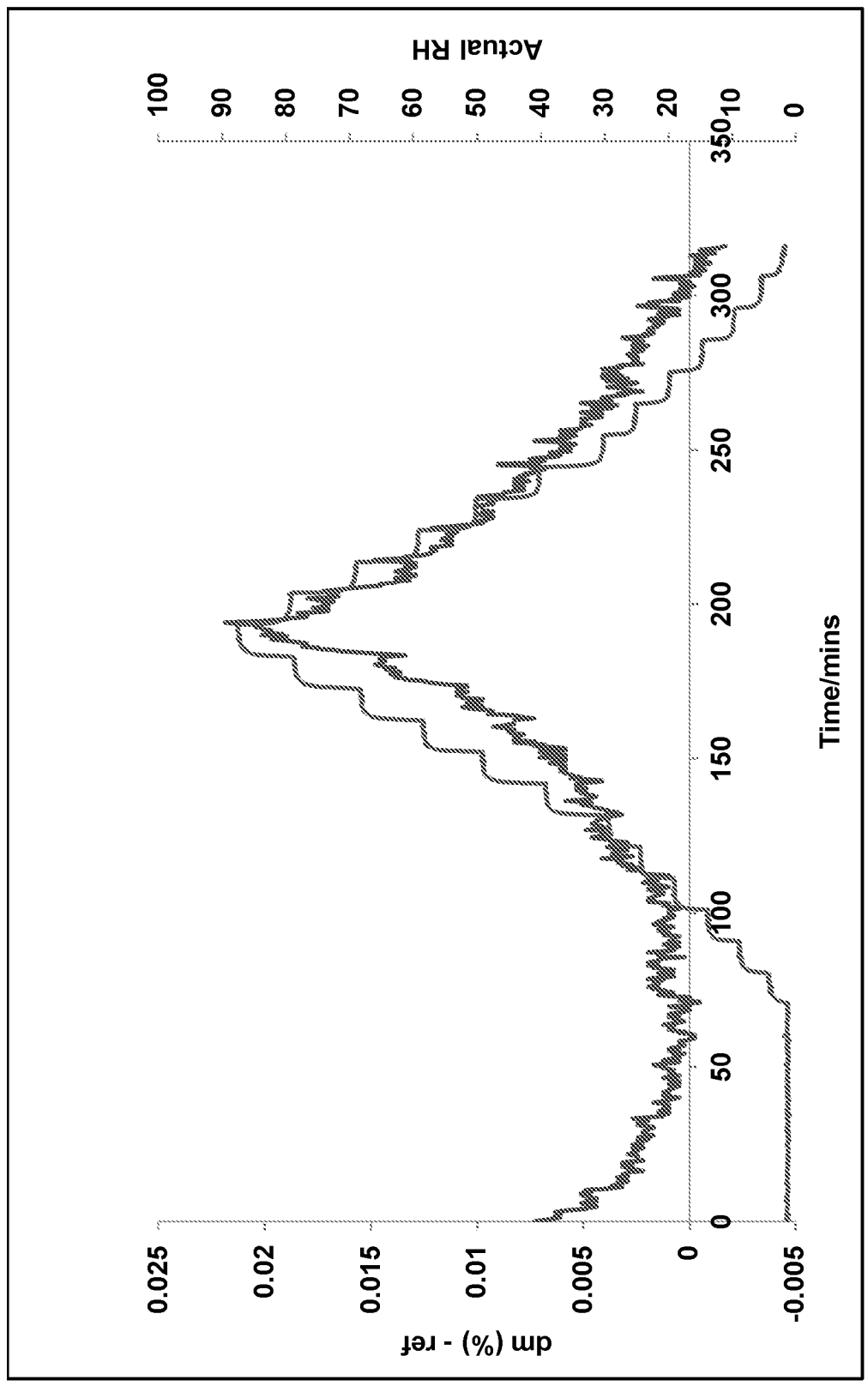

Polymorphic Form A has low moisture affinity and is not hygroscopic as shown by the DVS plot of FIG. 3. From FIG.

3, it can be seen that the change in mass (representing the uptake of water) at 90% relative humidity (RH) is only 0.02%. Furthermore, when the XRPD analysis was repeated after the DVS test, the results were the same as for the sample before DVS analysis, showing that no hydrate was formed. This shows that Form A is stable to moisture and, indeed, the inventors have shown that in order to produce the hydrate Form B, water has to ingress into the crystal lattice. This is why, as discussed in greater detail below, the hydrate form B is formed when Compound 1 is recrystallised from an aqueous solvent.

Surprisingly, however, although Form A is the most thermodynamically stable crystalline form at low water activity and is kinetically stable to moisture by DVS, it has been found that it is not thermodynamically stable under conditions of elevated water activity, for example when suspended in an aqueous solvent. Under these conditions, it is converted to the Form B hydrate crystalline polymorph over a time period of a few days.

In an aqueous suspension of the Form A crystalline polymorph, no Form B can be detected at the 24 hour time point. However, after 8 days, substantially all of the Compound 1 was present as the Form B hydrate crystalline form.

Figure 4:
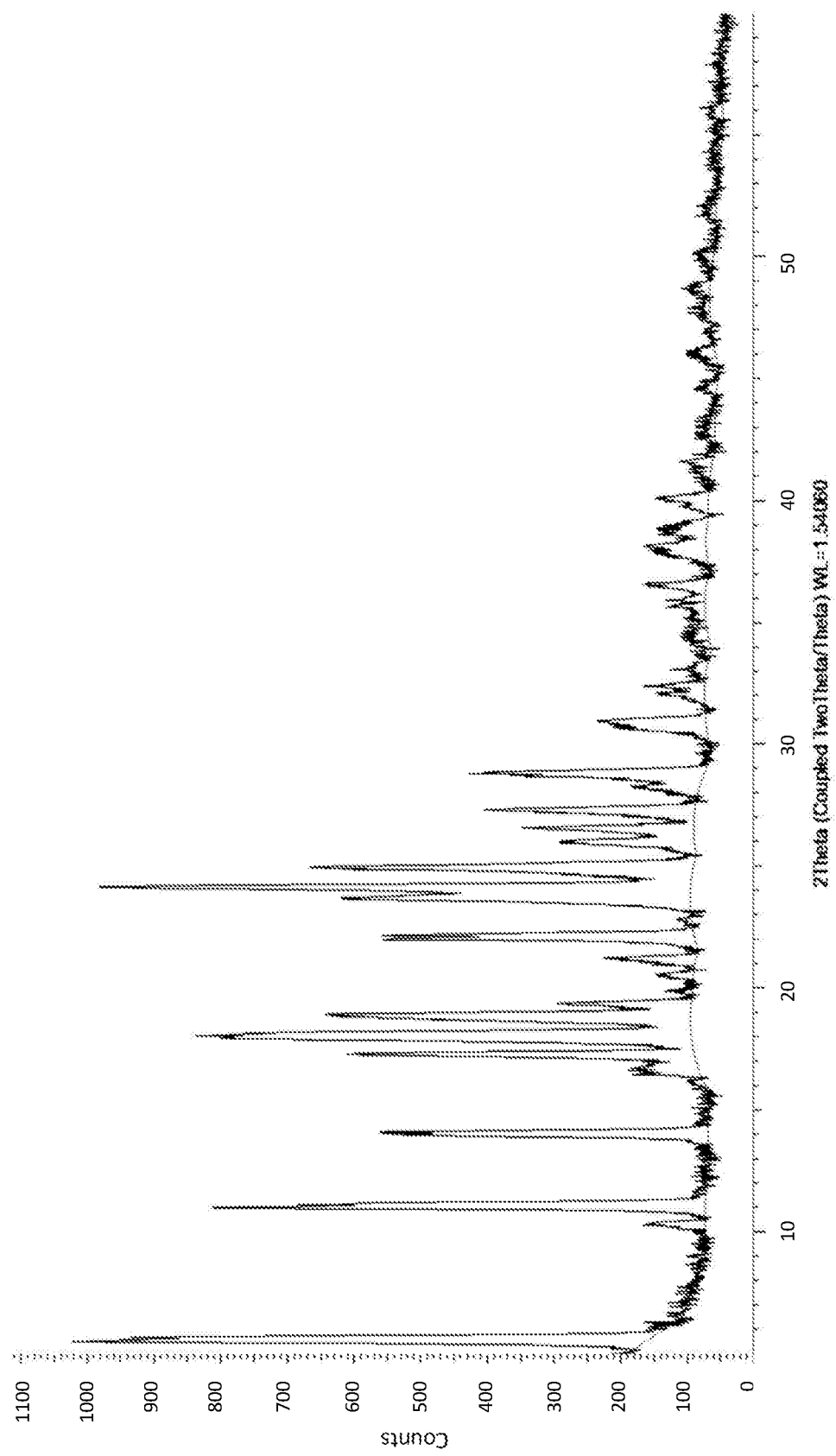
FIG. 4 is an XRPD diffractogram of solid crystalline polymorphic form B of Compound 1 in the range of 5 to 60 2-theta, step size 0.02 s (reflection mode, offset 500 counts).

In a further aspect of the invention, there is provided Compound 1 in the form of its Form B hydrate solid crystalline polymorph (the Form B polymorph), for example as characterised by an XRPD diffractogram substantially as shown in FIG. 4.

Form B is a hydrate derived from Form A or amorphous forms when Compound 1 is crystallised from an aqueous solvent or when water ingresses at sufficient activity under solvent mediation conditions.

The XRPD patterns of hydrates tend to be somewhat more variable than the XRPD patterns of anhydrous crystalline forms because variation in the amount of water within the structure can lead to variation in interplanar distances and therefore to a shift in the angles of reflection, particularly to smaller angles. Therefore, the values below have an error of ±0.4 degrees, 2-theta value, although the error is more suitably ±0.3 degrees, 2-theta value or even ±0.2 degrees, 2-theta value.

The peak at 11.03 (±0.4 degrees, 2-theta value) in the XRPD diffractogram is particularly useful for distinguishing the Form B hydrate crystalline polymorph of Compound 1 from the Form A polymorph of Compound 1.

Suitably, the major peak at position 11.03 (±0.4 degrees, more suitably ±0.3 degrees or ±0.2 degrees, 2-theta value) and at least three peaks (for example three, four, five, six, seven, eight or all nine) selected from the peaks at positions 5.56, 14.04, 17.28, 18.03, 18.86, 22.08, 23.69, 24.12 and 24.93 (±0.4 degrees, more suitably ±0.3 degrees or ±0.2 degrees, 2-theta values) are observable in the XRPD diffractogram of the Form B polymorph of Compound 1.

Of these, the peaks at positions 5.56 and 22.08 ±0.4 degrees, more suitably ±0.3 degrees or ±0.2 degrees, 2-theta values) are also especially characteristic of the Form A crystalline polymorph and therefore it is typical that at least one and preferably both of these are observable.

More usually, the major peak at position 11.03 (±0.2 degrees, 2-theta value) and at least three peaks (for example three, four, five, six, seven, eight, nine, ten, eleven, twelve, thirteen or all fourteen) selected from the peaks at positions 5.56, 14.04, 17.28, 18.03, 18.86, 19.34, 22.08, 23.69, 24.12, 24.93, 25.98, 26.53, 27.28 and 28.79 (±0.4 degrees, more suitably ±0.3 degrees or ±0.2 degrees, 2-theta values) are observable in the XRPD diffractogram of the Form B polymorph of Compound 1.

As above, suitably at least one and preferably both of the peaks at positions 5.56 and 22.08 (±0.4 degrees, more suitably ±0.3 degrees or ±0.2 degrees, 2-theta values) are observable.

Still more usually, the major peak at position 11.03 (±0.2 degrees, 2-theta values) and at least three peaks (for example three, four, five, six, seven, eight, nine, ten, eleven, twelve, thirteen, fourteen, fifteen, sixteen, seventeen, eighteen or all nineteen) selected from the peaks at positions 5.56, 14.04, 16.58, 17.28 18.03, 18.86, 19.34, 21.19, 22.08, 23.69, 24.12, 24.93, 25.98, 26.53, 27.28, 28.22, 28.79, 30.69 and 30.90 (±0.4 degrees, more suitably ±0.3 degrees or ±0.2 degrees, 2-theta values) are observable in the XRPD diffractogram of the Form B polymorph of Compound 1.

As above, suitably at least one and preferably both of the peaks at positions 5.56 and 22.08 (±0.4 degrees, more suitably ±0.3 degrees or ±0.2 degrees, 2-theta values) are observable.

The XRPD diffractogram of the form B polymorph has peaks at 5.56, 11.03, 14.04, 16.58, 17.28, 18.03, 18.86, 19.34, 20.51, 21.19, 22.08, 23.69, 24.12, 24.93, 25.98, 26.53, 27.28, 28.22, 28.79, 30.69, 30.90, 32.07, 32.40, 35.69, 36.54, 37.95, 38.11, 38.77, 38.85 and 40.09 (±0.2 degrees, 2-theta values) and suitably, the peak at 11.03 and at least three, (for example three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine or all thirty) of the remaining peaks are observable in the resulting XRPD diffractogram.

As above, the major peak at position 11.03 and suitably at least one or preferably both of the peaks at positions 5.56 and 22.08 (±0.2 degrees, 2-theta values) are observable.

The XRPD spectra of Forms B(I) and B(II) were re-run and the 2 theta values and peak intensities are shown in Table 2 below. There is some variation from the values given above but as already discussed, this is within the experimental variation usually found in the XRPD spectra for hydrates.

TABLE 2

2-theta values for Form B

| Angle | d Value | Net Intensity | Gross Intensity | Rel. Intensity |
|---|---|---|---|---|
| 5.4903 | 16.08361 | 4819.28 | 4945.332 | 0.972259 |
| 7.9582 | 11.10067 | 30.53711 | 90.46213 | 0.006161 |
| 10.9682 | 8.06011 | 4956.787 | 5012.935 | 1 |
| 13.8667 | 6.381184 | 316.872 | 362.8172 | 0.063927 |
| 16.4682 | 5.378516 | 540.8261 | 580.6063 | 0.109108 |
| 17.0775 | 5.187952 | 83.50439 | 122.2109 | 0.016846 |
| 17.7919 | 4.981229 | 198.3489 | 241.6474 | 0.040016 |
| 17.8749 | 4.958282 | 139.9648 | 184.0679 | 0.028237 |
| 18.5382 | 4.782356 | 276.4914 | 323.1177 | 0.05578 |
| 18.6669 | 4.749661 | 132.16 | 178.4824 | 0.026662 |
| 19.1626 | 4.627914 | 130.3762 | 172.973 | 0.026303 |
| 21.0099 | 4.224971 | 67.57919 | 107.5554 | 0.013634 |
| 21.9937 | 4.038173 | 2475.427 | 2524.322 | 0.499401 |
| 23.5468 | 3.775217 | 348.6059 | 395 | 0.070329 |
| 23.9220 | 3.71685 | 352.0349 | 401.1489 | 0.071021 |
| 24.7841 | 3.589479 | 232.9215 | 279.4703 | 0.04699 |
| 25.7789 | 3.453165 | 84.44144 | 130.2156 | 0.017036 |
| 26.3371 | 3.381234 | 160.9314 | 207.8773 | 0.032467 |
| 27.0946 | 3.288392 | 175.332 | 223.9506 | 0.035372 |
| 27.9607 | 3.188474 | 49.90835 | 99.61381 | 0.010069 |
| 28.5839 | 3.120357 | 184.4673 | 229.063 | 0.037215 |
| 30.6918 | 2.910683 | 151.5957 | 189.7698 | 0.030583 |
| 31.8493 | 2.807496 | 58.30734 | 102.5992 | 0.011763 |
| 32.2177 | 2.776224 | 32.12725 | 80.85123 | 0.006481 |

TABLE 2-continued 2-theta values for Form B

| Angle | d Value | Net Intensity | Gross Intensity | Rel. Intensity |
|---|---|---|---|---|
| 33.0134 | 2.711107 | 50.32448 | 100.973 | 0.010153 |
| 34.3094 | 2.611602 | 44.75555 | 93.01725 | 0.009029 |
| 35.4517 | 2.53003 | 52.1197 | 101.8601 | 0.010515 |
| 35.7665 | 2.508478 | 17.98241 | 67.71905 | 0.003628 |
| 36.3272 | 2.471038 | 48.18829 | 93.86106 | 0.009722 |
| 37.6362 | 2.38805 | 68.26706 | 123.289 | 0.013772 |
| 37.9362 | 2.369851 | 120.4406 | 178.7094 | 0.024298 |
| 38.6783 | 2.326075 | 61.75185 | 125.2805 | 0.012458 |
| 38.9959 | 2.307857 | 242.4149 | 306.3907 | 0.048906 |
| 39.9136 | 2.256883 | 262.3902 | 323.4152 | 0.052936 |
| 40.5067 | 2.225195 | 22.39023 | 79.76295 | 0.004517 |
| 40.9276 | 2.203276 | 27.25035 | 82.92218 | 0.005498 |
| 42.5445 | 2.123209 | 38.82351 | 86.28522 | 0.007832 |
| 43.1536 | 2.094643 | 39.95578 | 84.92056 | 0.008061 |
| 45.8696 | 1.976732 | 66.91469 | 111.2215 | 0.0135 |
| 48.5902 | 1.872222 | 39.40775 | 81.15257 | 0.00795 |
| 50.8045 | 1.795693 | 29.71339 | 76.13046 | 0.005994 |
| 51.5259 | 1.772234 | 36.43834 | 84.44242 | 0.007351 |

It is apparent that, taking into account experimental variation the peaks in Table 2 with 2 theta values of 5.4903, 10.9682, 17.0775, 17.8749, 18.6669, 19.1626, 21.9937, 23.5468, 23.9220, 24.7841, 25.7789, 26.3371, 27.0946 and 28.5839 correspond to the peaks at 5.56, 11.03, 14.04, 17.28, 18.03, 18.86, 19.34, 22.08, 23.69, 24.12, 24.93, 25.98, 26.53, 27.28 and 28.79 (±0.4 degrees, more suitably ±0.3 degrees or ±0.2 degrees, 2-theta values) mentioned above.

The other peaks in Table 2 similarly correspond to peaks mentioned above.

The Form B polymorph may be micronised and the inventors have demonstrated that the crystal structure is maintained on micronisation. Micronisation suitably results in particles with D50 of ≤5 μm, more suitably ≤3 μm, and D90 of ≤10 μm, more suitably ≤5 μm. For example, D50 may be about 1-5 μm, more suitably about 1-3 μm;

Suitably, the Form B polymorph is substantially free from other forms of Compound 1, such that, for example, in a sample of Compound 1, at least 97%, 97.5, 98%, 98.5%, 99%, 99.5%, 99.6% 99.7%, 99.8% or 99.9% by weight of Compound 1 is present as the Form B polymorph.

The inventors have found that the Form B polymorph may be obtained, for example by crystallising Compound 1 from an aqueous solvent, typically water or water mixed with acetonitrile.

Crystallisation may be achieved by a heat-up cool-down method comprising the steps of:
  i. preparing a saturated solution of Compound 1 in a solvent at a temperature of about 60 to 80° C.;
  ii. cooling the solution to a temperature of about 5 to 30° C.;
  iii. allowing the cooled solution to stand until crystals of Compound 1 form; and
  iv. isolating the crystallised product;

wherein the solvent is an aqueous solvent such as water or water mixed with one or more further solvents such as acetonitrile, cumene, dichloromethane, nitromethane, trifluoro toluene or a mixture of dichloromethane and heptane.

Preferably, the solvent is not pure water.

Any other form of Compound 1 may be used as the starting material for the crystallisation. For example, the Compound 1 used to prepare the saturated solution in step (i) may be amorphous Compound 1 or Compound 1 in the form of its Form A crystalline polymorph.

A particularly suitable solvent is a mixture of acetonitrile and water, for example acetonitrile/water in a ratio of from 5:1 to 1:5 v/v, suitably 5:1 to 3:1 and typically about 4:1 acetonitrile/water.

Crystallisation is suitably not carried out in anisole, butylmethyl ether, cumene, chlorobenzene, ethyl acetate, methylethyl ketone, propionitrile, toluene, trifluorotoluene tetrahydrofuran, dichloromethane or dichloromethane/heptane as these lead to the production of other forms of Compound 1. Crystallisation is also suitably not carried out in acetone, butanol, ethanol, ethyl formate, isopropyl acetate, methyl acetate, nitromethane, 2-propanol, propionitrile or acetonitrile. as this leads to the production of polymorphic Form A of Compound 1.

Surprisingly, the inventors have found that the Form B polymorph of Compound 1 can take two pseudopolymorphic forms. These forms are isostructural and they are indistinguishable by XRPD. However, they vary in their dehydration characteristics as measured by thermogravimetric analysis and differential scanning calorimetry. The first pseudopolymorph undergoes unimodal dehydration and is designated Form B(I) and the second pseudopolymorph undergoes bimodal dehydration and is designated Form B(II). The DSC plot of Form B(I) shows a single dehydration lobe, whereas the DSC plot of Form B(II) shows two dehydration lobes, the first one of which occurs at a lower onset than the dehydration lobe for Form B(I) (see FIGS. 21a and 21b). The sum of the enthalpies of the two lobes of Form B (II) is approximately equal to the enthalpy of the single lobe of Form B (I)) Similarly, FIG. 22a, the TGA plot for Form B(I) shows a single weight change attributable to water loss (−4.95% mg), whereas FIG. 22b, the TGA plot for Form B(II) shows a small weight change (−0.87%) followed by a larger weight loss (−3.87%).

The dehydration behaviours of the two forms are thought to arise from the different locations and binding of the associated water molecules. In order to determine whether they were stable, both forms were subjected to 10 tonne compaction, after which it was found that the dehydration endotherm of the compacted Form B(II) presented as a broad unimodal event, analogous to the unimodal event exhibited by Form B(I). Therefore, the two forms are assumed to be related by isostructural pseudopolymorphism, differing only slightly in the orientation and location of their constituent water molecules.

Form B (I) emerged after compaction of Form B (II), and Form B (I) was unchanged after the same treatment. Moreover, in the DSC plots (FIGS. 21a and 21b), dehydration of lobe I present in Form B (II) occurred at a lower onset temperature than dehydration lobe (I) in Form B (I), indicating that Form B (II) was the less stable hydrate form (metastable hydrate form) and is driven towards the more stable hydrate form, Form B (I), when high compressive force is applied.

To further investigate the stability hierarchy of Form B (I) and Form B (II), an equal portion of both Form B (I) and Form B (II) were competitively slurry ripened in 4 to 1 MeCN/Water (w/w) for 3 days. The resulting solid was confirmed by DSC to be Form B (I) which indicates that Form B unimodal pseudopolymorph is the more stable of the two.

As noted above, both Forms A and B are thermodynamically stable, depending upon the conditions in which they are stored. Form A is thermodynamically stable when stored in solid form, even in moist conditions. Thus, Form A is particularly suitable for transport and storage as a solid, suitably as a micronised solid.

However, when in aqueous suspension, Form A is transformed into Form B, more specifically into Form B(I). It appears that this transformation is preceded by adsorption of water molecules onto the surface of the Form A crystals and that the rate determining step is bimolecular with respect to water rather than proceeding via conversion of Form A into a Form B anhydrate, which is subsequently hydrated. If a pharmaceutical composition comprising an aqueous suspension of Form A is required, the suspension is most suitably made up immediately before administration to a patient so that recrystallisation of Compound 1 as the Form B hydrate does not occur before administration.

Form B(I) has been shown to be thermodynamically stable in aqueous suspension over prolonged periods of time. This makes it particularly useful for use in pharmaceutical formulations which are aqueous suspensions.

Single crystal data was obtained for the Form B(I) pseudopolymorph. The crystal was orthorhombic, space group Pna2$_1$, with lattice parameters as follows:

| | |
|---|---|
| a | 32.1319(3) Å |
| b | 5.56259(5) Å |
| c | 10.24568(9) Å |
| α | 90° |
| β | 90° |
| γ | 90° |

In still another aspect of the invention, there is provided Compound 1 in its solid amorphous form.

Suitably, the amorphous form of Compound 1 is substantially free from other forms of Compound 1, such that, for example, in a sample of Compound 1, at least 97%, 97.5%, 98%, 98.5%, 99%, 99.5%, 99.6% 99.7%, 99.8% or 99.9% by weight of Compound 1 may be present as the amorphous form.

Solid amorphous Compound 1 may be prepared, for example by dissolving Compound 1 in a solvent such as ethyl acetate and removing the solvent under reduced pressure at a temperature of about 30 to 45° C.

Suitably, the Compound 1 used as the starting material will be of Form A or Form E (to be described below).

Figure 6:
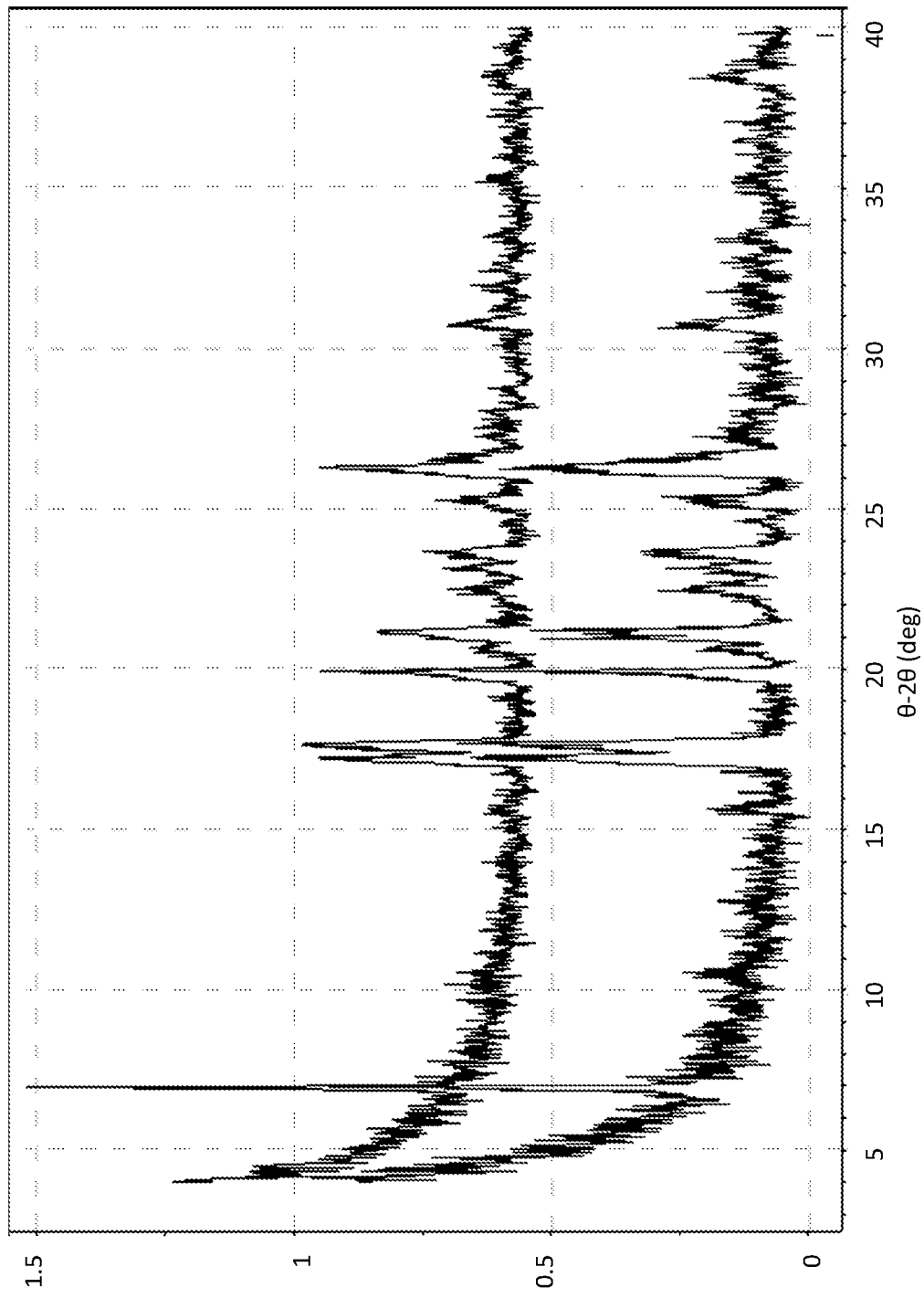
FIG. 6 is an XRPD diffractogram of the non-solvated polymorphic Form C of Compound 1 recrystallised from trifluorotoluene (upper trace) and toluene (lower trace) in Example 3.
Figure 7:
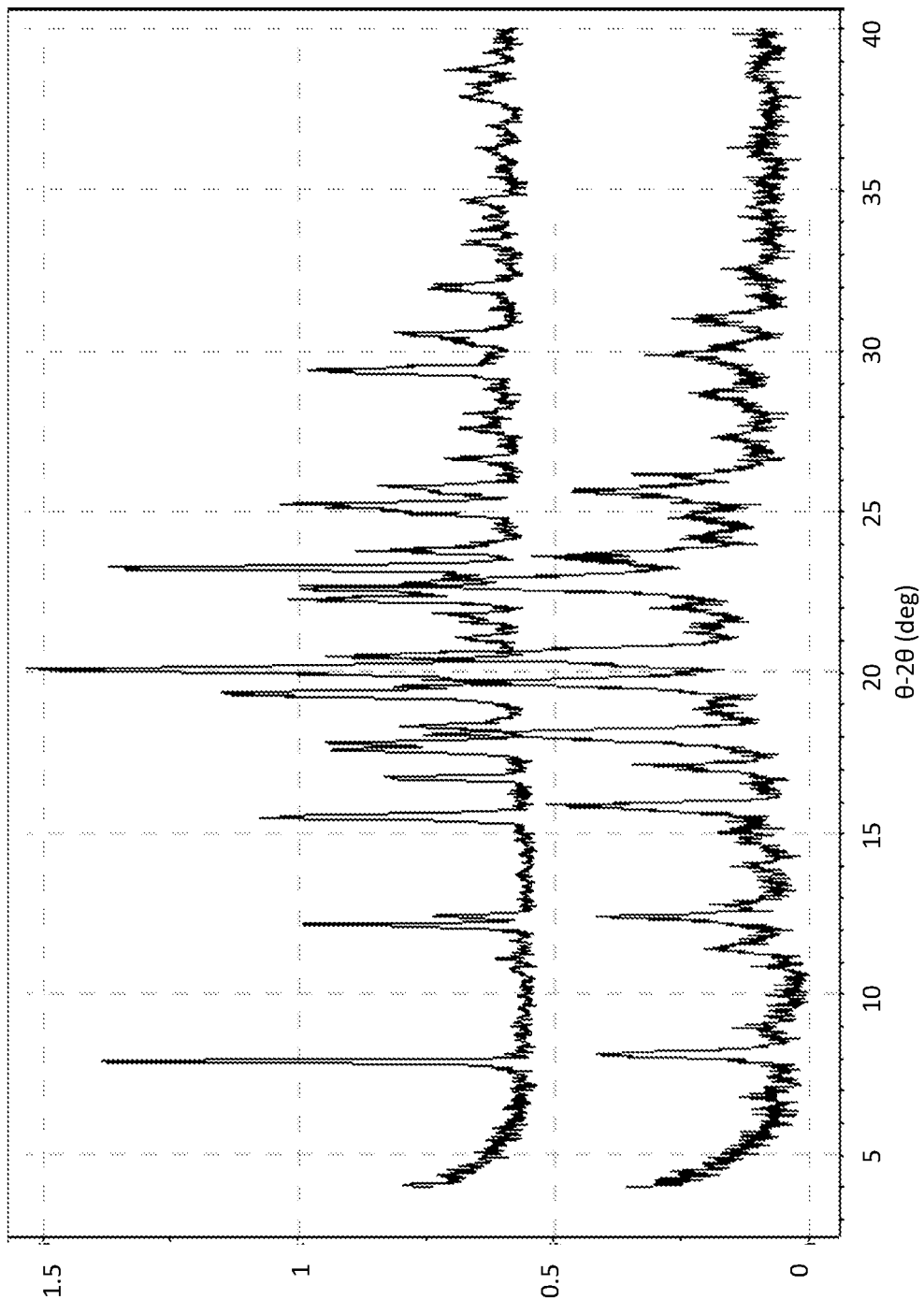
FIG. 7 is an XRPD diffractogram of the ethereal solvate polymorphic Form D of Compound 1: isostructural forms isolated from THF (upper trace) and tert-butyl methyl ether (lower trace) in Example 3.
Figure 8:
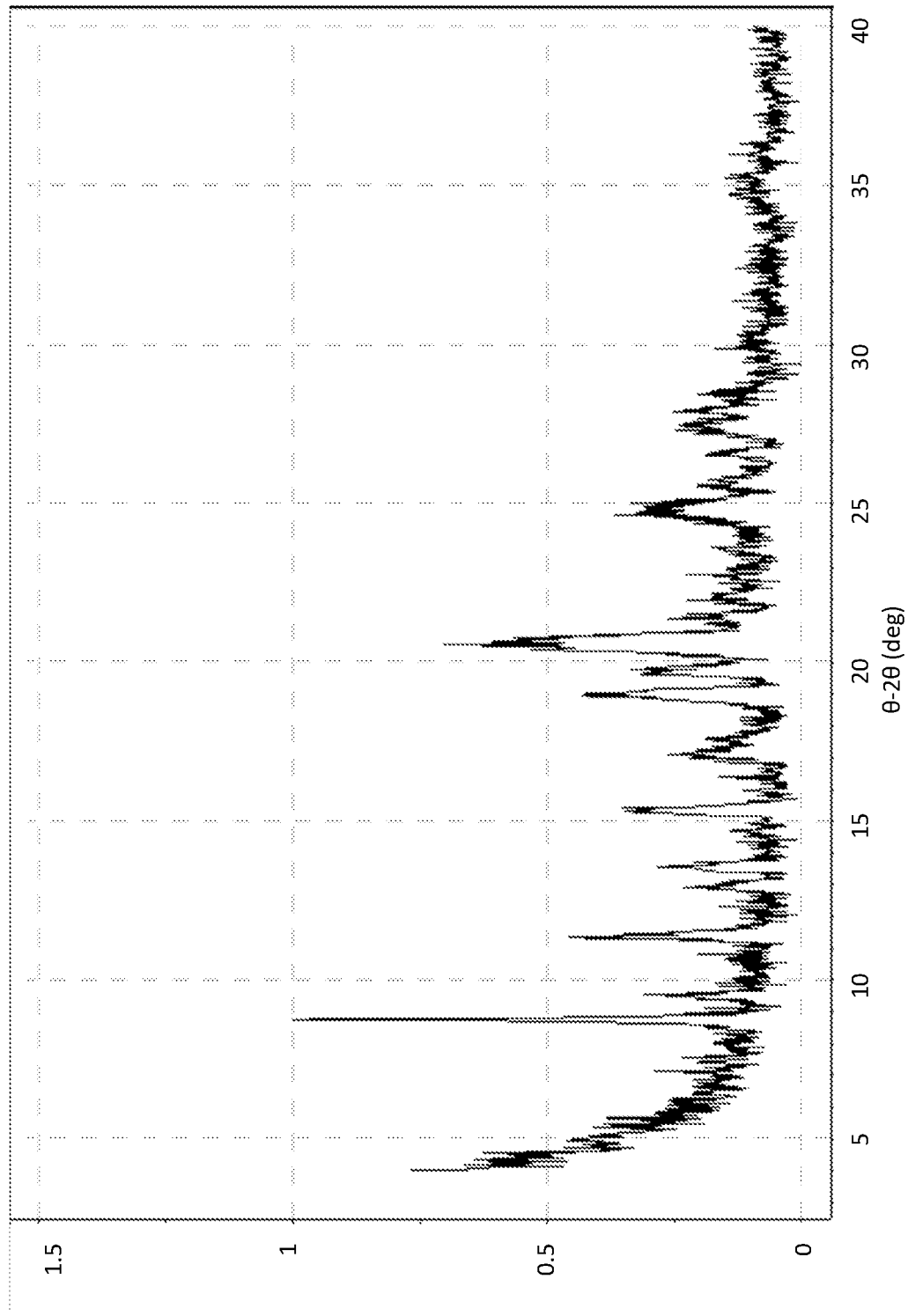
FIG. 8 is an XRPD diffractogram of the methyl ethyl ketone hemi solvate; polymorphic Form E of Compound 1 isolated from methyl ethyl ketone in Example 3.
Figure 9:
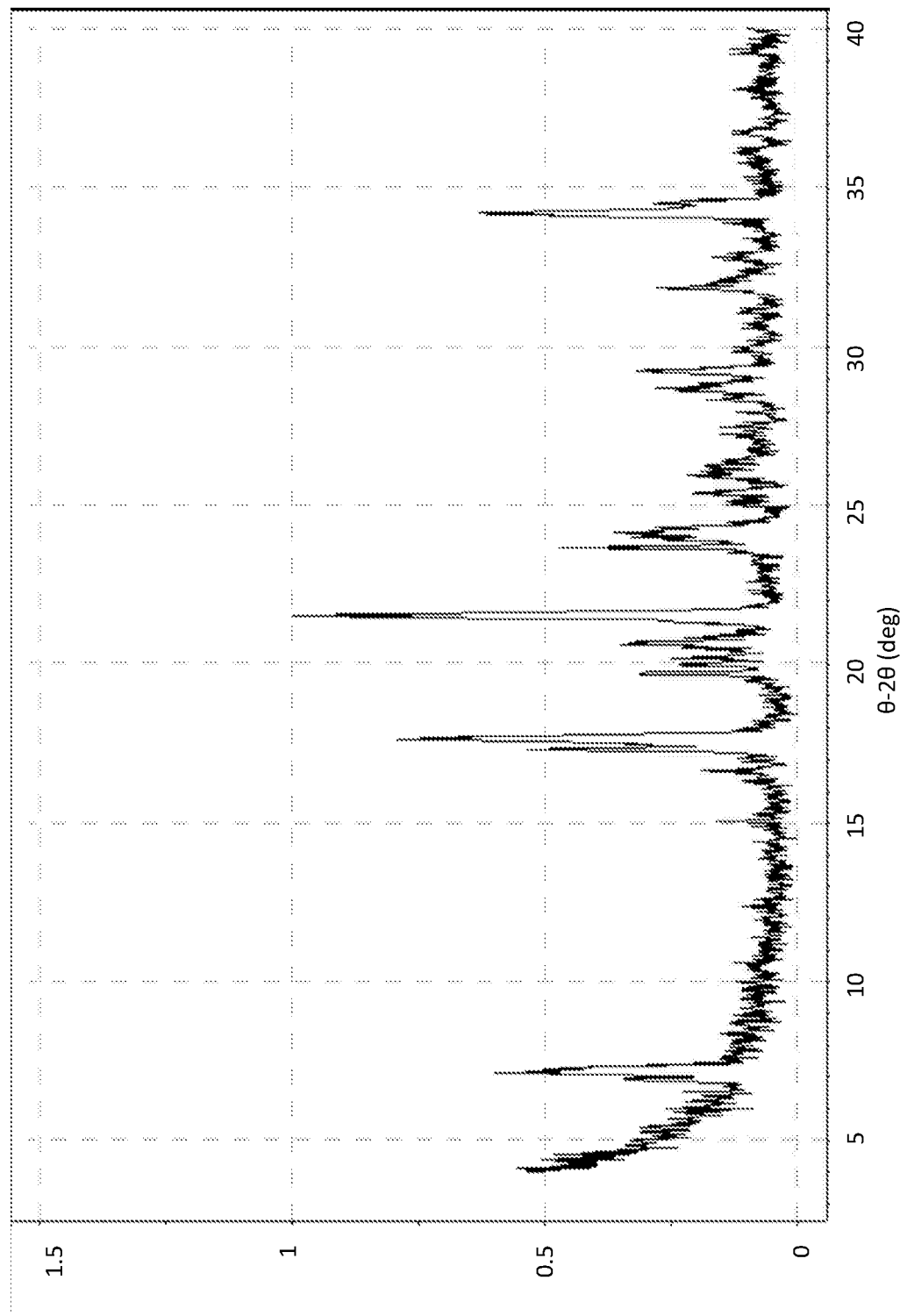
FIG. 9 is an XRPD diffractogram of anhydrous polymorphic Form F of Compound 1 isolated from ethanol in Example 3.
Figure 18:
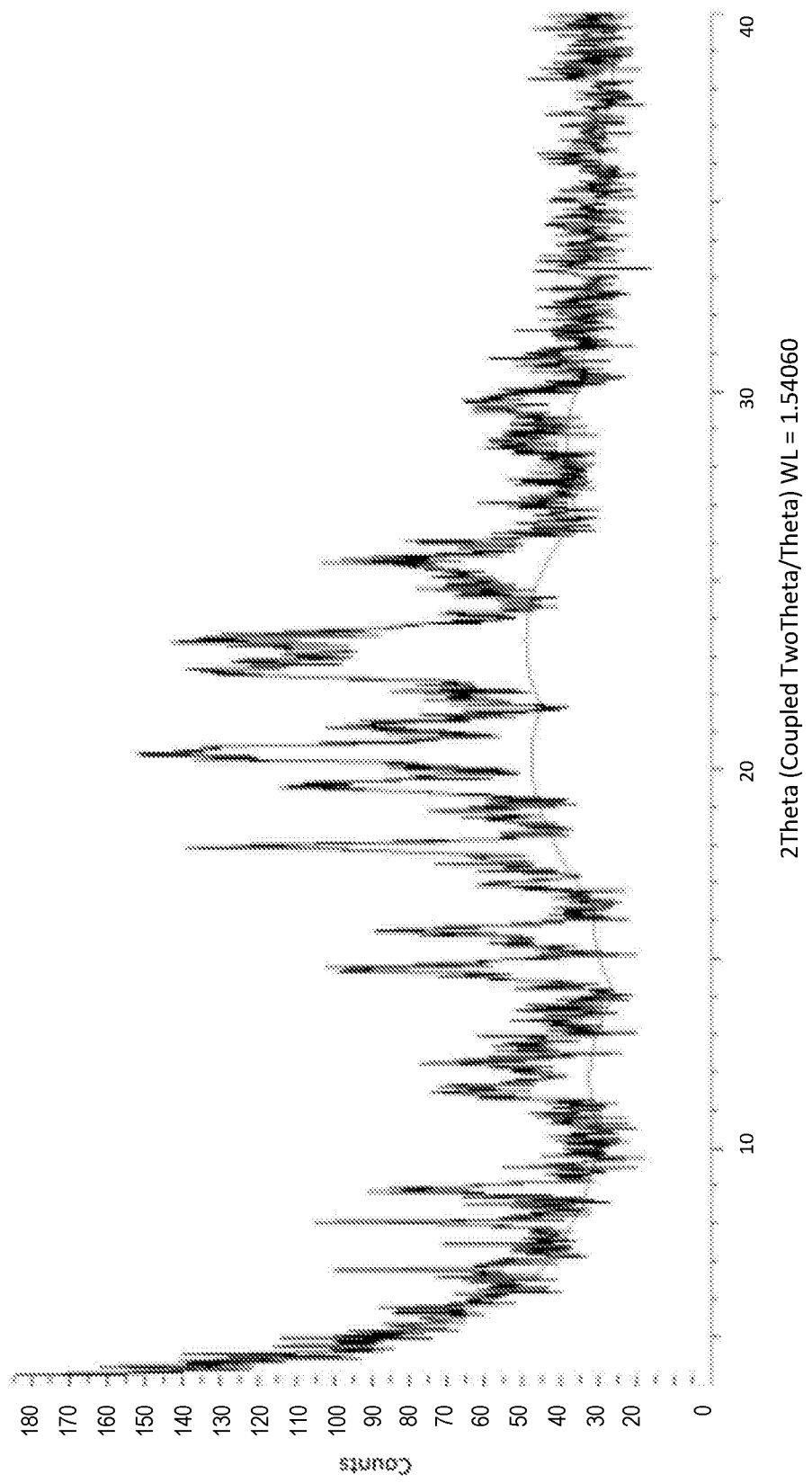
FIG. 18 is an XRPD diffractogram of Form G isolated from THF in Example 7.

Other polymorphic forms of Compound 1 include:

Form C, a non-solvated form isolated from trifluorotoluene or toluene having XRPD diffractogram as shown in FIG. 6;

Form D, an ethereal solvate having an XRPD diffractogram as shown in FIG. 7;

Form E, a methyl ethyl ketone hemi solvate having an XRPD diffractogram as shown in FIG. 8;

Form F, is an anhydrous form derived from ethanol treatment; and having an XRPD diffractogram as shown in FIG. 9;

Form G is a solvate form obtained by suspension equilibration of Form A in THF at 40° C. and having an XRPD diffractogram as shown in FIG. 18.

Figure 10:
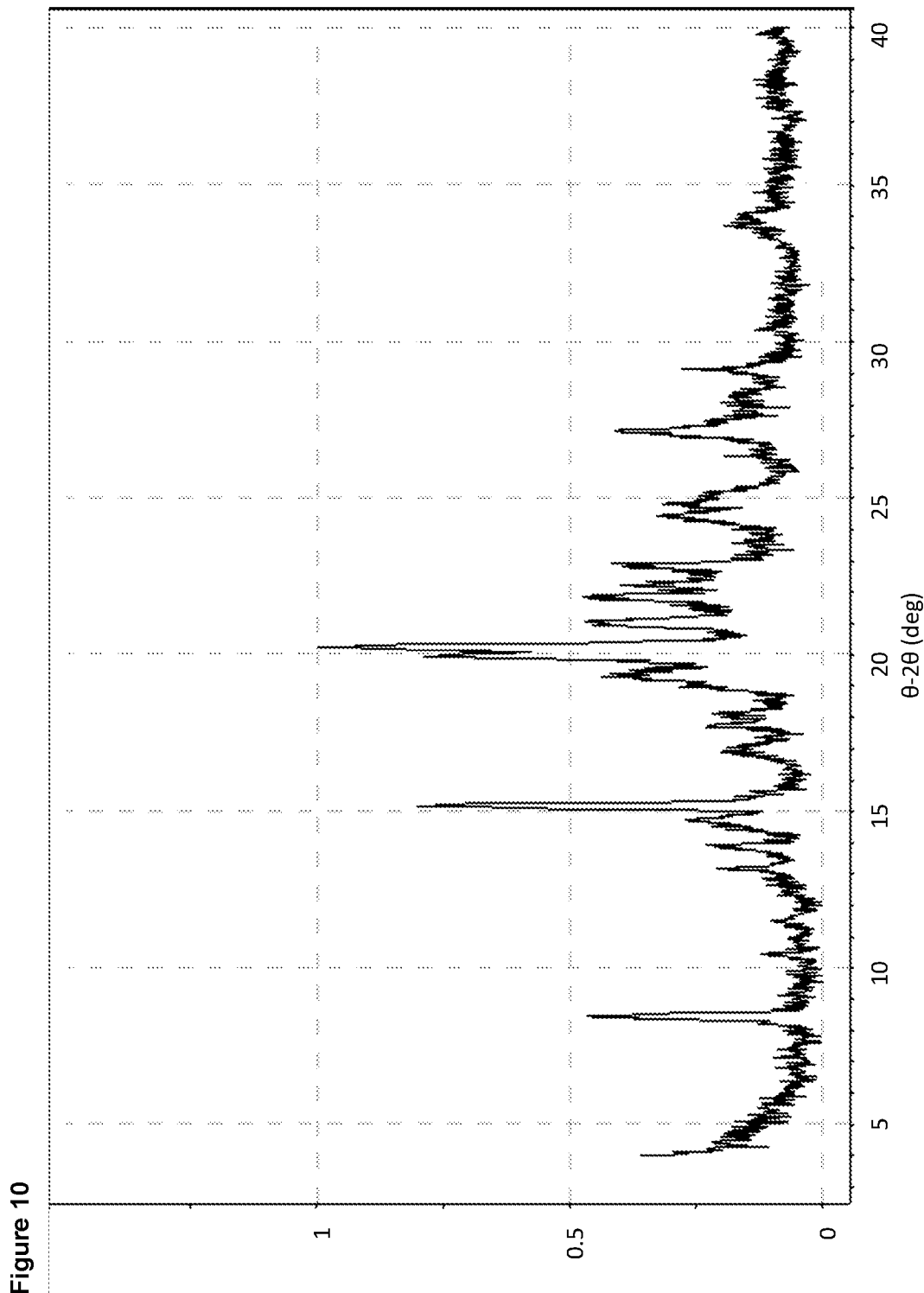
FIG. 10 is an XRPD diffractogram of solvate from H of Compound 1 isolated from cumene in Example 4.

Form H is a solvate form obtained from recrystallisation in cumene and having an XRPD diffractogram as shown in FIG. 10

Compound 1 is a modulator of TMEM16A and therefore, in a further aspect of the invention, there is provided Compound 1 in the form of its Form A polymorph or Form B polymorph, especially its Form B(I) pseudopolymorph, as defined above or in amorphous form for use in the treatment or prophylaxis of diseases and conditions affected by modulation of TMEM16A.

There is also provided Compound 1 in the form of its Form A polymorph or Form B polymorph, especially its Form B(I) pseudopolymorph, as defined above or in amorphous form in the manufacture of a medicament for the treatment or prophylaxis of diseases and conditions affected by modulation of TMEM16A.

There is also provided a method for the treatment or prophylaxis of diseases and conditions affected by modulation of TMEM16A, the method comprising administering to a patient in need of such treatment an effective amount of Compound 1 in the form of its Form A polymorph or Form B polymorph, especially its Form B(I) pseudopolymorph, as defined above or in amorphous form.

The diseases and conditions affected by modulation of TMEM16A include respiratory diseases and conditions, dry mouth (xerostomia), intestinal hypermobility, cholestasis and ocular conditions.

There is also provided:

Compound 1 in the form of its Form A polymorph or Form B polymorph, especially its Form B(I) pseudopolymorph, as defined above or in amorphous form for use in the treatment or prophylaxis of respiratory diseases and conditions.

Compound 1 in the form of its Form A polymorph or Form B polymorph, especially its Form B(I) pseudopolymorph, as defined above or in amorphous form for use in the treatment or prophylaxis of dry mouth (xerostomia).

Compound 1 in the form of its Form A polymorph or Form B polymorph, especially its Form B(I) pseudopolymorph, as defined above or in amorphous form for use in the treatment or prophylaxis of intestinal hypermobility.

Compound 1 in the form of its Form A polymorph or Form B polymorph, especially its Form B(I) pseudopolymorph, as defined above or in amorphous form for use in the treatment or prophylaxis of cholestasis.

Compound 1 in the form of its Form A polymorph or Form B polymorph, especially its Form B(I) pseudopolymorph, as defined above or in amorphous form for use in the treatment or prophylaxis of ocular conditions.

The invention also provides:

The use of Compound 1 in the form of its Form A polymorph or Form B polymorph, especially its Form B(I) pseudopolymorph, as defined above or in amorphous form in the manufacture of a medicament for the treatment or prophylaxis of respiratory diseases and conditions.

The use of Compound 1 in the form of its Form A polymorph or Form B polymorph, especially its Form B(I) pseudopolymorph, as defined above or in amorphous form in the manufacture of a medicament for the treatment or prophylaxis of dry mouth (xerostomia).

The use of Compound 1 in the form of its Form A polymorph or Form B polymorph, especially its Form B(I) pseudopolymorph, as defined above or in amorphous form in the manufacture of a medicament for the treatment or prophylaxis of intestinal hypermobility.

The use of Compound 1 in the form of its Form A polymorph or Form B polymorph, especially its Form B(I) pseudopolymorph, as defined above or in amorphous form in the manufacture of a medicament for the treatment or prophylaxis of cholestasis.

The use of Compound 1 in the form of its Form A polymorph or Form B polymorph, especially its Form B(I) pseudopolymorph, as defined above or in amorphous form in the manufacture of a medicament for the treatment or prophylaxis of ocular conditions.

There is further provided:

A method for the treatment or prophylaxis of respiratory diseases and conditions, the method comprising administering to a patient in need of such treatment an effective amount of Compound 1 in the form of its Form A polymorph or Form B polymorph, especially its Form B(I) pseudopolymorph, as defined above or in amorphous form.

A method for the treatment or prophylaxis of dry mouth (xerostomia), the method comprising administering to a patient in need of such treatment an effective amount of Compound 1 in the form of its Form A polymorph or Form B polymorph, especially its Form B(I) pseudopolymorph, as defined above or in amorphous form.

A method for the treatment or prophylaxis of intestinal hypermobility, the method comprising administering to a patient in need of such treatment an effective amount of Compound 1 in the form of its Form A polymorph or Form B polymorph, especially its Form B(I) pseudopolymorph, as defined above or in amorphous form.

A method for the treatment or prophylaxis of cholestasis, the method comprising administering to a patient in need of such treatment an effective amount of Compound 1 in the form of its Form A polymorph or Form B polymorph, especially its Form B(I) pseudopolymorph, as defined above or in amorphous form.

A method for the treatment or prophylaxis of ocular conditions, the method comprising administering to a patient in need of such treatment an effective amount of Compound 1 in the form of its Form A polymorph or Form B polymorph, especially its Form B(I) pseudopolymorph, as defined above or in amorphous form.

Respiratory diseases and conditions which may be treated or prevented by Compound 1 in the form of its Form A polymorph or Form B polymorph, especially its Form B(I) pseudopolymorph, as defined above or in amorphous form include cystic fibrosis, chronic obstructive pulmonary disease (COPD), chronic bronchitis, emphysema, bronchiectasis, including non-cystic fibrosis bronchiectasis, asthma and primary ciliary dyskinesia.

Dry mouth (xerostomia) which may be treated or prevented by Compound 1 in the form of its Form A polymorph or Form B polymorph, especially its Form B(I) pseudopolymorph, as defined above or in amorphous form may result from Sjorgens syndrome, radiotherapy treatment and xerogenic drugs.

Compound 1 will generally be administered as part of a pharmaceutical composition and therefore the invention further provides a pharmaceutical composition comprising Compound 1 in the form of its Form A polymorph or Form B polymorph, especially its Form B(I) pseudopolymorph, as defined above or in amorphous form together with a pharmaceutically acceptable excipient.

The pharmaceutical composition may be formulated for oral, rectal, nasal, topical (including topical administration to the lung, dermal, transdermal, eye drops, buccal and sublingual), vaginal or parenteral (including subcutaneous, intramuscular, intravenous and intradermal) administration and may be prepared by any methods well known in the art of pharmacy. Compositions for oral administration or topical administration to the lung are particularly suitable.

The composition may be prepared by bringing into association the above defined active agent with the excipient. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing Compound 1 in the form of its Form A polymorph or Form B polymorph, especially its Form B(I) pseudopolymorph, as defined above or in amorphous form in conjunction or association with a pharmaceutically acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Particularly suitable compositions for oral administration comprise aqueous suspensions of Compound 1 in the form of its Form A polymorph or Form B polymorph, especially its Form B(I) pseudopolymorph, as defined above or in amorphous form. When Compound 1 is present as the Form A polymorph, it is most suitably suspended in the aqueous solvent immediately before administration to a patient in order to avoid recrystallisation as the Form B hydrate polymorph. On the other hand, when Compound 1 is present as its Form B polymorph, particularly the Form B(I) pseudopolymorph, the aqueous suspension may be stored for an extended period of time since the Form B(I) pseudopolymorph is thermodynamically stable in aqueous suspension. The aqueous suspension may also include other additives as discussed below.

For topical application to the skin, Compound 1 in the form of its Form A polymorph or Form B polymorph, especially its Form B(I) pseudopolymorph, as defined above or in amorphous form may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

When Compound 1 is present as the Form A polymorph, it is most suitably suspended in an aqueous solvent immediately before administration to a patient in order to avoid recrystallisation as the Form B hydrate polymorph. On the other hand, when Compound 1 is present as its Form B polymorph, particularly the Form B(I) pseudopolymorph, the aqueous suspension may be stored for an extended period of time since the Form B(I) pseudopolymorph is thermodynamically stable in aqueous suspension. The aqueous suspension may also include other additives as discussed below.

Topical administration to the lung may also be achieved by use of a dry-powder formulation. A dry powder formulation will contain the compound of the disclosure in finely divided form, typically with a mass mean diameter (MMAD) of 1-10 μm or a $D_{50}$ of 0.5-10 μm e.g. around 1-5 μm. Powders of the compound of the invention in finely divided form may be prepared by a micronisation process or similar size reduction process. Micronisation may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronisation, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients. Thus, in one embodiment a dry powder formulation according the present disclosure comprises magnesium or calcium stearate. Such formulations may have superior chemical and/or physical stability especially when such formulations also contain lactose.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CON IX, XCELOVAIR and PROHALER.

In one embodiment Compound 1 in the form of its Form A polymorph or Form B polymorph, especially its Form B(I) pseudopolymorph, as defined above or in amorphous form is provided as a micronised dry powder formulation, for example comprising lactose of a suitable grade.

Thus, as an aspect of the invention there is provided a pharmaceutical composition comprising Compound 1 in the form of its Form A polymorph or Form B polymorph, especially its Form B(I) pseudopolymorph, as defined above or in amorphous form in particulate form in combination with particulate lactose, said composition optionally comprising magnesium stearate.

In one embodiment Compound 1 in the form of its Form A polymorph or Form B polymorph, especially its Form B(I) pseudopolymorph, as defined above or in amorphous form is provided as a micronised dry powder formulation, comprising lactose of a suitable grade and magnesium stearate, filled into a device such as DISKUS. Suitably, such a device is a multidose device, for example the formulation is filled into blisters for use in a multi-unit dose device such as DISKUS.

In another embodiment Compound 1 in the form of its Form A polymorph or Form B polymorph, especially its Form B(I) pseudopolymorph, as defined above or in amorphous form is provided as a micronised dry powder formulation, for example comprising lactose of a suitable grade, filled into hard shell capsules for use in a single dose device such as AEROLISER.

In another embodiment Compound 1 in the form of its Form A polymorph or Form B polymorph, especially its Form B(I) pseudopolymorph, as defined above or in amorphous form is provided as a micronised dry powder formulation, comprising lactose of a suitable grade and magnesium stearate, filled into hard shell capsules for use in a single dose device such as AEROLISER.

In another embodiment Compound 1 in the form of its Form A polymorph or Form B polymorph, especially its Form B(I) pseudopolymorph, as defined above or in amorphous form is provided as a fine powder for use in an inhalation dosage form wherein the powder is in fine particles with a $D_{50}$ of 0.5-10 µm e.g. around 1-5 µm, that have been produced by a size reduction process other than jet mill micronisation e.g. spray drying, spray freezing, microfluidisation, high pressure homogenisation, super critical fluid crystallisation, ultrasonic crystallisation or combinations of these methods thereof, or other suitable particle formation methods known in the art that are used to produce fine particles with an aerodynamic particle size of 0.5-10 µm. The resultant particle size distribution may be measured using laser diffraction (e.g. with a Malvern Mastersizer 2000S instrument). The particles may either comprise the compound alone or in combination with suitable other excipients that may aid the processing. The resultant fine particles may form the final formulation for delivery to humans or may optionally be further formulated with other suitable excipients to facilitate delivery in an acceptable dosage form.

Compound 1 in the form of its Form A polymorph or Form B polymorph, especially its Form B(I) pseudopolymorph, as defined above or in amorphous form may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of Compound 1 in the form of its Form A polymorph or Form B polymorph, especially its Form B(I) pseudopolymorph, as defined above or in amorphous form will be about 0.0001 to less than 4.0% (w/w).

Preferably, for topical ocular administration, the compositions comprising Compound 1 in the form of its Form A polymorph or Form B polymorph, especially its Form B(I) pseudopolymorph, as defined above or in amorphous form will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of Compound 1 in the form of its Form A polymorph or Form B polymorph, especially its Form B(I) pseudopolymorph, as defined above or in amorphous form. In addition, Compound 1 in the form of its Form A polymorph or Form B polymorph, especially its Form B(I) pseudopolymorph, as defined above or in amorphous form may also be introduced by means of ocular implants or inserts.

The compositions comprising Compound 1 in the form of its Form A polymorph or Form B polymorph, especially its Form B(I) pseudopolymorph, as defined above or in amorphous form may also include various other ingredients, including, but not limited to, tonicity agents, buffers, surfactants, stabilizing polymer, preservatives, co-solvents and viscosity building agents. Suitable pharmaceutical compositions comprising Compound 1 in the form of its Form A polymorph or Form B polymorph, especially its Form B(I) pseudopolymorph, as defined above or in amorphous form may be formulated with a tonicity agent and a buffer. The pharmaceutical compositions of Compound 1 in the form of its Form A polymorph or Form B polymorph, especially its Form B(I) pseudopolymorph, as defined above or in amorphous form may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of Compound 1 in the form of its Form A polymorph or Form B polymorph, especially its Form B(I) pseudopolymorph, as defined above or in amorphous form. The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/ balance "HLB" in the range of 12.4 to 13.2 and are acceptable for ophthalmic use, such as TritonX114 and tyloxapol.

Additional agents that may be added to the ophthalmic compositions of Compound 1 in the form of its Form A polymorph or Form B polymorph, especially its Form B(I) pseudopolymorph, as defined above or in amorphous form are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of Compound 1 in the form of its Form A polymorph or Form B polymorph, especially its Form B(I) pseudopolymorph, as defined above or in amorphous form to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of Compound 1 in the form of its Form A polymorph or Form B polymorph, especially its Form B(I) pseudopolymorph, as defined above or in amorphous form will be sterile, but typically unpreserved. Such compositions, therefore, generally will not contain preservatives.

Parenteral formulations will generally be sterile.

The medical practitioner, or other skilled person, will be able to determine a suitable dosage for Compound 1 in the form of its Form A polymorph or Form B polymorph, especially its Form B(I) pseudopolymorph, as defined above or in amorphous form and hence the amount of the compound of the invention that should be included in any particular pharmaceutical formulation (whether in unit dosage form or otherwise).

Compound 1 in the form of its Form A polymorph or Form B polymorph, especially its Form B(I) pseudopolymorph, as defined above or in amorphous form may be used in combination with one or more other active agents which are useful in the treatment or prophylaxis of respiratory diseases and conditions.

An additional active agent of this type may be included in the pharmaceutical composition described above but alternatively it may be administered separately, either at the same time as Compound 1 in the form of its Form A polymorph or Form B polymorph, especially its Form B(I) pseudopolymorph, as defined above or in amorphous form or at an earlier or later time.

Therefore, in a further aspect of the present invention there is provided a product comprising Compound 1 in the form of its Form A polymorph or Form B polymorph, especially its Form B(I) pseudopolymorph, as defined above or in amorphous form and an additional agent useful in the treatment or prevention of respiratory conditions as a combined preparation for simultaneous, sequential or separate use in the treatment of a disease or condition affected by modulation of TMEM16A and especially a respiratory disease or condition, for example one of the diseases and conditions mentioned above.

There is also provided Compound 1 in the form of its Form A polymorph or Form B polymorph, especially its Form B(I) pseudopolymorph, as defined above or in amorphous form in combination with an additional agent useful in the treatment or prevention of respiratory conditions as a combined preparation for simultaneous, sequential or separate use in the treatment of a disease or condition affected by modulation of TMEM16A and especially a respiratory disease or condition, for example one of the diseases and conditions mentioned above.

Suitable additional active agents which may be included in a pharmaceutical composition or a combined preparation with Compound 1 in the form of its Form A polymorph or Form B polymorph, especially its Form B(I) pseudopolymorph, as defined above or in amorphous form include:

β2 adrenoreceptor agonists such as metaproterenol, isoproterenol, isoprenaline, albuterol, salbutamol, formoterol, salmeterol, indacaterol, terbutaline, orciprenaline, bitolterol mesylate, pirbuterol, olodaterol, vilanterol and abediterol;

antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;

dornase alpha;

corticosteroids such as prednisone, prednisolone, flunisolide, triamcinolone acetonide, beclomethasone dipropionate, budesonide, fluticasone propionate mometasone furoate and fluticasone furoate;

Leukotriene antagonists such as montelukast and zafirlukast;

anticholinergic compounds, particularly muscarinic antagonists such as ipratropium, tiotropium, glycopyrrolate, aclidinium and umeclidinium;

CFTR repair therapies (e.g. CFTR potentiators, correctors or amplifiers) such as Ivacaftor, QBW251, Bamacaftor (VX659), Elexacaftor (VX445), VX561/CPT-656, VX152, VX440, GLP2737, GLP2222, GLP2451, PTI438, PTI801, PTI808, FDL-169 and FDL-176 and CFTR correctors such as Lumacaftor and Tezacaftor or combinations thereof (for example a combination of Ivacaftor, Tezacaftor and Elexacaftor);

ENaC modulators, particularly ENaC inhibitors;

Antibiotics;

Antivirals such as ribavirin and neuraminidase inhibitors such as zanamivir;

Antifungals such as PUR1900;

Airway hydrating agents (osmoloytes) such as hypertonic saline and mannitol (Bronchitol®); and Mucolytic agents such as N-acetyl cysteine.

When the additional active agent is an ENaC modulator, it may be an ENaC inhibitor such as amiloride, VX-371, AZD5634, QBW276, SPX-101, BI443651, BI265162 and ETD001. Other suitable ENaC blockers are disclosed in our applications WO 2017/221008, WO 2018/096325, WO2019/077340 and WO 2019/220147 and any of the example compounds of those applications may be used in combination with the compounds of general formula (I). Particularly suitable compounds for use in combination with the compounds of general formula (I) include compounds having a cation selected from:

2-[({3-amino-5H-pyrrolo[2,3-b]pyrazin-2-yl}formamido) ethyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium;

2-[({3-amino-5H-pyrrolo[2,3-b]pyrazin-2-yl}formamido) methyl]-6-{[2-(4-{bis[(2S,3R,4R,5R)-2,3,4,5,6-pentahydroxyhexyl]amino}piperidin-1-yl)ethyl]carbamoyl}-1,3-diethyl-1H-1,3-benzodiazol-3-ium;

2-[({3-amino-5H-pyrrolo[2,3-b]pyrazin-2-yl}formamido) methyl]-5-[4-({bis[(2S,3R,4R,5R)-2,3,4,5,6-pentahydroxyhexyl]amino}methyl)piperidine-1-carbonyl]-1,3-diethyl-1H-1,3-benzodiazol-3-ium;

2-[({3-amino-5H-pyrrolo[2,3-b]pyrazin-2-yl}formamido) methyl]-6-[(3R)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido) methyl]-6-[(3S)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido) methyl]-1,3-diethyl-6-{[(1r,4r)-4-{bis[(2S,3R,4R,5R)-2,3,4,5,6-pentahydroxyhexyl]amino}cyclohexyl]carbamoyl}-1H-1,3-benzodiazol-3-ium;

2-[({3-amino-5H-pyrrolo[2,3-b]pyrazin-2-yl}formamido) methyl]-1,3-diethyl-6-{[(1s,4s)-4-{bis[(2S,3R,4R,5R)-2,3,4,5,6-pentahydroxyhexyl]amino}cyclohexyl]carbamoyl}-1H-1,3-benzodiazol-3-ium;

and a suitable anion, for example halide, sulfate, nitrate, phosphate, formate, acetate, trifluoroacetate, fumarate, citrate, tartrate, oxalate, succinate, mandelate, methane sulfonate or p-toluene sulfonate.

The invention will now be described in greater detail with reference to the Examples.

INSTRUMENTATION AND GENERAL CONDITIONS

For Examples 1 and 2

The starting materials and intermediates and Compound 1 may be isolated and purified using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

MS

Mass spectra were run on LC-MS systems using electrospray ionization. These were run using either a Waters Acquity uPLC system with Waters PDA and ELS detectors or Shimadzu LCMS-2010EV systems. [M+H]+ refers to mono-isotopic molecular weights.

NMR

NMR spectra were recorded on a Bruker Avance III HD 500 MHz or a Bruker Avance III HD 250 MHz using the solvent as internal deuterium lock. Spectra were recorded at room temperature unless otherwise stated and were referenced using the solvent peak.

HPLC

The analytical HPLC conditions are as follows:

Method A

Column: Phenomenex Kinetix-XB C18 2.1×100 mm, 1.7 µm
Column Temp 40° C.
Eluents: A: H2O 0.1% formic acid, B: acetonitrile, 0.1% formic acid
Flow Rate: 0.6 mL/min
Gradient: 0-5.3 mins 5-100% B, 5.3-5.8 mins 100% B, 5.8-5.82 mins 100-5% B, 5.82-7.00 mins 5% B

Method E

Column: Kinetex Core-Shell C18 2.1×50 mm 5 µm
Column Temp 40° C.
Eluents: A: H2O+0.1% formic acid, B: acetonitrile+0.1% formic acid
Flow Rate: 1.2 mL/min
Gradient: 0-1.20 mins 5-100% B, 1.20-1.30 mins 100% B, 1.30-1.31 mins 100-5% B

Method F

Column: Phenomenex Gemini-NX C18 2×50 mm 3 µm
Column Temp 40° C.
Eluents: A: 2 mM ammonium bicarbonate, buffered to pH10, B: acetonitrile
Flow Rate: 1 mL/min
Gradient: 0-1.80 mins 1-100% B, 1.80-2.10 mins 100% B, 2.10-2.30 mins 100-1% B

For Examples 3 to 12

DSC

A Mettler Toledo DSC 821 instrument was used for the thermal analysis operating with STARe™ software. The analysis was conducted in 40 µL open aluminium pans, under nitrogen and sample sizes ranged from 1 to 10 mg. Typical analysis method was 20 to 250 at 10° C./minute.

DVS

The moisture sorption properties of the feed API were analysed by DVS (DVS Intrinsic, Surface Measurement System). Approximately 50 mg of API was weighed into an aluminium pan and loaded into the instrument at 25° C. The sample was allowed to equilibrate under dry atmosphere (0% relative humidity) for 1 hour before increasing the humidity from 0% to 30% at 5% step increment and from 30% to 90% at 10% step increment. A desorption cycle was also applied from 90% to 30% (10% step) and from 30% to 0% (5% step). A rate of change by time was set as the equilibrium parameter (1 hour each step). Kinetic and isotherm graphs were calculated.

FT-IR

FT-IR Spectra were acquired using a PerkinElmer Spectrum One FT-IR spectrometer. Samples were analysed directly using a universal ATR attachment in the frequency range 4000 to 600 cm-1. Spectrums were processed using Spectrum CFD, vs. 4.0 PerkinElmer Instruments LLC.

LC-MS

Routine Liquid Chromatography-Mass Spectrometry (LC-MS) data were collected using the Agilent 1260 Infinity II interfaced with 1260 Infinity II DAD HS and Agilent series 1260 Infinity II binary pump.

The instrument used a single quadrupole InfinityLab MSD. The instrument was calibrated up to 2000 Da.

1H NMR

1H NMR Spectra were acquired using a Bruker 400 MHz spectrometer and data was processed using TopSpin™ (Bruker). Samples were prepared in DMSO-D6 at typical concentrations of 10 to 20 mg/mL and up to 50 mg/mL for 1H NMR w/w assay and calibrated to the corresponding non-deuterated solvent residual at 2.50 ppm.

1H NMR w/w Assay

Assays (w/w) of API by 1H NMR spectroscopy were measured by the project chemist. Internal standard 2,3,5,6-terachloronitrobenzene (TCNB), (ca. 20 mg, F.W. 260.89) and API (ca. 20 mg) were dissolved in DMSO-D6 (2.0 ml) and the 1H NMR spectrum was acquired using an extended relaxation method to measure the assay, according to the following equation:

% w/w=[$m$(std.)/M.w.(std.)*∫(sample.) divided by ∫(std.)*M.w.(sample)/$m$(sample.)

Optical (Polarised Light) Microscopy

The instrument used for digital capture was an Olympus BX41 microscope with digital camera attachment. The magnification was ×100 and ×400. Samples were observed under plane polarised and cross polarised light.

Thermal Microscopy

The instrument used for digital capture was an Olympus BX41 microscope with digital camera and Linkam hot stage attachment. The magnification was ×100 and ×400.

Samples were observed under plane polarised and cross polarised light.

TG Analysis

Thermogravimetric analysis was performed using a simultaneous differential technique (SDT, Q600, TA instrument) which combines TGA and DSC signals. Approximately 5 mg of sample was placed into a ceramic pan. The sample was heated under nitrogen atmosphere from room temperature to 600° C. at a rate of 10° C./min. The TGA and DSC signals were analysed using TA Universal analysis software.

XRPD Analyses

X-Ray powder diffraction (XRPD) analysis was carried out using a Bruker D2 Phaser powder diffractometer equipped with a LynxEye detector. The specimens underwent minimum preparation but, if necessary they were lightly milled in a pestle and mortar before acquisition. The specimens were located at the centre of a silicon sample holder within a 5 mm pocket (ca. 5 to 10 mg).

The samples were stationary during data collection and scanned using a step size of 0.02° two theta (2θ) between the range of 4° to 40° and 5° to 60° 2-theta. Data was acquired using either 3 minute or 20 minute acquisition methods. Data was processed using Bruker Diffrac.Suite.

For Examples 13 to 17

DSC

A Mettler Toledo DSC 3 instrument was used for the thermal analysis operating with STARe™ software. The analysis was conducted in 40 μL open aluminium pans, under nitrogen and sample sizes ranged from 1 to 10 mg. Typical analysis method was 20 to 250 at 10° C./minute.

DVS

This was carried out as described above for Examples 3 to 12.

FT-IR

FT-IR Spectra were acquired using a PerkinElmer Frontier FT-IR spectrometer. Samples were analysed directly using a universal ATR attachment in the mid and far frequency ranges 4000 to 30 cm-1. Spectra were processed using Spectrum IR™ software (PerkinElmer Instruments LLC). Standard KBr windows are used for mid-IR applications; polyethylene and polyethylene/diamond windows are used for operation in the far-IR. Further capabilities of the instrument include a liquid flow cell with ZnSe windows used for rapid monitoring of reactions. This couples with Spectrum™ TimeBase software (PerkinElmer), which allows time-resolved measurements to be taken.

LC-MS

This was carried out as described above for Examples 3 to 12.

1H NMR

This was carried out as described above for Examples 3 to 12.

1H NMR w/w Assay

This was carried out as described above for Examples 3 to 12.

Optical (Polarised Light) Microscopy

This was carried out as described above for Examples 3 to 12.

Thermal Microscopy

This was carried out as described above for Examples 3 to 12.

TG Analysis

A Mettler Toledo TGA 2 instrument was used to measure the weight loss as a function of temperature from 25 to 500° C. The scan rate was typically 5 or 10° C. per minute. Experiments and analysis were carried out using the STARe™ software. The analysis was conducted in 100 μL open aluminium pans, under nitrogen and sample sizes ranged from 1 to 10 mg.

XRPD Analyses

X-Ray powder diffraction (XRPD) analysis was carried out using a Bruker D2 Phaser powder diffractometer equipped with a LynxEye detector. The specimens underwent minimum preparation but, if necessary, they were lightly milled in a pestle and mortar before acquisition. The specimens were located at the centre of a silicon sample holder within a 5 mm pocket (ca. 5 to 10 mg).

The samples were stationary during data collection and scanned using a step size of 0.02° two theta (2θ) between the range of 4° to 40° 2 theta. Data was acquired using either 3 minute or 20 minute acquisition methods. Data was processed using Bruker Diffrac.Suite.

ABBREVIATIONS br broad
d doublet
dd doublet of doublets
DCM dichloromethane
DIPEA diisopropylethylamine
DMF N,N-dimethylformamide
DSC Differential scanning calorimetry
EtOAc ethyl acetate
h hours
HPLC high performance liquid chromatography
IR infrared spectroscopy (FT-IR is Fourier transform infrared spectroscopy)
m multiplet
MeCN acetonitrile
mg milligramme
min minute(s)
mL millilitre(s)
mol moles
MS mass spectrometry
m/z mas to charge ratio
N/A not applicable
NMR nuclear magnetic resonance
Rt retention time
s singlet
sat saturated
t triplet
TBTU N,N,N',N'-tetramethyl-O-(benzotriazole-1-yl)uranium tetrafluoroborate
TEA triethylamine
TGA thermogravimetric analysis Example 1—Preparation of N-tert-Butyl-4-[[2-(5-chloro-2-hydroxy-phenyl)acetyl]amino]pyridine-2-carboxamide (Compound 1)—Method of WO2019/145726

Step 1:
4-Amino-N-tert-butyl-pyridine-2-carboxamide

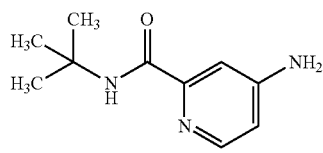

To a mixture of 4-aminopyridine-2-carboxylic acid (8.0 g, 57.92 mmol), TBTU (22.32 g, 69.5 mmol) and TEA (24.22 mL, 173.76 mmol) in DMF (100 mL) was added 2-methylpropan-2-amine (1.69 mL, 69.5 mmol). The resulting mixture was stirred at room temperature for 22 hours and then concentrated in vacuo. The crude material was purified by chromatography on silica eluting with 3.5M methanolic ammonia in DCM and product fractions combined and concentrated in vacuo to yield the titled compound as a light yellow solid.

1H NMR (500 MHz, Methanol-d4) δ 7.99 (d, J=5.6 Hz, 1H), 7.23 (d, J=2.2 Hz, 1H), 6.62 (dd, J=5.6, 2.4 Hz, 1H), 1.45 (s, 9H).

LC-MS (Method F): Rt 1.47 mins; MS m/z 194.3=[M+H]+(100% @ 215 nm)

Step 2: N-tert-Butyl-4-[[2-(5-chloro-2-methoxy-phenyl)acetyl]amino]pyridine-2-carboxamide

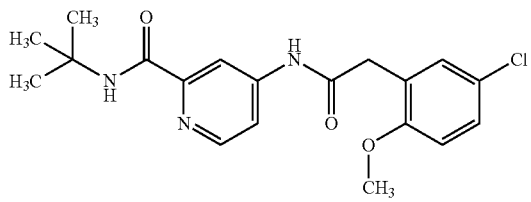 [SMILES: COc1ccc(Cl)cc1CC(=O)Nc1ccnc(C(=O)NC(C)(C)C)c1]

A solution of 2-(5-chloro-2-methoxy-phenyl)acetic acid (2.26 g, 11.27 mmol) in thionyl chloride (8.13 mL, 92.21 mmol) was heated at 70° C. for 30 minutes. After cooling to room temperature, excess thionyl chloride was removed in vacuo, azeotroping with toluene. The resulting residue was dissolved in DCM (5 mL) and added to a solution of 4-amino-N-tert-butyl-pyridine-2-carboxamide (step 1) (2.0 g, 10.25 mmol) and DIPEA (2.15 mL, 12.29 mmol) in DCM (25 mL). The mixture stirred at room temperature for 1 hour and then diluted with water (50 mL) and extracted with DCM. The combined organic extracts were washed with brine (50 mL), dried over Na$_2$SO$_4$ and concentrated in vacuo. The crude residue was purified by chromatography on silica eluting with 0-50% EtOAc in heptane to afford the titled compound as a pale orange powder.

1H NMR (500 MHz, Chloroform-d) δ 8.39 (d, J=5.6 Hz, 1H), 8.20 (dd, J=5.6, 2.2 Hz, 1H), 8.10 (br s, 1H), 7.98 (br s, 1H), 7.56 (d, J=2.1 Hz, 1H), 7.29-7.26 (m, 2H), 6.89 (d, J=9.5 Hz, 1H), 3.94 (s, 3H), 3.70 (s, 2H), 1.47 (s, 9H).

LC-MS (Method E): Rt 1.21 mins; MS m/z 376.1/378.1=[M+H]+(92% @ 215 nm)

Step 3: N-tert-Butyl-4-[[2-(5-chloro-2-hydroxy-phenyl)acetyl]amino]pyridine-2-carboxamide To a solution of N-tert-Butyl-4-[[2-(5-chloro-2-methoxy-phenyl)acetyl]amino]pyridine-2-carboxamide (step 2) (2.7 g, 6.82 mmol) in DCM (10 mL) at 0° C. was added dropwise 1M BBr$_3$ in DCM (27.3 mL, 27.3 mmol). Once addition was complete the mixture was allowed to warm to room temperature and stirred for 1 hour. The reaction was quenched by slow addition of water (10 mL) and the DCM removed in vacuo. The resulting residue was dissolved in EtOAc and washed with sat. NaHCO$_3$ solution (50 mL) and brine (50 mL). The organic portion was separated, dried Na$_2$SO$_4$ and concentrated in vacuo. The crude residue was purified by chromatography on silica eluting with 0-70% EtOAc in heptane to afford the product as an orange powder. This was further purified by reverse phase chromatography eluting with 0-100% MeCN in water with 0.1% formic acid to give the product as a colourless powder. The product was recrystallised from MeCN to afford the titled compound. A second crop was isolated by dropwise addition of water to the MeCN filtrate followed by heating and cooling of the mixture.

$^1$H NMR (500 MHz, DMSO-d6) δ 10.69 (br s, 1H), 9.82 (br s, 1H), 8.44 (d, J=5.5 Hz, 1H), 8.17 (d, J=1.9 Hz, 1H), 8.03 (s, 1H), 7.82 (dd, J=5.5, 2.2 Hz, 1H), 7.22 (d, J=2.7 Hz, 1H), 7.12 (dd, J=8.6, 2.7 Hz, 1H), 6.80 (d, J=8.6 Hz, 1H), 3.67 (s, 2H), 1.40 (s, 9H).

LC-MS (Method A): Rt 3.28 mins; MS m/z 362.1/364.1=[M+H]+(99% @ 215 nm).

Figure 19:
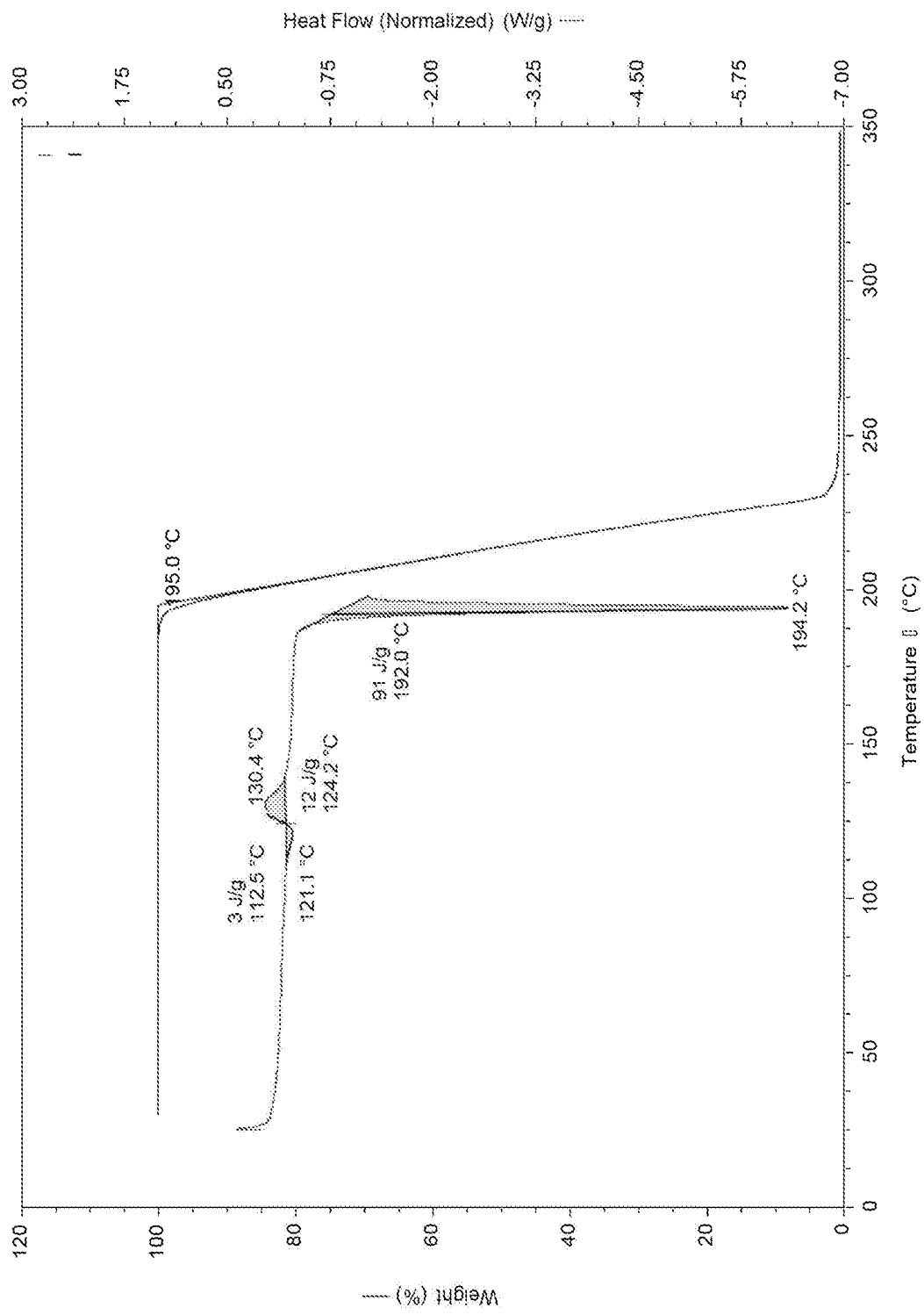
FIG. 19 is a TGA plot (upper trace) showing an onset of weight loss transition at 195.0° C. and a DSC thermogram (lower line) showing Lobe 1: integral −3 J/g; onset 112.5° C.; peak 121.1° C.; Lobe 2: integral 12 J/g; onset 124.2° C.; peak 130.4° C.; Lobe 3: integral −91 J/g, onset 192° C.; peak 194.2.° C. for the material obtained from Example 1.
Figure 20:
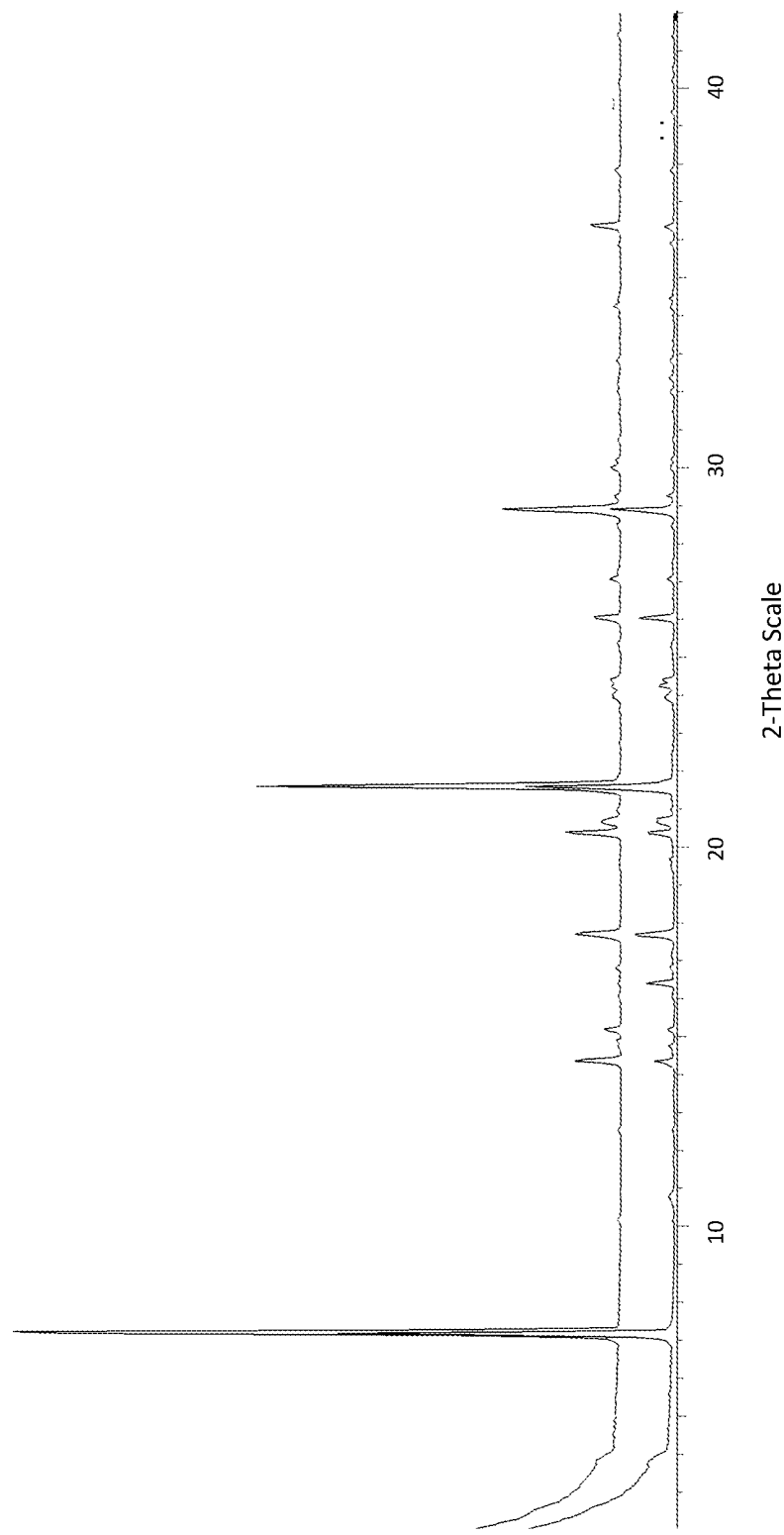
FIG. 20 is an XRPD diffractogram of the material obtained from Example 1 as prepared (lower trace) and after storage for 7 days at 40° C. and 75% relative humidity (upper trace).

XRPD analysis (see FIG. 20) showed that the Compound 1 prepared by this method was crystalline and shares a number of peaks consistent with Form A in addition to a number of unique peaks suggesting a mixture of at least two different polymorphic forms, including Form A. The DSC thermogram (FIG. 19) indicates that the material contains at least one polymorph that is not Form A as shown particularly by exothermic and endothermic events between 112.5° C. and 130.4° C. Thermogravimetric analysis also shows that the product is not a hydrate or other solvate.

Example 2—Preparation of Crystalline Polymorphic Form A

A batch of Compound 1 was prepared according to the method set out in Example 1 (14.6 g). The material was recrystallized by suspending in MeCN (200 mL) and heating to reflux until all solids had dissolved. This was followed by slow cooling to room temperature over several hours or overnight. The resulting crystalline solid was filtered and dried in a vacuum oven to give N-tert-butyl-4-[[2-(5-chloro-2-hydroxy-phenyl)acetyl]amino]pyridine-2-carboxamide (Compound 1) (12.9 g, 353 mmol, 33% yield) as a colourless crystalline solid (Polymorph A). The XRPD diffractogram, DSC thermogram, and DVS plots for this material are shown in FIGS. 1a, 1b, 2, 3a and 3b.

Example 3—Preparation of Amorphous Compound 1

Figure 11:
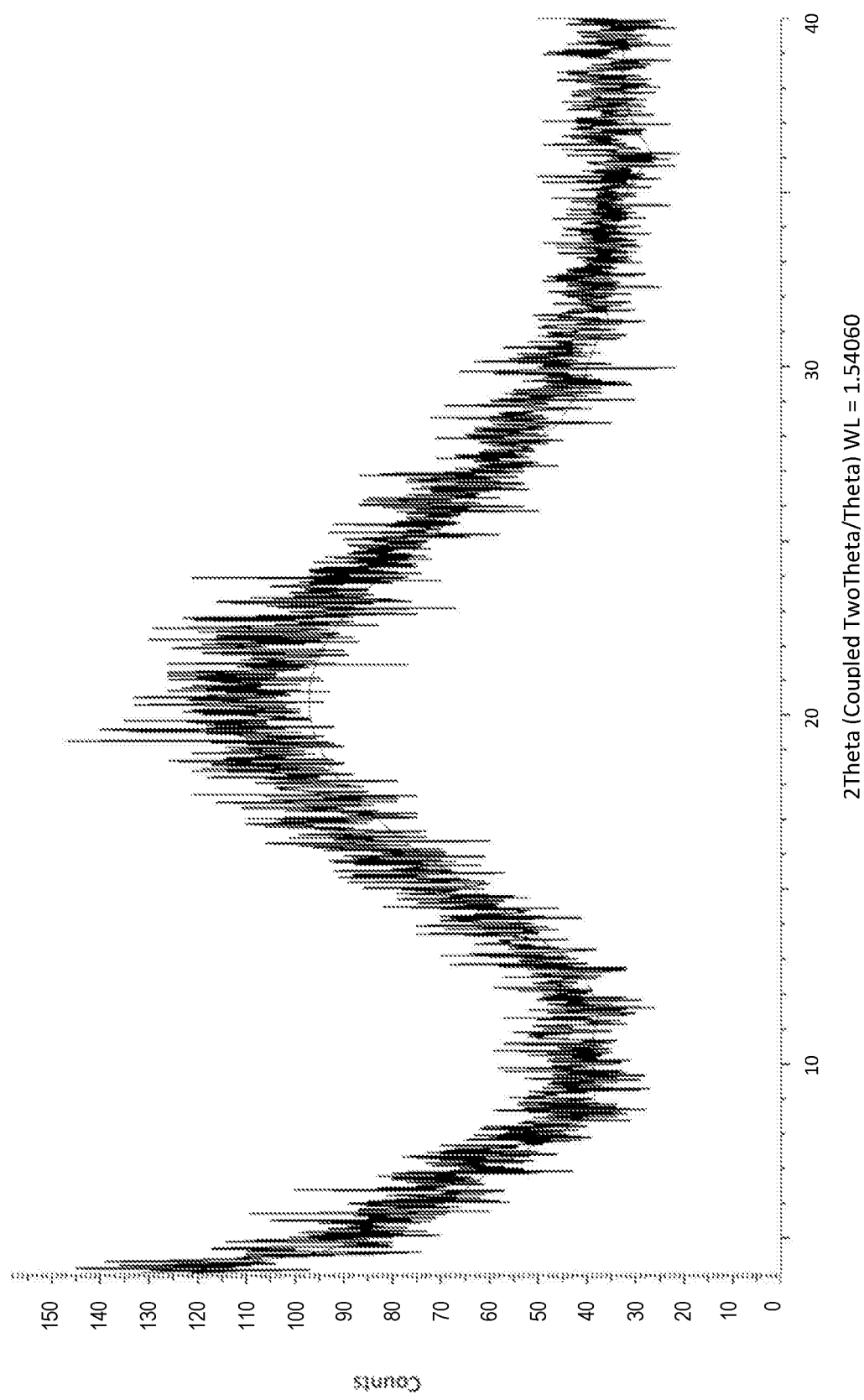
FIG. 11 is an XRPD diffractogram of the amorphous product of Example 3 before oven drying.
Figure 12:
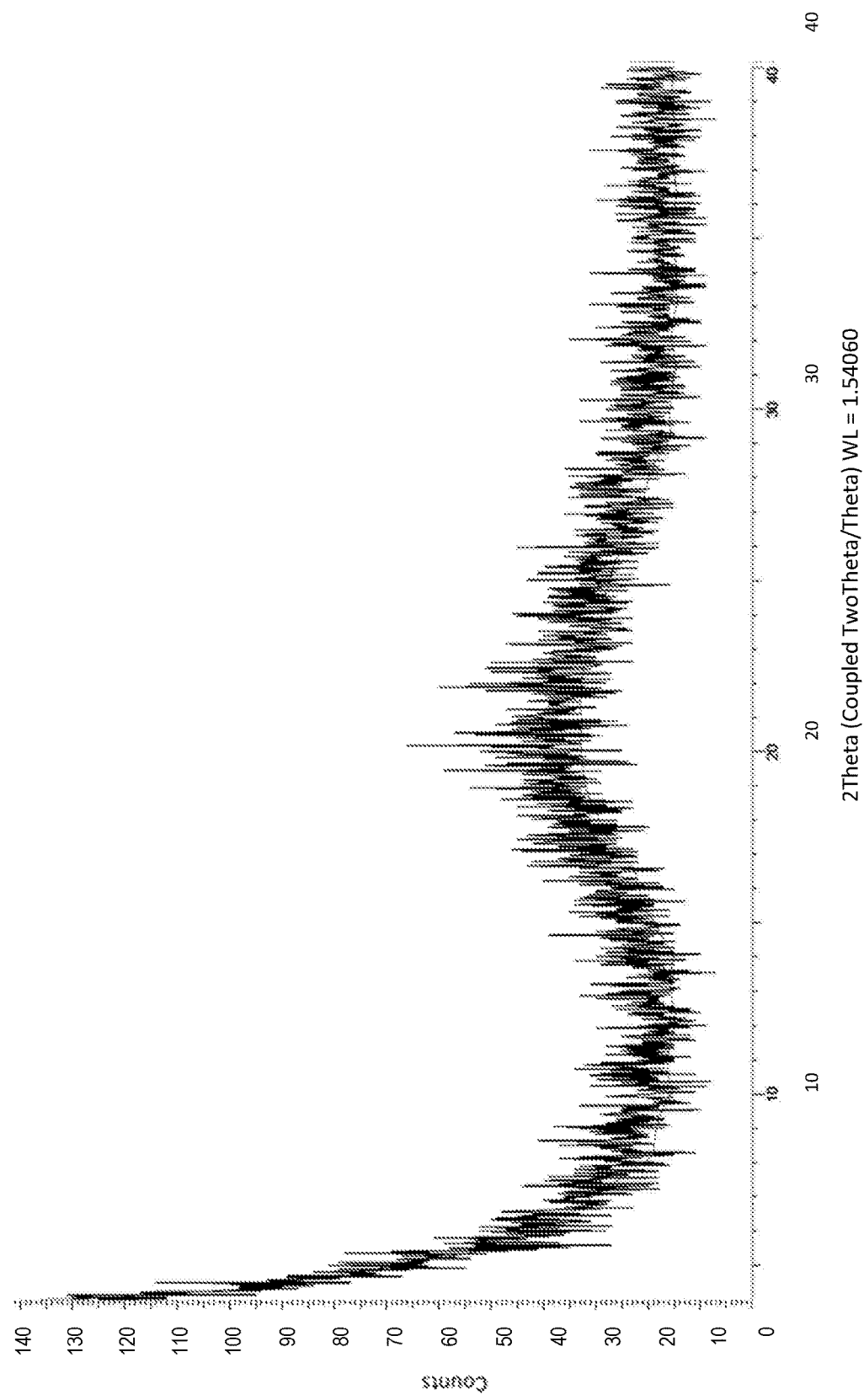
FIG. 12 is an XRPD diffractogram of the amorphous product of Example 3 after oven drying.

Compound 1 Form A (1.50 g, 1.0 wt) was dissolved in ethyl acetate (30 ml, 20 vol). The solution was filtered through a PTFE membrane and rapidly evaporated under reduced pressure at 40° C. and analysed by XRPD and $^1$H NMR. The crude product was dried under reduced pressure at 40° C. overnight. The product was analysed by XRPD (FIGS. 11 and 12) to confirm the amorphised product had not recrystallised after oven drying and by 1H NMR to confirm the reduction in solvent content.

Example 4—Anhydrous Suspension Equilibrations of Amorphous Phase at 20° C.

Amorphous Compound 1 (ca 50 mg, 1.0 wt.) and the appropriate solvent (1000 μl, 20 vol.) were charged to separate vessels and stirred for 7 days at 20° C. After this time the products were cooled, isolated by filtration, washed with recycled maturation solvent, dried under reduced pressure at 40° C. and analysed by XRPD for evidence of alternative crystalline forms. The results are shown in Table 3

TABLE 3

Phase equilibration in anhydrous solvents at 20° C.

| Solvent | Observation (t = 0) | Observation (t = 7 days) | Output form |
|---|---|---|---|
| Acetone | Dissolved | Dissolved | A |
| Acetonitrile | Mobile suspension | Feint suspension | A |
| Anisole | Mobile suspension | Suspension | A |
| Butanol | Dissolved | Dissolved | — |
| Tert-butyl methyl ether | Mobile suspension | Suspension | D |
| Chlorobenzene | Fine suspension | Suspension | A |
| Cumene | Mobile suspension | Suspension | A |
| Dichloromethane | Very fine suspension | Suspension | A |
| Ethanol | Dissolved | Dissolved | F |
| Ethyl acetate | Very fine suspension | Feint suspension | A |
| Ethyl formate | Mobile suspension | Feint suspension | A |
| Isopropyl acetate | Fine suspension | Suspension | A |
| Methyl acetate | Very fine suspension | Feint suspension | A |
| Methyl ethyl ketone | Dissolved | Dissolved | E |
| Nitromethane | Mobile suspension | Suspension | A |
| 2-propanol | Dissolved | Dissolved | A |
| Propionitrile | Fine suspension | Feint suspension | A |
| Tetrahydrofuran | Dissolved | Dissolved | D |
| Toluene | Fine suspension | Suspension | C |
| Trifluorotoluene | Fine suspension | Suspension | C |
| water | Mobile suspension | Suspension | B |
| Dichloromethane/heptane | Mobile suspension | Suspension | B |
| Acetonitrile/water* | Mobile suspension | Suspension | B |

*Purified water was included in the screen

The chemical identity of all products was confirmed as Compound 1 by $^1$H NMR. No significant chemical degradation was observed; therefore, the different diffraction patterns observed were not attributed to the presence of different chemical entities.

Form A was the most abundant form isolated. Several other diffraction patterns were observed, some of which were anhydrous and some were solvated.

Figure 5:
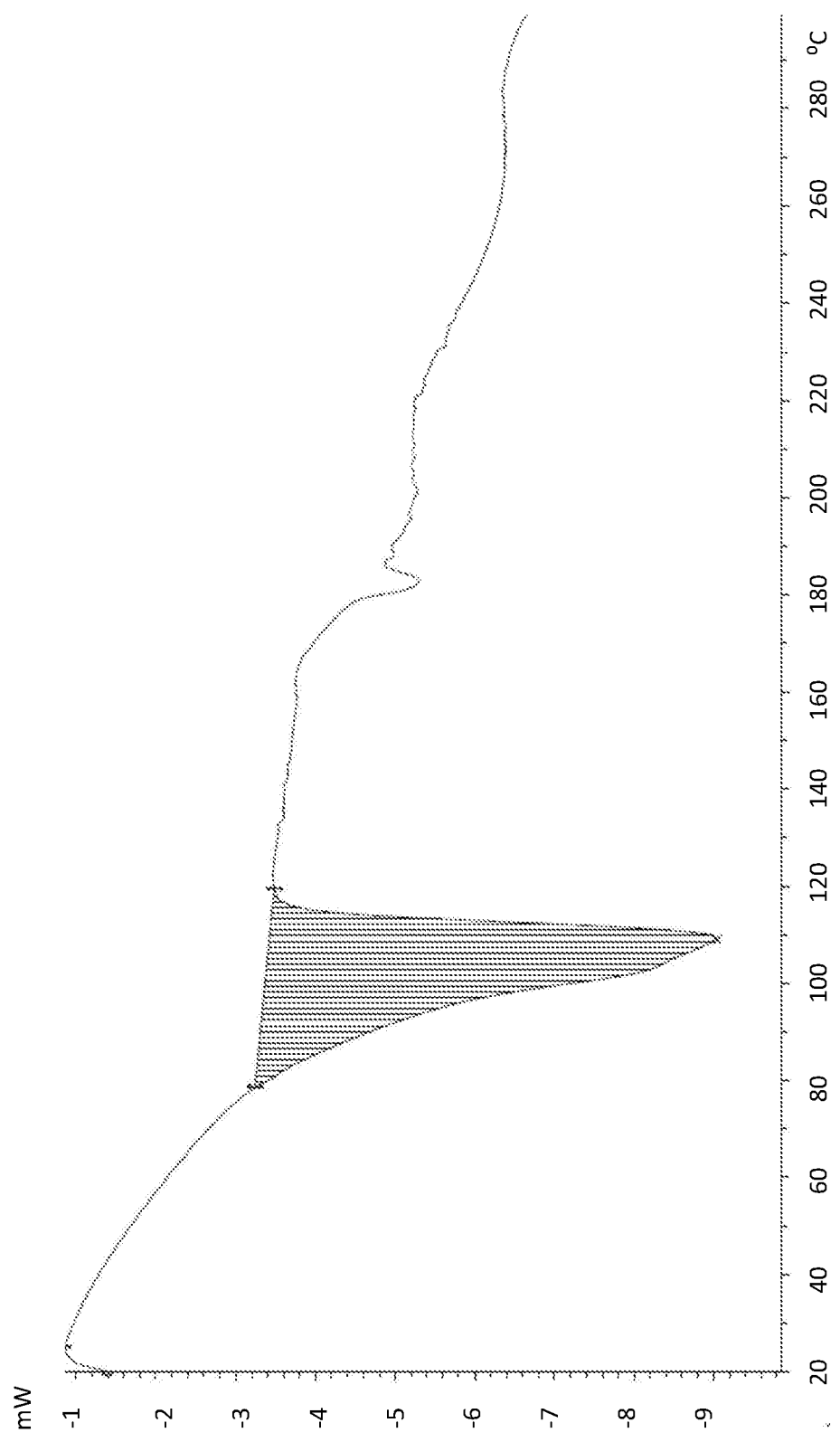
FIG. 5 is a DSC thermogram for polymorphic Form B of Compound 1 acquired at a ramp rate of +10° C./minute showing an endotherm which can be attributed to loss of water from the hydrate: integral −96.97 mW° C., onset 90.90° C.; endset 114.65° C.
Figure 13:
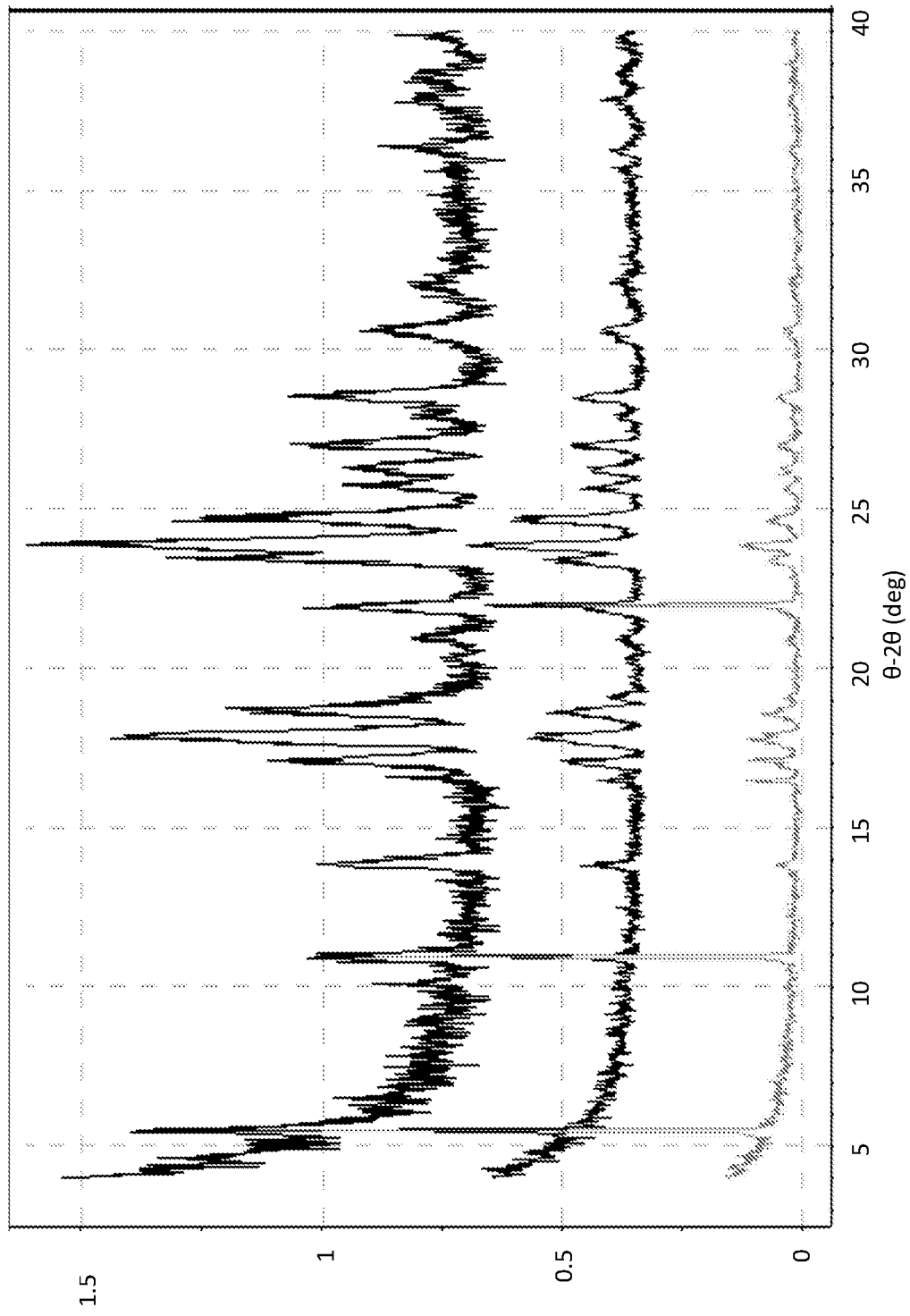
FIG. 13 is an XRPD diffractogram of Compound 1 isolated from water (upper trace), DCM/heptane (middle trace) and acetonitrile/water (lower trace) in Example 4 and shows that all these products are the same and are consistent with the Form B hydrate (by comparison with FIG. 4). The hydrate formation from DCM/heptane must be attributed to water ingress or the presence of damp heptane.
Figure 14:
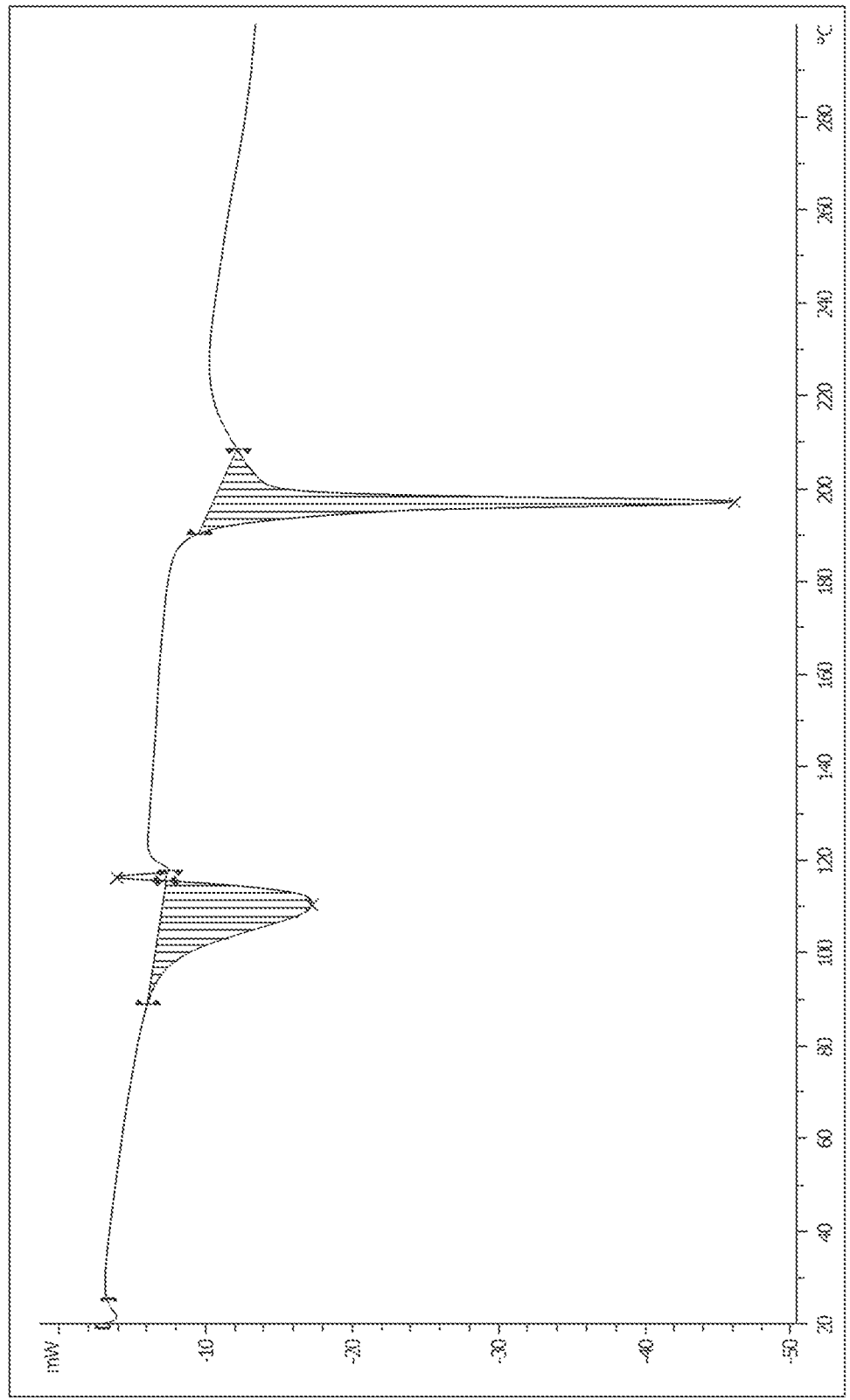
FIG. 14 is a DSC thermogram of the product isolated from DCM/heptane in Example 4, temperature range 20-300° C., heating at 10° C. per minute. It shows an endotherm which can be attributed to loss of water from a hydrate and is consistent with Form B indicating ingress of water during suspension equilibration, presumably from bulk heptane; Lobe 1: integral −114.32 mW° C., onset 98.45° C., peak 110.50° C., endset 115.32° C.; Event 2: integral 9.95 mW° C., onset 115.33° C., peak 116.17° C., endset 117.26° C.; Lobe 3:Integral −132.83 mW° C., onset 194.49° C., peak 197.17° C., endset 199.06° C.

In this screen, Form B (hydrate) was generated when water was present (the DSC of Form B shown in FIG. 5 has an endotherm from 90.90° C. to 114.65° C. which can be attributed to loss of water from the hydrate). The exception to this was the product isolated from DCM/heptane, where the Form B was formed despite the lack of water as a co-solvent. The hydrate formation can be attributed to water ingress or the presence of damp heptane; no solvents were detected by $^1$H NMR, and XRPD (refer to FIG. 13) were consistent with isostructural Form B hydrates (see FIG. 4). DSC analysis (FIG. 14) was consistent with Form BI (see FIG. 21a).

Form C was isolated from trifluorotoluene and toluene and the XRPD diffractogram is shown in FIG. 6. Both the products obtained were non-solvated and DSC analyses showed a melt event and crystallisation into Form A and subsequent melt event.

Figure 15A:
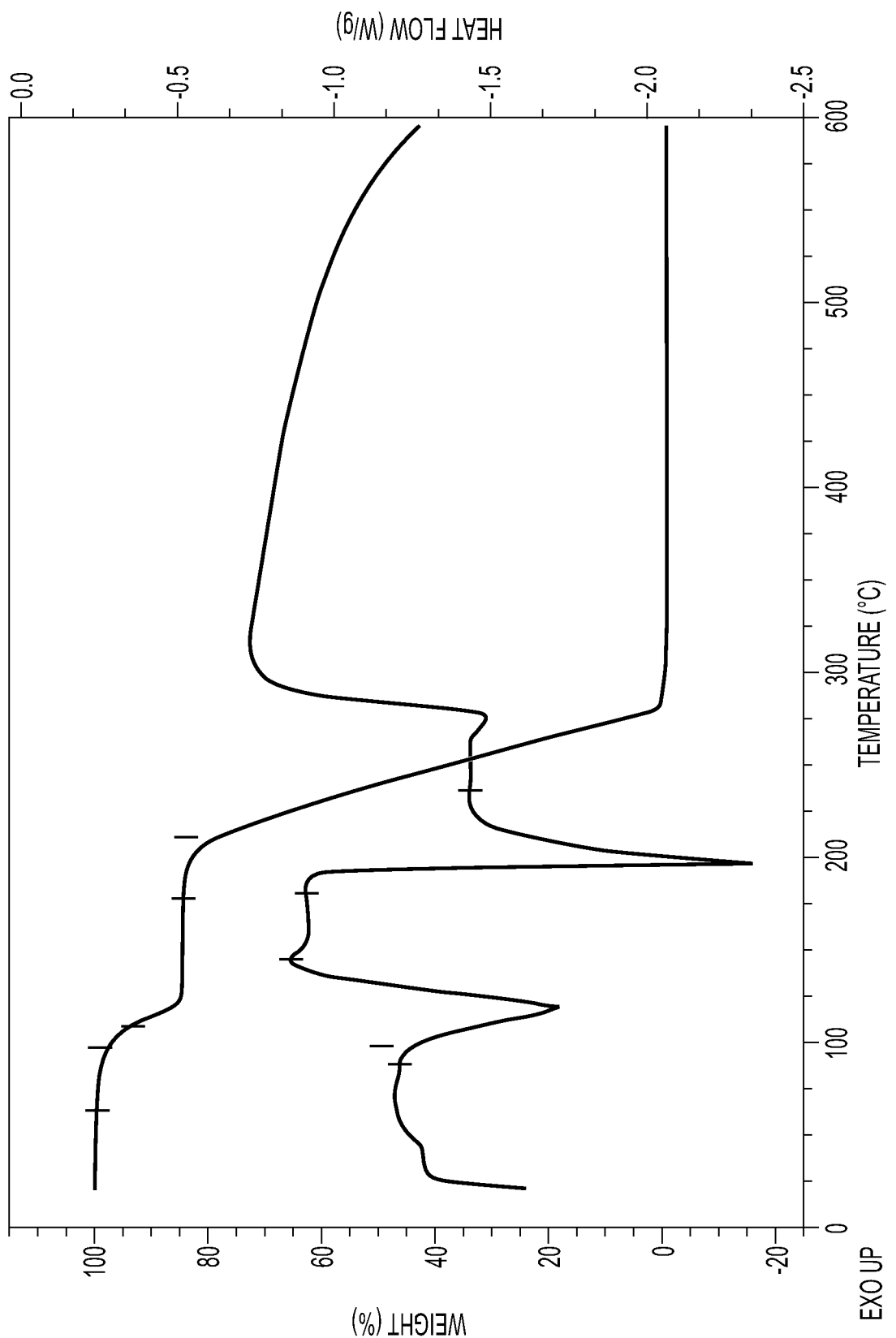
FIG. 15a shows overlaid DSC and TGA thermograms of the ethereal solvate Form D isolated from tetrahydrofuran in Example 4 and shows a first weight loss transition at about 97.27° C. which corresponded to about 14 to 15% w/w and which was attributed to solvent release (sample contained 12.5% w/w THF by $^1$H NMR). DSC, Lobe 1: integral −90.50 J/g, onset 98.44° C., peak 118.9° C.; Lobe 2: integral −101.8 J/g, onset 194.06° C., peak 196.72° C.
Figure 15B:
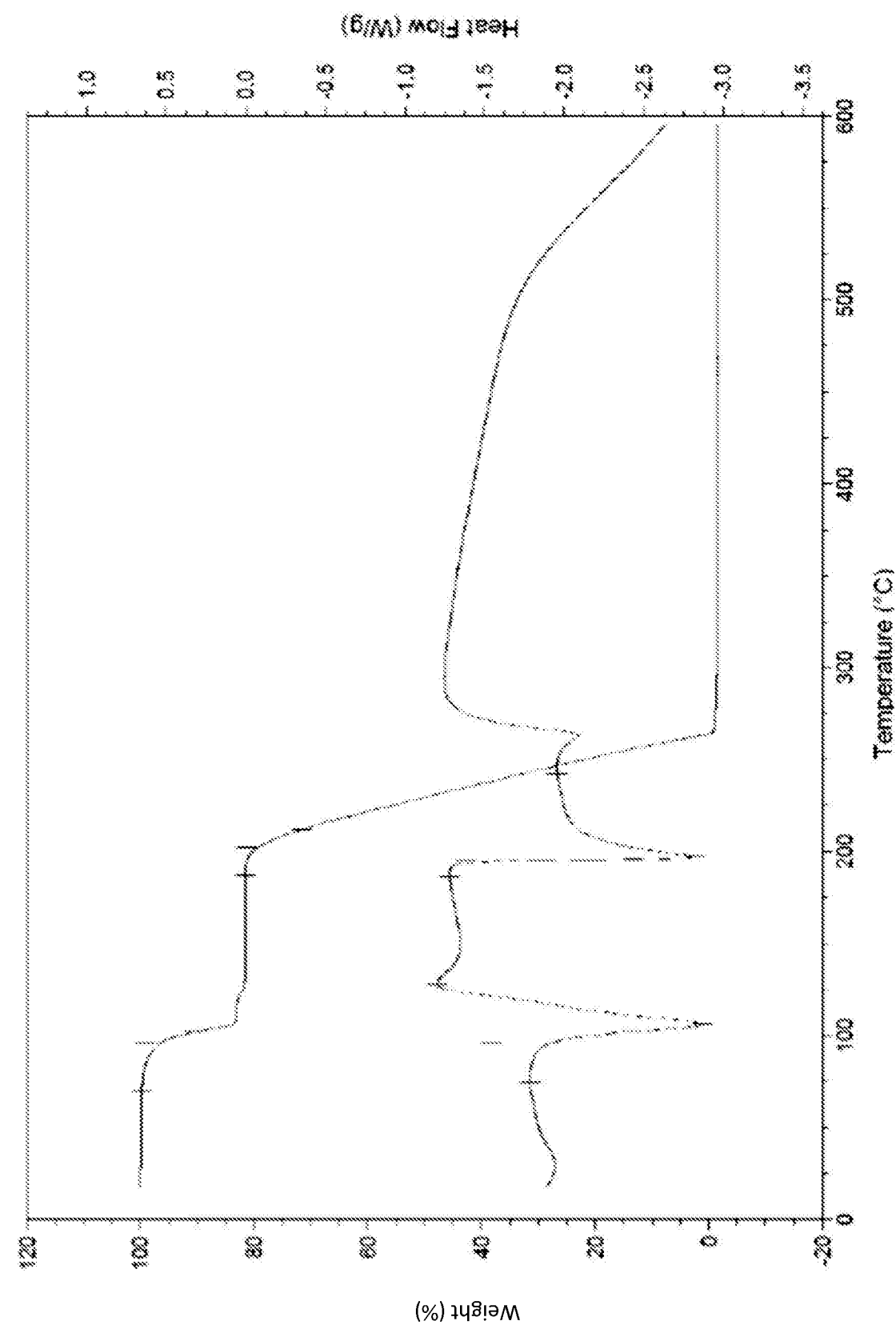
FIG. 15b shows overlaid DSC and TGA thermograms of the ethereal solvate Form D isolated from tert-butyl methyl ether in Example 4 and shows a first weight loss transition at about 95.92° C. which corresponds to about 15 to 16% w/w and was attributed to solvent release (sample contained 14.8% w/w tBME by $^1$H NMR). DSC, Lobe 1: integral −151.4 J/g, onset 98.56° C., peak 106.35° C.; Lobe 2: integral −130.1 J/g, onset 194.82° C., peak 196.82° C.

Form D corresponded to isostructural ethereal solvates of which the XRPD spectra are shown in FIG. 7. Both presented just below integer stoichiometry, viz. 0.8*THF (FIGS. 15a) and 0.8*tBME (FIG. 15b).

Figure 16:
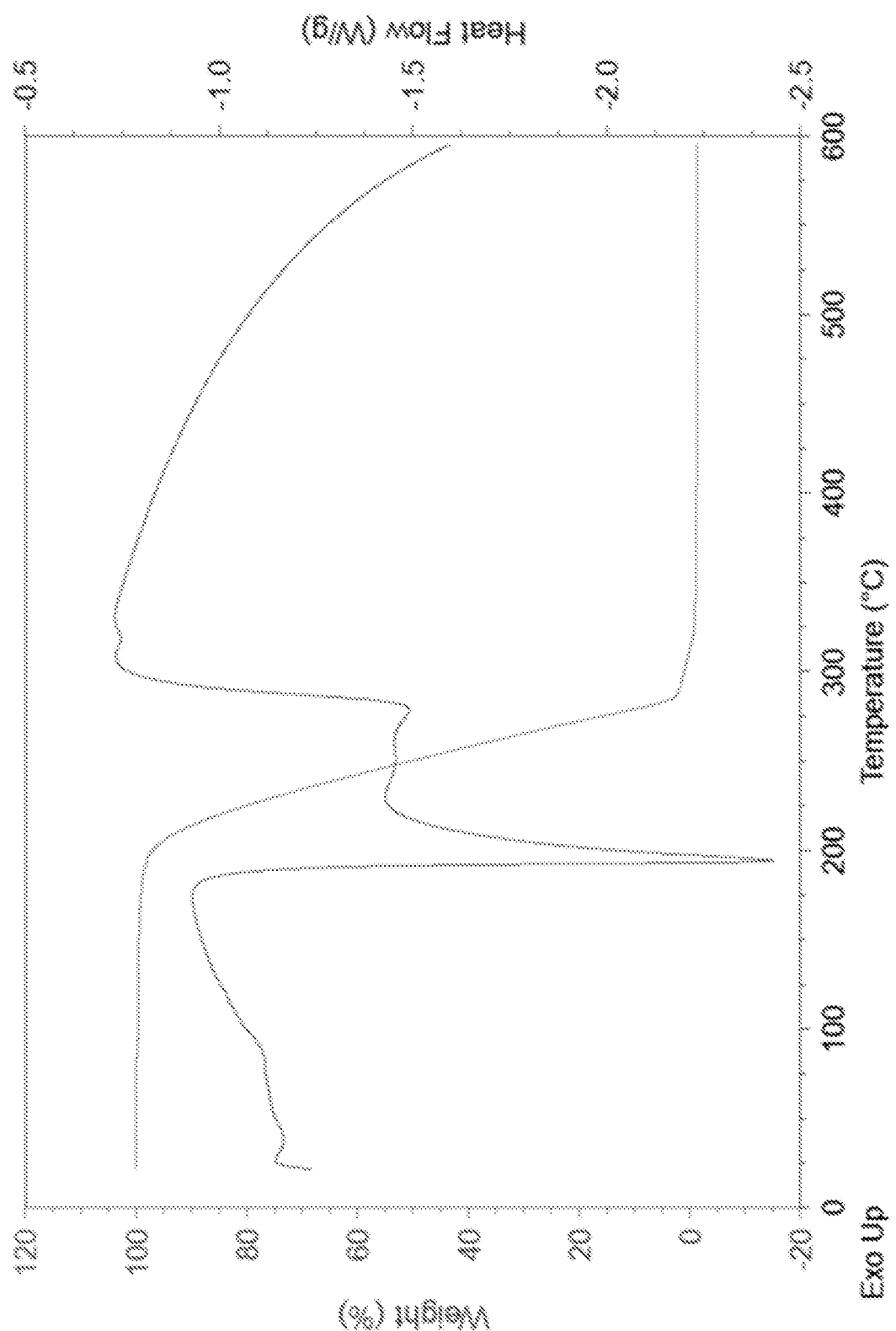
FIG. 16 shows overlaid DSC and TGA thermograms for the partial solvate Form E, isolated from methyl ethyl ketone in Example 4. The sample contained 6.9% w/w MEK by $^1$H NMR. Significant weight loss transitions occur at melting, accompanied by solvent release. DSC, Lobe: integral −102.8 J/g, onset 191.06° C., peak 194.36° C.

Form E isolated from MEK was partially solvated (0.4*MEK). FIG. 16 shows the corresponding TG analysis, and no appreciable weight loss transition was apparent pre-melt event and therefore, bound MEK was only released after significant re-organisation of the host crystal took place (i.e. post-melting to liberate the MEK solvent vapour, accompanied by significant weight losses associated with compound degradation). The XRPD diffractogram is shown in FIG. 8.

Form F was isolated from ethanol and had an XRPD diffractogram shown in FIG. 9. Form E was an anhydrous form and DSC analyses exhibited a similar melt event to Form A, although the diffraction pattern was different; competitive suspension equilibration of an equimolar mixture of Form A and Form F generated only Form A, indicating that Form A is the more stable of the two forms.

Example 5—Anhydrous Suspension Equilibrations of Amorphous Phase at 40° C.

Separate portions of amorphous Compound 1 (ca 50 mg, 1.0 wt.) and the appropriate solvent (1000 µl, 20 vol) were charged to separate vessels and stirred for 7 days at 40° C. After this time the products were cooled, isolated by filtration, washed with recycled maturation solvent, dried under reduced pressure at 40° C. and analysed by XRPD for evidence of alternative crystalline forms. The results are shown in Table 4.

TABLE 4

Phase equilibration in anhydrous solvents at 40° C.

| Solvent | Observation (t = 0) | Observation (t = 72 hours) | Output form |
|---|---|---|---|
| Acetone | Solution | Solution | Disordered E |
| Acetonitrile | Suspension | Suspension | A |
| Anisole | Suspension | Suspension | A |
| Butanol | Solution | Solution | A |
| Tert-butyl methyl ether | Suspension | Suspension | D |
| Cumene | Suspension | Suspension | H |
| Chlorobenzene | Solution | Suspension | A |
| Dichloromethane | Solution | Suspension | Disordered A |
| Ethanol | Solution | Solution | Gum |
| Ethyl acetate | Solution | Feint suspension | A |
| Ethyl formate | Solution | Solution | A |
| Isopropyl acetate | Solution | Feint suspension | A |
| Methyl acetate | Solution | Solution | Disordered A |
| Methyl ethyl ketone | Solution | Solution | E |
| Nitromethane | Suspension | Suspension | A |
| 2-propanol | Solution | Solution | Amorphous |
| Propionitrile | Suspension | Suspension | A |
| Tetrahydrofuran | Solution | Solution | D |
| Toluene | Suspension | Suspension | C |
| Trifluorotoluene | Suspension | Suspension | C |
| water | Suspension | Suspension | B |
| Dichloromethane/heptane (1/1) | Suspension | Suspension | A |
| Acetonitrile/water* (1/19 v/v) | Suspension | Suspension | A + B |

*Purified water was included in the screen

Figure 17:
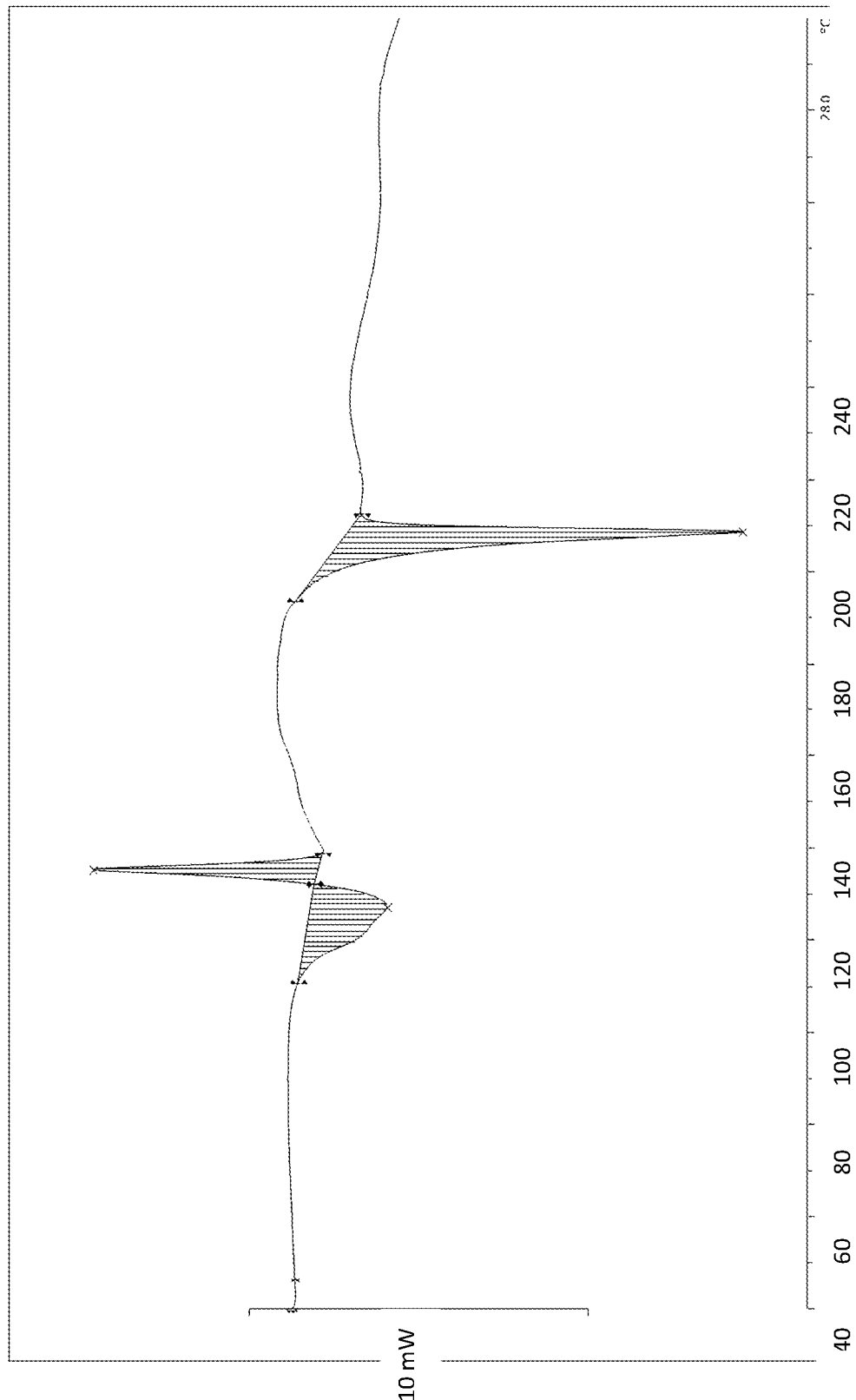
FIG. 17 shows a DSC thermogram of Form H, isolated from cumene in Example 5; temperature range 20-300° C., heating at 10° C. per minute; Lobe 1: integral −26.14 mW° C., onset 94.78° C., endset 111.97° C.; Lobe 2: integral 17.72 mW° C., onset 112.79° C., endset 117.25° C.; Lobe 3: integral −47.09 mW° C., onset 183.96° C., endset 190.15° C.

The same patterns emerged as with the suspension equilibration conducted on the amorphous form at 20° C. (Example 3).
- Form A was the dominant form
- Form B, or a mixture of Form A and Form B were generated when water was present
- Form C was observed from toluene and trifluorotoluene, and were generated
- Form D, an isostructural solvate was observed from the ether solvents: THF and tBME.
- A new disordered form was observed, designated Form H (refer to XRPD shown in FIG. 10) and DSC shown in FIG. 17). Form H was partially solvated and contained 9.0% w/w cumene, equating to ca 0.4*solvate. By DSC, an exotherm event was evident with onset 94° C., which was significantly lower than the boiling point of cumene (152° C.). The endothermic event at 94° C. is an estimated transition temperature from Form H solvate to anhydrous form, followed by an exothermic event, which was attributed to crystallisation.

Example 6—Aqueous Suspension Equilibrations of Amorphous Phase at 20° C.

Separate portions of amorphous Compound 1 (ca 50 mg, 1.0 wt.) and the appropriate solvent (950 µl, 19 vol) and purified water (50 µl) were charged to separate vessels and stirred for 7 to 10 days at 20° C. After this time the products were cooled, isolated by filtration, washed with recycled maturation solvent, dried under reduced pressure at 40° C. and analysed by XRPD for evidence of alternative crystalline forms. The results are shown in Table 5.

TABLE 5

Phase equilibration in aqueous solvents at 20° C.

| Solvent | Observation (t = 0) | Observation (t = 7 days) | Output form |
|---|---|---|---|
| Acetone | Solution | Solution | Amorphous |
| Acetonitrile | Suspension | Suspension | A |
| Anisole | Suspension | Suspension | Disordered H |
| Butanol | Solution | Solution | Gummed |
| Tert-butyl methyl ether | Suspension | Suspension | D |
| Chlorobenzene | Suspension | Suspension | Amorphous |
| Cumene | Suspension | Suspension | B |
| Dichloromethane | Solution | Suspension | B |
| Ethanol | Solution | Solution | Amorphous |
| Ethyl acetate | Solution | Solution | E |
| Ethyl formate | Solution | Solution | Amorphous |
| Isopropyl acetate | Solution | Solution | E |
| Methyl acetate | Solution | Solution | Amorphous |
| Methyl ethyl ketone | Solution | Solution | E |
| Nitromethane | Suspension | Suspension | B |
| 2-propanol | Solution | Solution | Gummed |
| Propionitrile | Solution | Solution | E |
| Tetrahydrofuran | Solution | Solution | D |
| Toluene | Suspension | Suspension | B |
| Trifluorotoluene | Suspension | Suspension | Disordered B |
| water | Suspension | Suspension | B |
| Dichloromethane/heptane (1/1) | Suspension | Suspension | B |
| Acetonitrile/water (1/19 v/v) | Suspension | Suspension | B |

No new forms were observed. Form B was the most prevalent form observed.

Example 7—Further Suspension Equilibrations

Additional suspension equilibration experiments were conducted as follows.

A. Anhydrous Suspension Equilibrations of Form A at 20° C.

Compound 1 Form A, (ca 50 mg, 1.0 wt) and the appropriate solvent (1000 µl, 20 vol) were charged to separate vessels and stirred for 7 days at 20° C. After this time the products were cooled, isolated by filtration, washed with recycled maturation solvent, dried under reduced pressure at 40° C. and analysed by XRPD for evidence of alternative crystalline forms. N.B. water and acetonitrile/water were also included in this study.

The products were consistent with Form A, unless water was present, which promoted the formation of the hydrate Form B In the presence of tBME Form D was generated, from the other ethers THF and 2-MeTHF insufficient sample was recovered for XRPD analyses Therefore, Form A was resilient to prolonged solvent mediated treatments at 20° C. under anhydrous conditions B. Anhydrous Suspension Equilibrations of Form A at 40° C.

Separate portions of Compound 1, Form A (ca 50 mg, 1.0 wt.), and the appropriate solvent (1000 μl, 20 vol.) were charged to separate vessels and stirred for 7 days at 40° C. After this time, the products were cooled, isolated by filtration, washed with recycled maturation solvent, dried under reduced pressure at 40° C. and analysed by XRPD for evidence of alternative crystalline forms. N.B. water was also included in this screen.

All of the products corresponded to Form A, except the product isolated from tBME (Form D), and from THF (Form G; see FIG. 18). The product normally encountered in the presence of THF is Form D.

An experiment was carried out in purified water and unexpectedly generated Form A, no Form B was evident.

C. Aqueous Suspension Equilibrations of Form A at 20° C.

Separate portions of Compound 1, Form A (ca 50 mg, 1.0 wt.), and the appropriate solvent (950 μl, 19 vol) and purified water (50 μl, 1.0 vol) were charged to separate vessels and stirred for 7 to 10 days at 20° C. After this time, the products were cooled, isolated by filtration, washed with recycled maturation solvent, dried under reduced pressure at 40° C. and analysed by XRPD for evidence of alternative crystalline forms.

As expected, the presence of water promoted the conversion of Form A into Form B, the rate of interconversion under these conditions was relatively slow.

In the presence of purified water only, partial conversion into Form B was observed. This finding conflicts with results observed at 40° C. that just generated Form A and suggests that a transition temperature may be present under solvent mediated conditions.

Unusually, Form C was also generated from acetone, anisole, ethanol and 2-propanol. Form C is an anhydrous form, and sometimes occurs in the presence of aromatic solvents (toluene and trifluorotoluene). Competitive suspension equilibration of this form in the presence of Form A was later used to determine which of the forms is the most stable under ambient, anhydrous conditions.

Example 8—Aqueous Surfactant Equilibrations of Form A at Above and Below Critical Micelle Concentration (CMC)

A sample of Form A was micronised using an AS100 spiral jet mill (Alpine) with a ZD9 screw dosing system at a milling gas pressure of 5.0 bar (18° C.) and an injection gas pressure of 6.0 bar (18° C.). Feed rate was 350 g/hr.

D50 and D90 values were measured for the input and output materials using a Beckman Coulter LS™ 13 320 particle size analyser.

Input: D50 35.74 μm, D90 77.74 μm.
Output: D50 1.14 μm, D90 2.44 μm.

Form A and micronised Form A were added to purified water containing the surfactants shown in Table 6, and the mixtures were stirred at 20° C.

TABLE 6

Surfactant media for surfactant equilibration experiments

| Exp | Micronised or non-micronised | Medium |
| --- | --- | --- |
| Control 1 | Non-micronised | Purified water, 5 ml (10 vol) |
| Surf 1 | Non-micronised | Tween ® 80, 5 ml (10 vol, @ 1 mg/ml), in purified water [>CMC] |
| Surf 2 | Non-micronised | Tween ® 20, 5 ml (10 vol, @ 0.5 mg/ml), in purified water [>CMC] |
| Surf 3 | Non-micronised | Span ® 20, 5 ml (10 vol, @ 0.05 mg/ml), in purified water [N/A] |
| Surf 4 | Non-micronised | Tween 80, 5 ml (10 vol, @ 0.01 mg/ml), in purified water [<CMC] |
| Surf 5 | Micronised | Tween ® 80 (10 vol, 0.1 mg/ml [>CMC]), 20° C./8 days |
| Surf 6 | Micronised | Tween ® 80 (10 vol, 0.01 mg/ml [<CMC]), 20° C./8 days |
| Control 2 | Micronised | Purified water 3.3 ml (10 vol) 20° C./8 days |

Sub samples (300 to 500 μl) were withdrawn at the appropriate time points. The mixtures were centrifuged, the clarified supernatant was decanted, and the pellet was oven dried (20° C., 24 h) and analysed by XRPD. Rate of conversion was monitored by measuring the approximate rate of change of the peak areas of selected reflections from each form to compute the consumption of Form A (exhibited strong reflection at ca 7.1° 2-theta, refer 1a) and formation of Form B (exhibited strong reflection at ca 11° 2-theta, refer to FIG. 4). The time taken for complete conversion of Form A into Form B was concluded when Form A was no longer detectable by XRPD. The results are shown in Tables 8 to 11.

TABLE 7

Results for surfactant equilibration of non-micronised Form A - Time point sampling at 20° C.

| Exp | Form A 7.1° 2 Theta 1 h | Form B 11.2° 2 Theta 1 h | Form A 7.1° 2 Theta 3 h | Form B 11.2° 2 Theta 3 h | Form A 7.1° 2 Theta 8 h | Form B 11.2° 2 Theta 8 h | Form A 7.1° 2 Theta 24 h | Form B 11.2° 2 Theta 24 h |
| --- | --- | --- | --- | --- | --- | --- | --- | --- |
| Control 1 | 100% | 0% | 100% | 0% | 100% | 0% | 93% | 7% |
| Surf 1 | 100% | 0% | 100% | 0% | 100% | 0% | 100% | 0% |
| Surf 2 | 100% | 0% | 100% | 0% | 100% | 0% | 100% | 0% |
| Surf 3 | 100% | 0% | 100% | 0% | 100% | 0% | 100% | 0% |
| Surf 4 | 100% | 0% | 100% | 0% | 100% | 0% | 100% | 0% |

TABLE 8

Results for surfactant equilibration of non-micronised Form A - Time point sampling at 40° C.

| Exp | Form A 7.1° 2 Theta 3 h | Form B 11.2° 2 Theta 3 h | Form A 7.1° 2 Theta 24 h | Form B 11.2° 2 Theta 24 h | Form A 7.1° 2 Theta 72 h | Form B 11.2° 2 Theta 72 h | Form A 7.1° 2 Theta 96 h | Form B 11.2° 2 Theta 96 h |
|---|---|---|---|---|---|---|---|---|
| Control 1 | 90% | 10% | 94% | 6% | 79% | 21% | 84% | 16% |
| Surf 1 | 100% | 0% | 100% | 0% | 100% | 0% | 100% | 0% |
| Surf 2 | 100% | 0% | 100% | 0% | 100% | 0% | 100% | 0% |
| Surf 3 | 100% | 0% | 100% | 0% | 100% | 0% | 100% | 0% |
| Surf 4 | 100% | 0% | 100% | 0% | 100% | 0% | 100% | 0% |

TABLE 9

Results for surfactant equilibration of micronised Form A - Time point sampling at 20° C.

| Exp | Form A 7.1° 2 Theta 3 h | Form B 11.2° 2 Theta 3 h | Form A 7.1° 2 Theta 24 h | Form B 11.2° 2 Theta 24 h | Form A 7.1° 2 Theta 48 h | Form B 11.2° 2 Theta 48 h | Form A 7.1° 2 Theta 72 h | Form B 11.2° 2 Theta 72 h |
|---|---|---|---|---|---|---|---|---|
| Surf 5 | 100% | 0% | 100% | 0% | 100% | 0% | 94% | 6% |
| Surf 6 | 100% | 0% | 100% | 0% | 100% | 0% | 63%* | 37%* |
| Control 2 | 100% | 0% | 100% | 0% | 100% | 0% | 96% | 4% |

*Ratio was potentially exacerbated by preferred orientation effects

TABLE 10

Results for surfactant equilibration of micronised Form A - Time point sampling at 40° C.

| Exp | Form A 7.1° 2 Theta 146 h | Form B 11.2° 2 Theta 146 h | Form A 7.1° 2 Theta 167 h | Form B 11.2° 2 Theta 167 h | Form A 7.1° 2 Theta 193 h | Form B 11.2° 2 Theta 193 h |
|---|---|---|---|---|---|---|
| Surf 5 | 0% | 100% | 0% | 100% | 0% | 100% |
| Surf 6 | 2% | 98% | 0% | 100% | 0% | 100% |
| Control 2 | 0% | 100% | 0% | 100% | 0% | 100% |

Definitions

A micelle is an aggregate of surfactant molecules dispersed in a liquid colloid. Micelles form only when the concentration of surfactant is greater than the critical micelle concentration (CMC).

Surf 1: TWEEN® 80 (polysorbate 80; polyoxyethylene sorbitan monooleate) Critical Micellar Concentration (CMC) 13-15 mg/litre [actual concentration used=1 mg/ml, 1000 mg/litre>CMC]

Surf 2: TWEEN® 20 (polysorbate 20; polyethylene glycol sorbitan monolaurate) 20 Critical Micellar Concentration (CMC) ca 61 mg/litre [actual concentration used=0.5 mg/ml, 500 mg/litre>CMC]

Surf 3: SPAN® 20 (sorbitan monolaurate) no CMC in water, too hydrophobic and yet still exerted an inhibitory effect on the form conversion Surf 4: TWEEN® 80 Critical Micellar Concentration (CMC) 13-15 mg/litre [actual concentration used=0.01 mg/ml, 10 mg/litre<CMC]

TWEEN® surfactants are soluble in water and SPAN® surfactants are oil soluble and not able to form micelles in water. SPAN® will be biphasic, and will therefore exhibit the co-existence of aqueous and surfactant phases.

Surf 5: TWEEN® 80 Critical Micellar Concentration (CMC) 13-15 mg/litre [actual concentration used=0.1 mg/ml, 100 mg/litre>CMC]

Surf 6: TWEEN® 80 Critical Micellar Concentration (CMC) 13-15 mg/litre [actual concentration used=0.01 mg/ml, 10 mg/litre<CMC].

As shown in Tables 8 and 9:

The reflections that corresponded to Form B were only detectable in the control experiment, performed in purified water after 24 at 20° C. and increased after +96 h at 40° C.

The conversion of Form A into Form B had not taken place in the experiments containing the three surfactants at 20° C. over 24 h period and +96 h at 40° C. Therefore, the use of Tween® 80, 5 ml (10 vol, @ 1 mg/ml) in the aqueous formulation of Form A does not appear to accelerate the conversion of Form A into Form B, and instead, appears to exert the opposite effect.

An additional experiment was performed using aqueous Tween® 80 solution (0.01 mg/ml, <CMC) (Surf 4). The conversion of Form A into Form B had not taken place under these conditions after 24 at 20° C. or after +96 h at 40° C.

It therefore appears that the presence of surfactant (TWEEN® 80) exerted a inhibitory effect on the rate of form conversion of Form A into Form B, even when present at sub CMC concentrations; thus storage of Form A in pre-made composition should be stable for 120 h under 20 to 40° C. storage conditions.

As shown in Tables 10 and 11:
The reflections that corresponded to Form B were detectable in all experiments after 72 h at 20° C. (>CMC, <CMC, purified water), and increased after 146 h at 20° C.
The conversion of Form A into Form B had not taken place in the experiments containing the surfactants at 20° C. over a 24 h period; however, micronised Form A (particle size 2 μm) had started to convert to Form B after 48 h and had almost completely converted into Form B after 146 h, under the conditions investigated
Therefore, micronised Form A is susceptible to form change, and the form change proceeds to completion with or without surfactant at 20° C. after 146 h.

Example 9—Competitive Suspension Equilibrations

Form A of Compound 1 and the appropriate other form(s) of Compound 1 were suspended in acetonitrile (20 vol). The white suspension was stirred at 40° C. for 7 days. When completed, the products were isolated, oven dried and analysed by XRPD. The results are shown in Table 11.

TABLE 11

Results of Competitive suspension equilibration

| Solvent (20 vol) | Temp (° C.) | Composite input form (XRPD) | Output form (XRPD) | Yield % |
|---|---|---|---|---|
| Acetonitrile | 40 | Form A | Form A | 79% |
| Acetonitrile | 40 | Form A + Form B (1/1 w/w) | Form A | 62% |
| Acetonitrile | 40 | Form A + Form C (1/1 w/w) | Form A | 78% |
| Acetonitrile | 40 | Form A + Form D (1/1 w/w) | Form A | 66% |
| Acetonitrile | 40 | Form A + Form E (1/1 w/w) | Form A | 88% |
| Acetonitrile | 20 | Form A + Form F (1/1 w/w) | Form A | 74% |
| Acetonitrile | 40 | Form A + Form F (19/1 w/w) | Form A | 73% |
| Acetonitrile | 40 | Form A + Form G (1/1 w/w) | Form A | 74% |
| Acetonitrile | 40 | Form A + Form E (1/9 w/w) | Form A | 82% |
| Acetonitrile | 40 | Form A + Form A + B (1/1 w/w) | Form A | 73% |
| Acetonitrile | 40 | Form A + Form B + Form C + Form D + Form E + Form G + Form H + Form A + B (eq. w/w) | Form A | 72% |
| Acetonitrile | 20 | Form A + Form F (1/1 w/w) | Form A | 74% |

The results presented in Table 11 show that:
When stirred under anhydrous conditions at 40° C., Form A and the appropriate form(s) converted into Form A.
Under anhydrous conditions the mixture of Form A and Form B (hydrate) converted into Form A.
Composite of all forms were stirred at 40° C., and converted to Form A.
When stirred under anhydrous conditions at 20° C. and 40° C., composite Form A+F, both underwent conversion into a form consistent with authentic Form A
Equimolar amounts of Form F and Form A were competitively suspension equilibrated in anhydrous acetonitrile to determine the fates of the two originators. The isolated product was consistent with authentic Form A, and no traces of Form F were evident in the diffraction pattern, which served to confirm the conversion of Form F into Form A under these conditions.
Therefore, under production conditions, forms of Compound 1 other than Form A should be metastable with respect to Form A and should inevitably convert into single phase A.

Example 10—Crystallisation of Form A via Diffusion

Solutions of Compound 1, Form A (ca 50 mg, 1.0 wt) were prepared in the appropriate, less volatile solvent, and clarified through a 2 μm PTFE membrane. The saturated solutions were then transferred into separate vessels and each vessel was placed within a larger vessel. Volatile precipitant solvent was added to the larger vessel to form a moat around the outside of the smaller vessel, and the large vessel was then capped. The vessel set-ups were allowed to stand undisturbed for several days at 18 to 23° C. During which time, the volatile solvent diffused across into the smaller vessel until the solvent moat was depleted and the solvent composition of the solution was sufficiently saturated to promote crystallisation of ET003861. The isolated products were collected by filtration and oven dried at 40° C. under reduced pressure for ca 20 h.
Combinations of:
ethanol (less volatile) and dichloromethane (more volatile);
ethanol (less volatile) and tert-butylmethyl ether (more volatile);
did not result in the formation of crystals.
Using the combination of ethanol (less volatile) and pentane (more volatile), after eight days needles had grown from a single point on the vial wall. The solid was isolated by centrifugation, the mother liquors were decanted and the product was dried overnight at 40° C. The sample was analysed by $^1$H NMR spectroscopy and the XRPD and was shown to be Compound 1 Form A crystalline polymorph.

Example 11—Crystallisation Via Heat-Up Cool-Down

Nineteen portions of amorphous Compound 1 (ca 70 mg, 1.0 wt.) were charged to separate scintillation vials. Aliquots of the relevant solvent (Solvent A of Table 12) were charged to each vial at temperature (ca 70° C.) until full dissolution occurred. The solutions were cooled, and allowed to stand undisturbed at sub-ambient temperature to promote crystallisation. The products were isolated by filtration, washed with recycled maturation solvent, dried under reduced pressure at 40° C. and analysed by flat plate XRPD for evidence of crystallisation. The results are shown in Table 10.

TABLE 12

Crystallisation via heat-up cool-down

| Solvent A | Amount Solvent A (μl) | Amount of solvent B (isopropanol) (μl) | Yield (%) | Output form |
|---|---|---|---|---|
| Acetone | 410 | — | 38 | A |
| Anisole | 2100 | 40 | 39 | E |
| Butanol | 400 | — | 48 | A |
| Tert-butyl methyl ether | 2100 | 60 | 65 | D |
| Cumene | 2100 | 100 | — | No solid formed |
| Chlorobenzene | 2100 | 60 | — | No solid formed |
| Ethanol | 300 | — | 49 | A |
| Ethyl acetate | 760 | — | 32 | E |
| Ethyl formate | 1230 | — | 56 | A |
| Isopropyl acetate | 1110 | — | 34 | A |
| Methyl acetate | 760 | — | 49 | A |
| Methyl ethyl ketone | 320 | — | 59 | E |
| Nitromethane | 2100 | 40 | 61 | A |
| 2-propanol | 430 | — | 41 | A |
| Propionitrile | 850 | — | 52 | A |
| Toluene | 2100 | 100 | — | No solid formed |
| Trifluorotoluene | 2100 | 200 | — | No solid formed |
| water | 2100 | 1340 | 87 | B |
| Tetrahydrofuran | 410 | — | 56 | D |

TABLE 12-continued

Crystallisation via heat-up cool-down

| Solvent A | Amount Solvent A (μl) | Amount of solvent B (isopropanol) (μl) | Yield (%) | Output form |
|---|---|---|---|---|
| Dichloromethane | 3500 | — | 75 | Disordered |
| Tetrahydrofuran | 600 | — | 71 | Form D hemi THF solvate |
| Dichloromethane/heptane (1/1 v/v) | 2400 | — | — | Amorphous |
| Acetonitrile | 1000 | — | 69 | A |
| Acetonitrile/water (4/1 v/v) | 1000 | — | 69 | B |

No new crystalline forms were identified.

Form A was the dominant form from this screen and the screen provides alternative crystallisation conditions that generate Form A.

Therefore, alternative solvent conditions or future development of heat-up/cool down crystallisation investigations should include ethanol at ca 5 vol and methyl acetate at ca 11 vol. The currently preferred crystallisation solvent is ethyl acetate (see Example 12).

Example 12—Crystallisation of Form A from Ethyl Acetate

The process is set out below
1. Charge Compound 1 (1.00 wt, 1.0 eq) to a vessel (total volume at this step 1.0)
2. Charge Ethyl acetate (20 vol, 18 wt) to the vessel. (total volume at this step
3. Heat the mixture to 55 to 65° C., suitably 60° C.
4. Stir the mixture at 55 to 65° C., preferably 60° C. for at least 10 minutes to give a hazy solution
5. Cool down the mixture to 45 to 50° C., preferably 47° C., over 30 min to 1 hour. Once at temperature proceed to step 6 without delay.
6. Clarify the mixture through 1 μm filter at 45 to 50° C.
7. Perform a line rinse with ethyl acetate, (2 vol, 1.8 wt) (total volume at this step 23.0 but the volume of ethyl acetate can be increased if needed as it will be distilled out next).
8. Distil to about 10 vol under vacuum at 40 to 50° C., preferably 45° C. Precipitation may be observed as this volume is reached. (total volume after this step is about 10.0)
9. Cool to 35 to 40° C., preferably 37° C. over 30 to 60 minutes. Age for up to 2 h and once crystallisation is observed proceed to step 10.
10. Age the slurry at 35 to 40° C. for 1 to 2 h.
11. (optional) Sample the reaction mixture and filter for analysis by XRPD to ensure that the crystalline form produced is Form A.
12. Cool the vessel contents to 20 to 25° C., targeting 23° C., over 2 to 3 hours, at a constant rate.
13. Age the mixture at 20 to 25° C., targeting 23° C., for 4 to 6 hours, target 5 hours.
14. Charge clarified n-Heptane (5 vol, 3.4 wt) over 1 to 2 hours at 20 to 25° C., targeting 23° C., target 1.5 h.
15. Age the mixture at 20 to 25° C., targeting 23° C., for 30 min to 60 min.
16. Cool the vessel contents to 0 to 5° C., targeting 2.5° C., over 1 to 2 hours, at a constant rate targeting 1.5 h
17. Age the mixture at to 0 to 5° C., targeting 2.5° C., for 2 to 4 hours, target 3 hours.
18. Filter the reaction mixture using 20 μm cloth. Liquors can be recirculated if the material passes the filter. Filter cake volume: 2 vol
19. Wash the filter cake with a mixture of clarified Ethyl acetate (1.3 vol, 1.17 wt) and clarified n-Heptane (0.7 vol, 0.48 wt) at 0 to 5° C.
20. Dry the filter cake at 20 to 25° C., temperature can be increased up to 40° C. if required. 13, 14 Can be dried on filter without heat easily.
21. Determine the solvent content and If the Ethyl acetate content is ≤0.3% w/w and n-Heptane content is ≤0.3% w/w proceed to step 22. If either of the solvents are above the specified values continue the drying and resample after at least 4 h.
22. Discharge the product Example 13—Further Characterisation of Form B Two separate batches of the Form B hydrate polymorph of Compound 1 were analysed by XRPD, DSC, TGA, FT-IR and SEM. The batches exhibited different dehydration activity by DSC and TGA (see FIGS. 21 and 22). The first batch presented a unimodal dehydration event and was designated Form B (I), whilst the second batch featured bimodal dehydration and was designated Form B (II). The XRPD spectra are shown in FIGS. 23a and 23b, from which it can be seen that the two forms are isostructural and cannot be distinguished by XRPD. The angles, d values and intensities are shown in Table 2 above.

Assuming that the inconsistencies between the dehydration behaviours of the two batches were attributed to different locations and bindings of their water occupancies, both were examined after 10 tonne compaction, to determine if their dehydration features were conserved or altered after the application of equal pressure treatments.

Conservation of the dehydration features would imply less space was available in what remained of the lattice after compaction, whilst a change to the basic topography of the dehydration feature by DSC, may indicate a shattering of adjacent crystallites owing to the application of high compressive force, these smaller crystals would presumably be able to occupy the spaces in the lattice remnants.

i. Compaction of Forms B(I) and B(II)

A finely divided specimen of Form B(II) was applied evenly to the smooth surface of the lower sample anvil that was located inside the compression cell apparatus. A second smoothed face anvil was placed above the first and the sample was pressed into place using finger pressure. The sealed sample cell was then evacuated under house vacuum pressure for at least 5 minutes. An axial load of ca 10 metric tonnes was applied to the upper anvil and the specimen was maintained under a state of unilateral compression for at least 15 minutes. After which time, the apparatus was dismantled and the product was retrieved from the sample holder and analysed to determine if any phase modifications had taken place.

No significant changes were observed by FT-IR after compression, only amplification of signals between 3000 to 3600 cm$^{-1}$.

Figure 24:
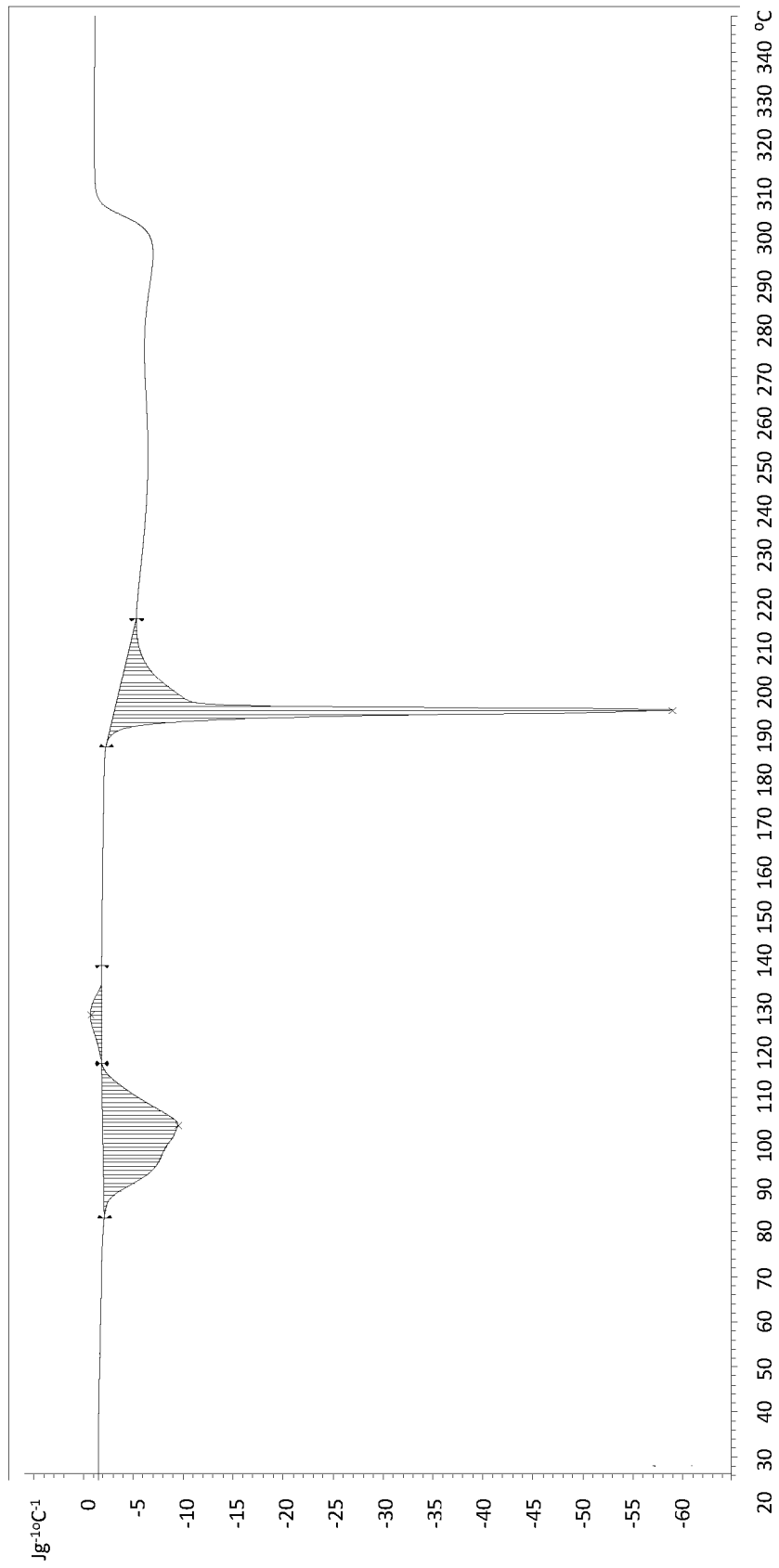
FIG. 24 is a DSC plot for Form B(II) after compression for 20 min under 10 tonnes (heating over 20-350° C. at a rate of 5° C. per min); note the reversion into a single dehydration lobe showing that the sample has converted to Form B(I). Lobe 1: integral −127.53 J/g, onset 87.12° C., peak 103.67° C., endset 114.36° C.; Lobe 2: integral 11.64 J/g, onset 118.97° C., peak 128.08° C., endset 134.72° C.; Lobe 3: integral −168.37 J/g, onset 193.86° C., peak 195.75° C., endset 196.80° C.

After compression, the DSC profile exhibited a single, broad dehydration event instead of the two overlapping bimodal events. In addition, an increase in dehydration temperature was observed post compression treatment (onset value increased from 75.2° C. to 87.1° C. as shown in FIGS. 21b and 24. A higher dehydration temperature (onset value of 107.2° C.) was also identified in the DSC profile of Form B(I)—see FIG. 21*a*. Furthermore, the compressed material was more disordered and exhibited a decrease in crystallinity, by XRPD, the degree of crystallinity after compression decreased from 87.2% to 80.3%, by computation of approximate Gaussian peak area using the following formula:

$$\% \text{ Crystallinity} = 100 - \% \text{ amorphous} = 100 - \left[\left(\frac{\text{Global area} - \text{reduced area}}{\text{global area}}\right) \times 100\right]$$

Lowered intensity and broadening of the peak reflections can be attributed to decreases in the crystallite size. Possible explanation for these observations may be an alteration to the water occupancy; the water is more labile prior to compression. Post compression treatment, Form B(II) did not exhibit significant differences by XRPD or FT-IR but was distinguishable by DSC. Therefore, the two forms are assumed to be related by isostructural pseudopolymorphism, differing only slightly in the orientation and location of their constituent water molecules. Due to the increase in dehydration temperature post compression, it can be assumed that Form B(II) is the less stable hydrate form and is driven towards the more stable hydrate form Form B (I) when compacted. Form B (I) was unchanged after the same treatment.

Moreover, dehydration of lobe I present in Form B (II) occurred at a lower onset temperature than dehydration lobe (I) in Form B (I), indicating that Form B (II) from the production batch was the less stable hydrate form and is driven towards the more stable hydrate form, Form B (I), when high compressive force is applied.

ii. Thermocycling of Forms B(I) and B(II)

Samples of Compound 1, Form A, Form B(I) and Form B(II) were charged to separate Crystal 16 blank, glass vials and purified water (1 ml, 10.0 vol) was added each vial. Each vial underwent thermocycling from −10 to +10° C. at a ramp rate of ±0.5° C./minute, over 75 h.

The control, micronised Form A did not change by XRPD or DSC after thermocycling at a constant amplitude cycle −10 to +10 to −10° C. etc., at a rate of ±0.5° C./minute indicating that Form A is stable to this temperature range.

Unimodal Form B(I) batch was also unchanged by XRPD and DSC with the same indication that Form B unimodal is stable to this temperature range.

Bimodal Form B(II) had no Form A detected by XRPD after the thermocycling for 75 h. This suggests that the low level of Form A, present in the batch (ca 1.1% w/w), had not increased when subjected to thermocycling at a constant amplitude cycle −10 to +10 to −10° C. etc., and may have reverted back into Form B (the levels measured were small). In addition, a change was observed by DSC where it shows that the bimodal event has almost all converted to the unimodal event observed in Form B(I). This suggests that the unimodal Form B(I) is the more stable of the two Form B states under cold conditions, and therefore, unimodal Form B is thermodynamically favoured.

iii. Suspension Equilibration of Form B(II) in Acetonitrile/Water

To further investigate the stability hierarchy of Form B (I) and Form B (II), an equal portion of both Form B (I) and Form B (II) were competitively slurry ripened in 4 to 1 MeCN/Water (w/w) for 3 days. The resulting solid was confirmed by DSC to be Form B (I) which indicates that Form B unimodal is the more stable of the two.

One portion of Form B(II) (1.06 g) was charged with 4 to 1 v/v acetonitrile/water (15 vol, 15 ml). This was stirred at room temperature with a flow of nitrogen. The mixture was subsampled at t=4 h and t=23 h. The subsamples were centrifuged down (13400 rpm for 15 min), supernatants were removed and dried overnight in oven at 40° C. under reduced pressure.

Figure 25:
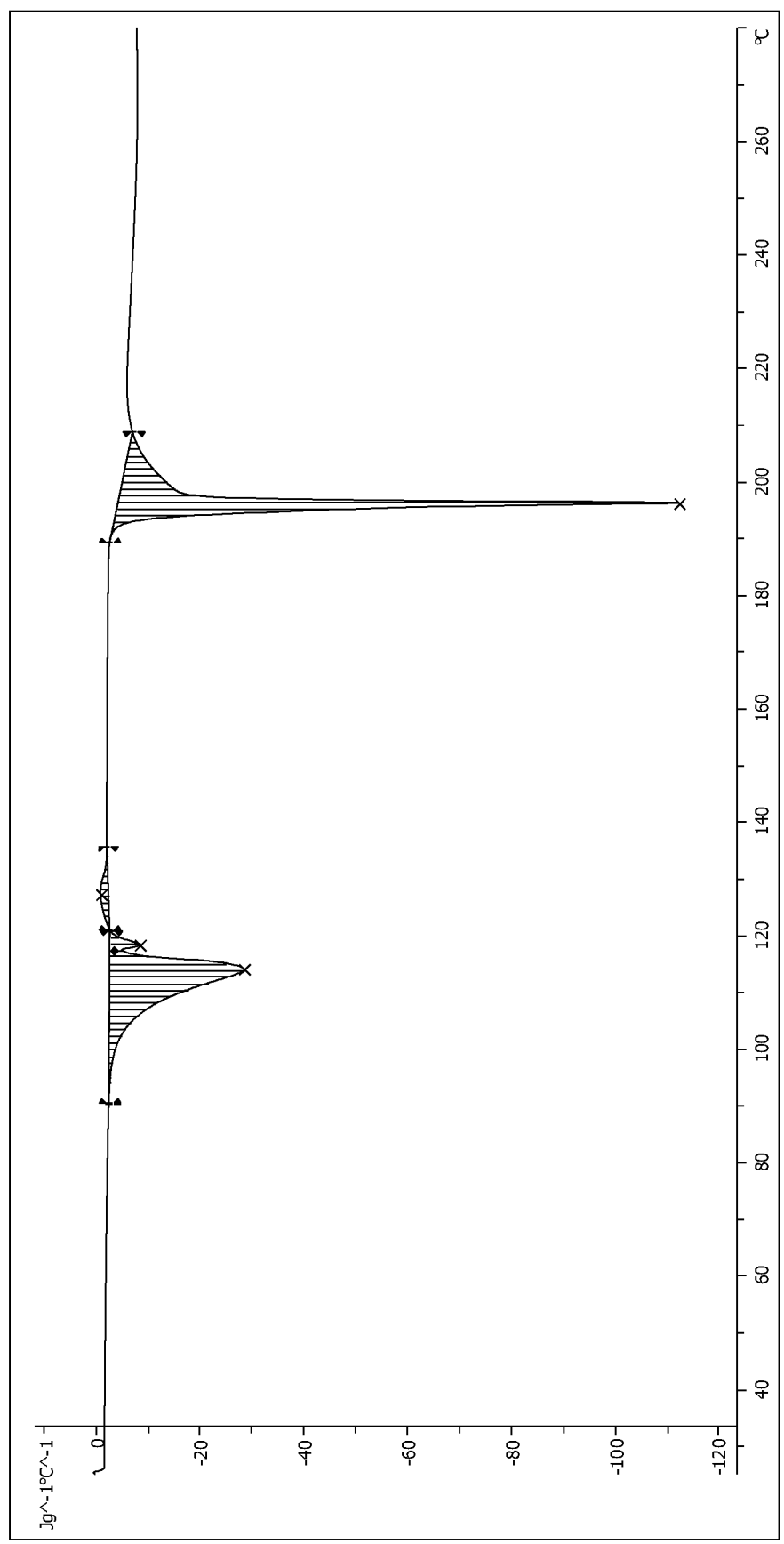
FIG. 25 is a DSC plot over temperature range 25-280° C.; heating at 5° C. per minute for Form B(II) after suspension equilibration in acetonitrile/water (4 to 1 v/v) for 23 hours showing that the sample has converted to Form B(I). Lobe 1: integral −189.83 J/g, onset 106.25° C., peak 113.92° C., endset 116.65° C.; Lobe 2: integral −9.99 J/g, onset 117.12° C., peak 118.25° C., endset 120.00° C.; Lobe 3 integral 11.82 J/g, onset 120.98° C., peak 127.25° C., endset 132.87° C.; Lobe 4: integral −239.87 J/g, onset 194.78° C., peak 196.25° C., endset 197.08° C.

Stirring Form B(II) in 4 to 1 v/v acetonitrile/water resulted in the production of Form B(I) at time points t=4 h and t=23 h. This was confirmed by DSC (see FIG. 25) and XRPD and indicates that Form B unimodal is the more stable of the two forms. The DSC spectrum did contain an unusual event with an onset of 117.12° C. This was attributed to shock release of superheated water over a narrow temperature range and was thought to be related to sample non-homogeneity or to thermal contact in the DSC crucible, rather than being linked to polymorphism.

As part of the Form B investigations, miscellaneous samples derived from the polymorph screen were re-examined. The samples were originally isolated from different originator solvents and conditions and their forms were analysed by XRPD and DSC to determine if Form B (II) was present. Only the unimodal Form B dehydration event was observed by DSC.

iv. Suspension Equilibration of Form B(II) in Purified Water

This experiment was carried out in order to investigate whether Form B(II) is converted to Form B(I) on stirring in purified water over a 20 hour period.

One portion of Form B(II) (1.0 g) was charged with purified water (15 vol, 15 ml). This was stirred at room temperature with a flow of nitrogen for 20 h. The mixture was subsampled at t=2 h and t=20 h. The subsampled mixture was centrifuged down (13400 rpm for 15 min) and supernatant was removed. The remaining solid was dried (at t=3 days) in the oven under reduced pressure at 40° C. overnight. The dried white solid (A0903-184-C1, 0.84 g, 83% yield not corr.). The subsamples and final white solid were analysed by XRPD and DSC and the results for the subsamples are shown in FIGS. 26*a*, 26*b*, 26*c* and 26*d*. The result for the sample at 3 days are not shown as these are the same as the subsample taken at 20 hours.

Figure 26A:
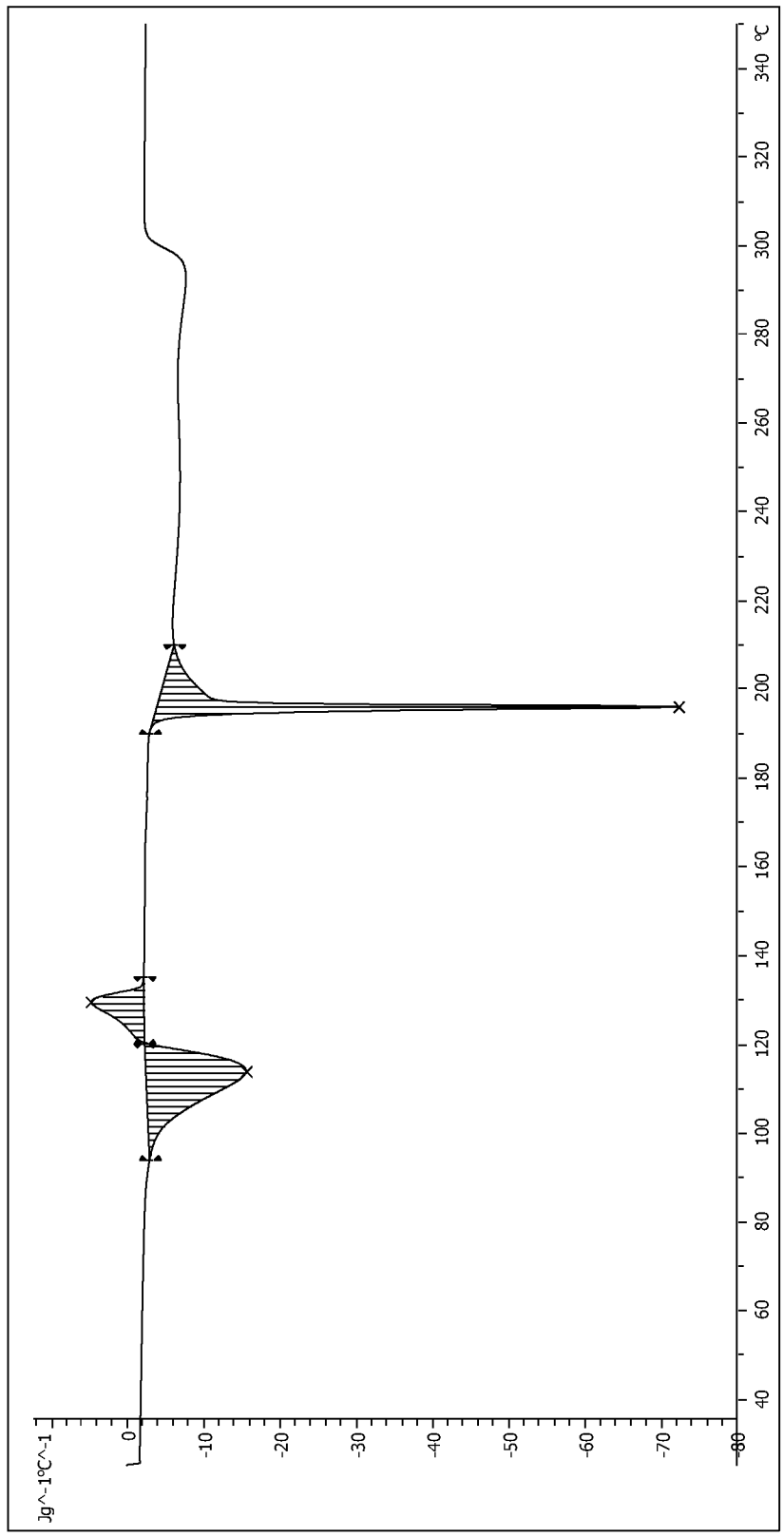
FIG. 26a is a DSC plot over temperature range 25-350° C.; heating at 5° C. per minute for Form B(II) after suspension equilibration in purified water for 2 hours showing that the sample has converted to Form B(I). Lobe 1: integral −154.53 J/g, onset 101.15° C., peak 113.92° C., endset 120.00° C.; Lobe 2: integral 46.14 J/g, onset 120.27° C., peak 129.42° C., endset 132.79° C.; Lobe 3: integral −144.408° C., onset 194.51° C., peak 195.92° C., endset 196.80° C.
Figure 26B:
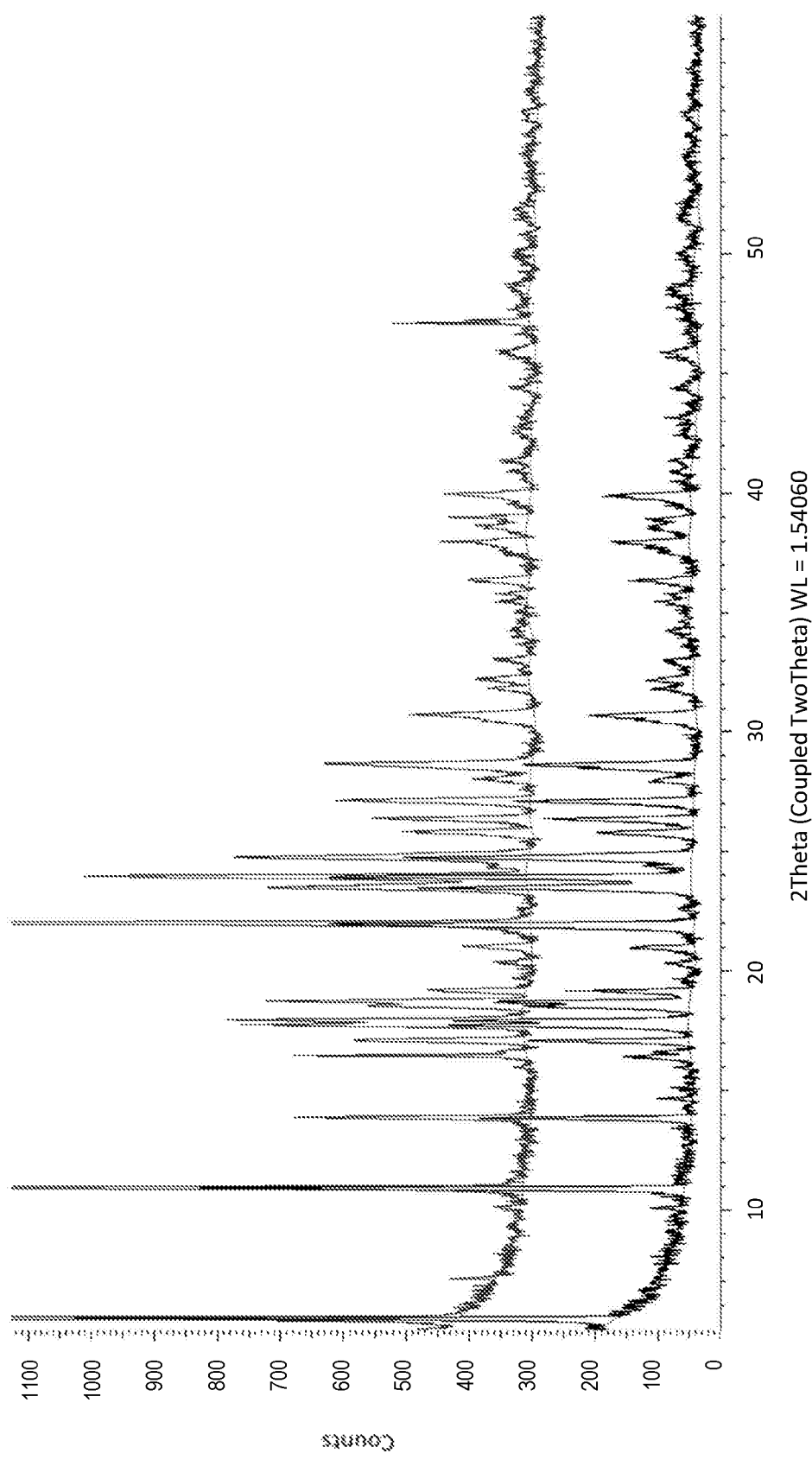
FIG. 26b is an XRPD plot of Form B(II) after suspension equilibration for 2 hours in purified water showing that the sample is still Form B; upper trace: input material; lower trace: output material.

After 2 hours suspension of Form B(II) in purified water, Form A was not detected by XRPD (FIG. 26*b*) and only the unimodal event was observed by DSC (FIG. 26*a*).

Figure 26C:
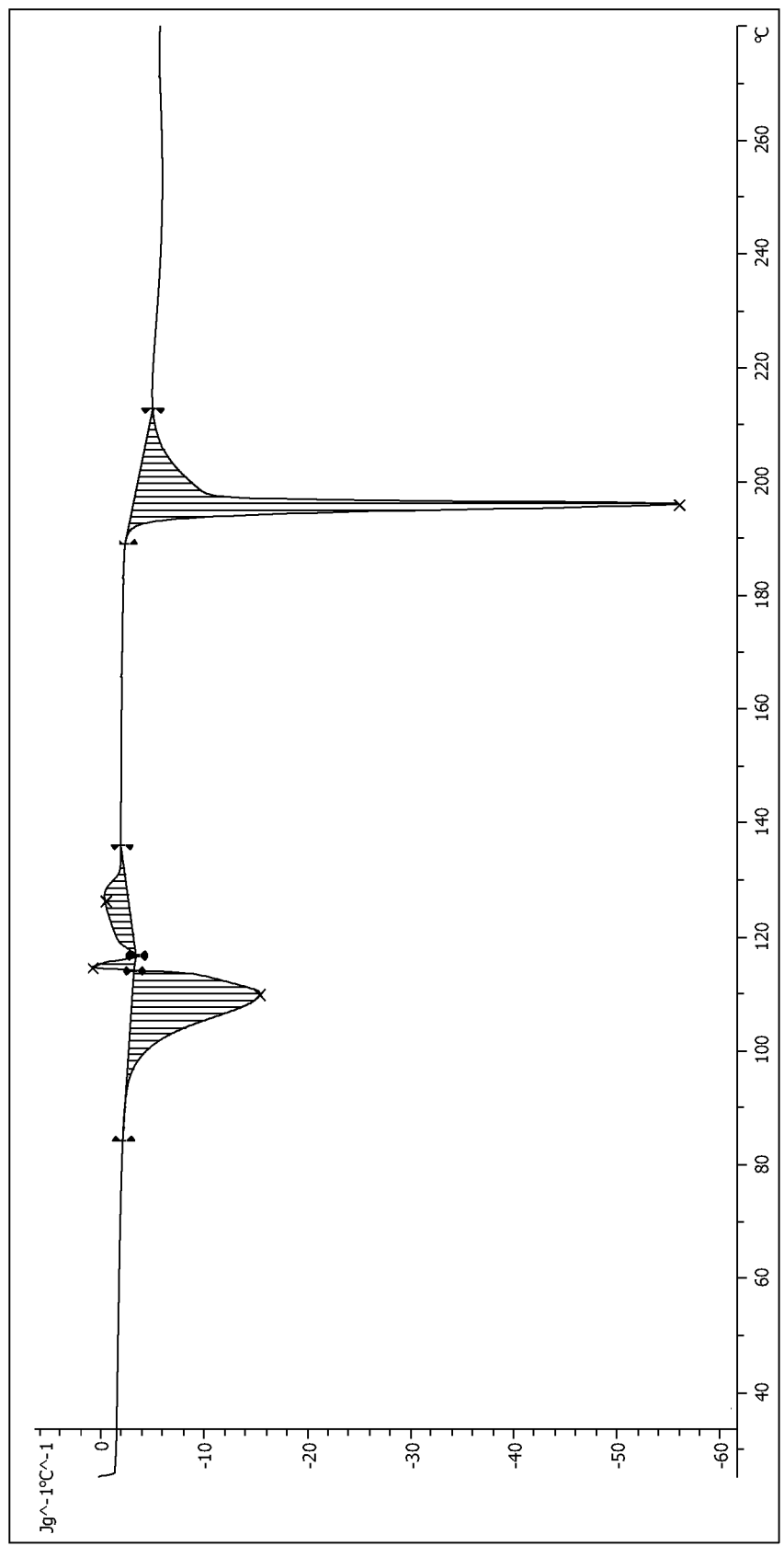
FIG. 26c is a DSC plot over temperature range 25-280° C.; heating at 5° C. per minute for Form B(II) after suspension equilibration in purified water for 200 hours showing that the sample has converted to Form B(I). Lobe 1: integral −109.07 J/g; onset 100.76° C., peak 109.92° C., endset 114.05° C.; Lobe 2 integral 5.54 J/g, onset 114.05° C., peak 114.58° C., endset 116.23° C.; Lobe 3: integral 25.08 J/g, onset 116.86° C., peak 126.25° C., endset 131.82° C.; Lobe 4: Integral −147.30 J/g, onset 193.90° C., peak 195.92° C., endset 197.01° C.
Figure 26D:
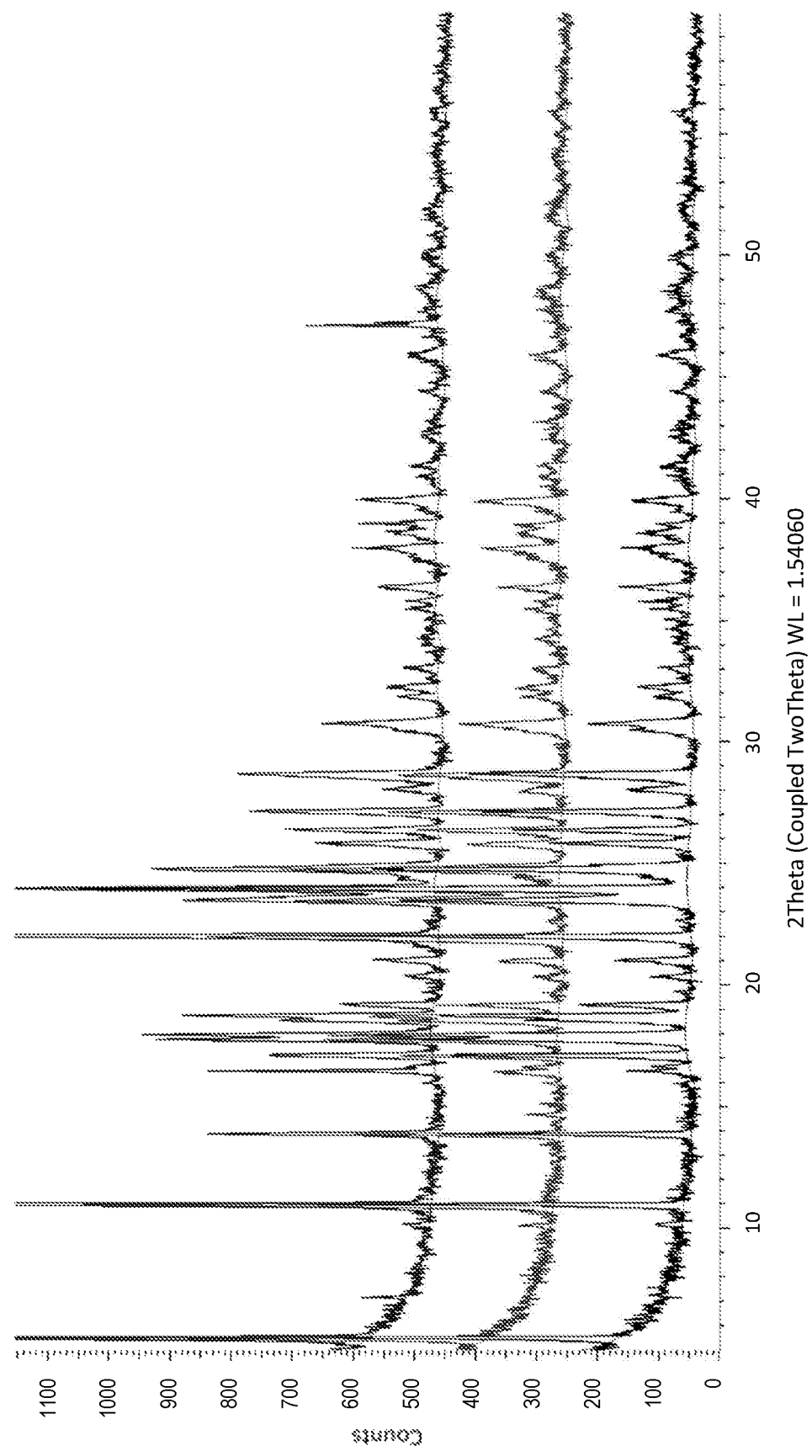
FIG. 26d XRPD plot of Form B(II) after suspension equilibration for 20 hours in purified water showing that the sample still has crystalline Form B; upper trace: input material; middle trace sample after 2 hours in purified water; lower trace: output material.

After 20 hours and three days, the same was observed, although two exothermic events were observed by DSC (see FIG. 26*c* for DSC after 20 hours). This will be investigated.

To summarise, the Form B hydrate polymorph of Compound 1 is capable of adopting two pseudopolymorphic forms, Form B(I) and Form B(II). The results of the experiments described above indicate that the unimodal Form B(I) is the more thermodynamically stable of the two forms.

Example 14—Conversion of Compound 1 Form A (Anhydrous) into Form B (Monohydrate)

Compound 1 Form A was recrystallised from 4:1 acetonitrile:water to give the monohydrate Form B. Unimodal Form B was generated (225.0 $g_{corr}$, 85.7% yield). There was no bimodal Form B generated during the procedure. The product may be micronised if required using, for example, an air jet mill.

In the event that the product contains Form A or Form B(II) is produced, pure form B1 can be obtained by stirring the product in purified water (about 20 volumes) at about 20° C. overnight.

Compound 1 (250.06 g) was charged to flask. 4:1 acetonitrile:water (10V, 2.5 L) was filtered through a glass fibre filter then charged to the flask. The white slurry was heated to reflux (77° C. internal) over 1 hour, with dissolution occurring at an internal temperature of approx. 55° C. The slurry was refluxed over a further 15 minutes to ensure complete dissolution. The solution was then allowed to gradually cool to 15 to 25° C. while stirring (111 rpm) overnight. After overnight stirring, fine white precipitation was observed that was slow to sediment. DSC and XRPD analysis confirmed unimodal Form B had formed. The white slurry was cooled to 0-5° C. and aged for two hours. The slurry was filtered under vacuum and dried on the filter under nitrogen for 72 hours to give the product (225.0 $g_{corr}$, 85.7% yield). DSC and XRPD before and after drying showed the product remained as unimodal Form B. Water content by KF analysis was 4.89% w/w (4.74% w/w expected as monohydrate Form B). $^1$H NMR analysis indicated 0.02% w/w residual acetonitrile.

A sample of the product from the crystallisation was micronised using an AS100 spiral jet mill (Alpine) at a milling gas pressure of 2.5 bar (18° C.) and an injection gas pressure of 3.5 bar (18° C.). $d_{90}$<5 μm. An input of 225 g returned 207 g of material, a recovery of 92%.

D50 and D90 values were measured for the output materials using a Beckman Coulter LS™ 13 320 particle size analyser.

Output: D50 1.65 μm, D90 3.82 μm.

Chemical purity analysis by HPLC was performed before and after micronisation. No loss of purity was observed. The main difference pre- and post-micronisation was a reduction in the water content from 4.8 to 4.1% w/w.

Figure 31:
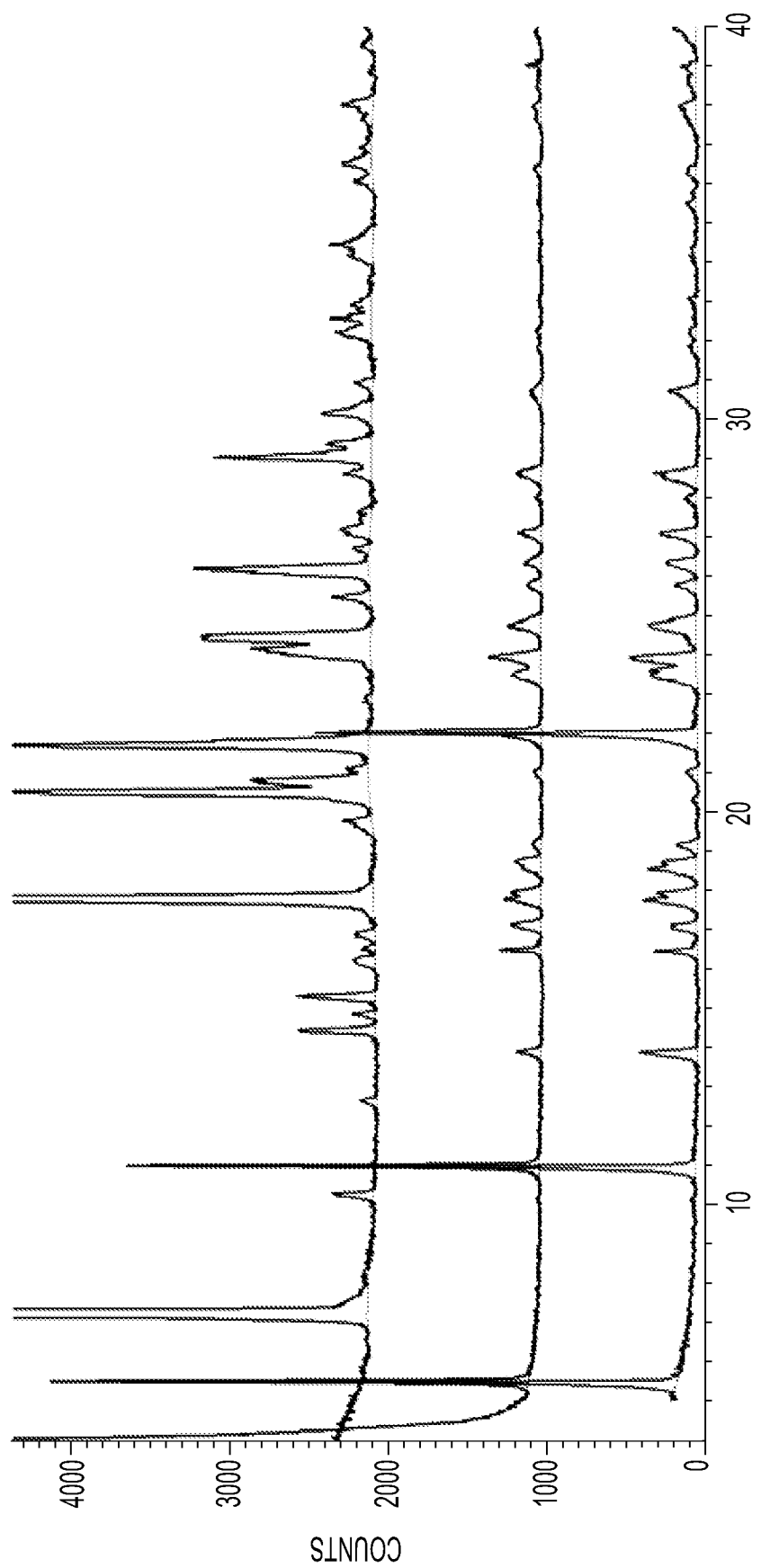
FIG. 31 is an XRPD plot of the material obtained from Example 14. Upper trace: Form A; middle trace: isolated product from Example 14; lower trace: Form B(I).
Figure 32:
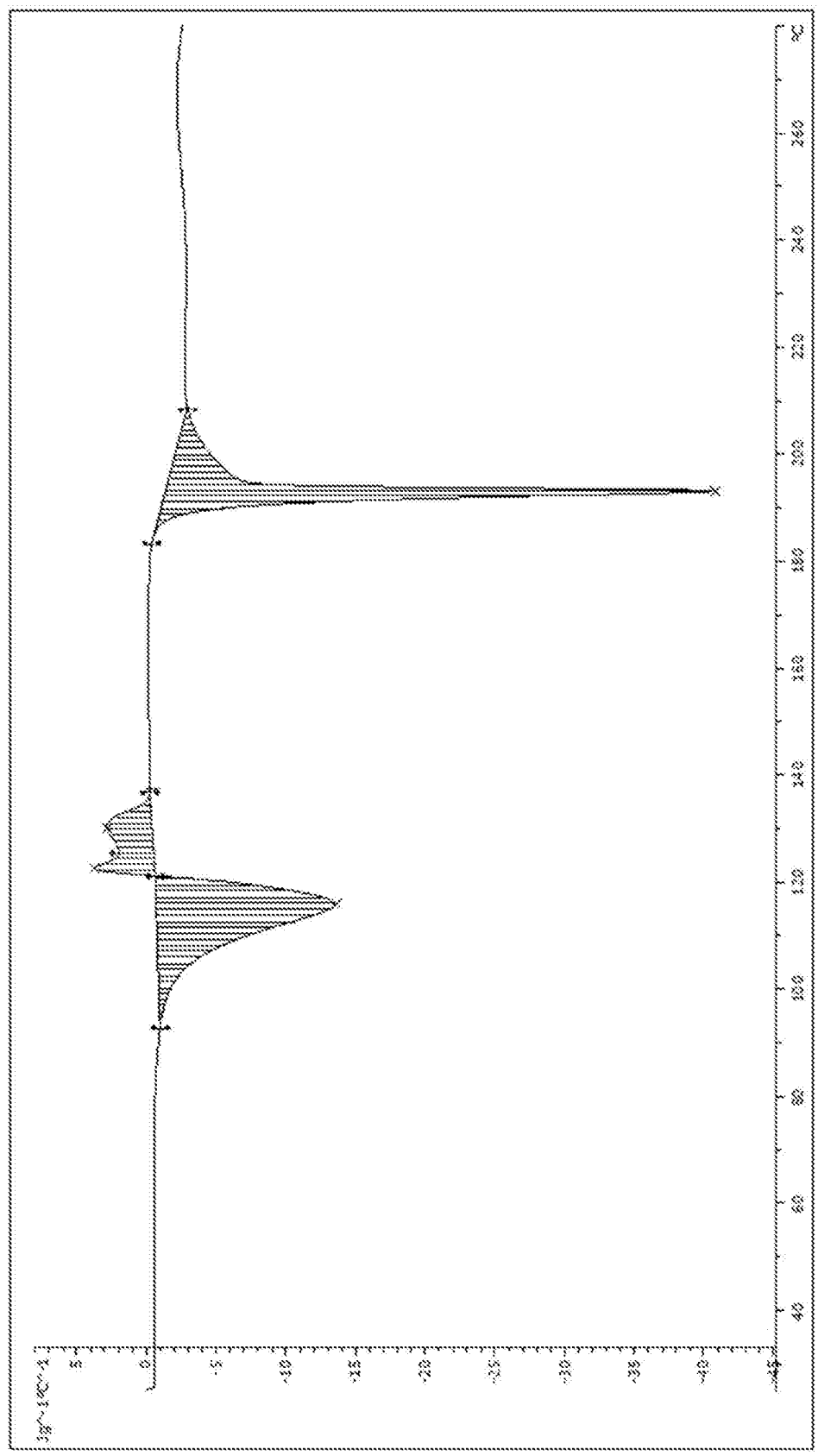
FIG. 32 is a DSC plot over a temperature range 25-280° C. heating at 5° C. per minute for the material obtained from Example 14. Lobe 1: integral −134 J/g, onset 105.21° C., peak 115.92° C., endset 121.05° C.; Lobe 2: integral 13.47 J/g, onset 121.05° C., peak 122.58° C., endset 126.45° C.; Lobe 3: integral 23.1 J/g, onset 127.43° C., peak 130.17° C., endset 134.67° C.; Lobe 4: integral −125.89 J/g, onset 190.72° C., peak 193.08° C., endset 194.16° C.
Figure 33:
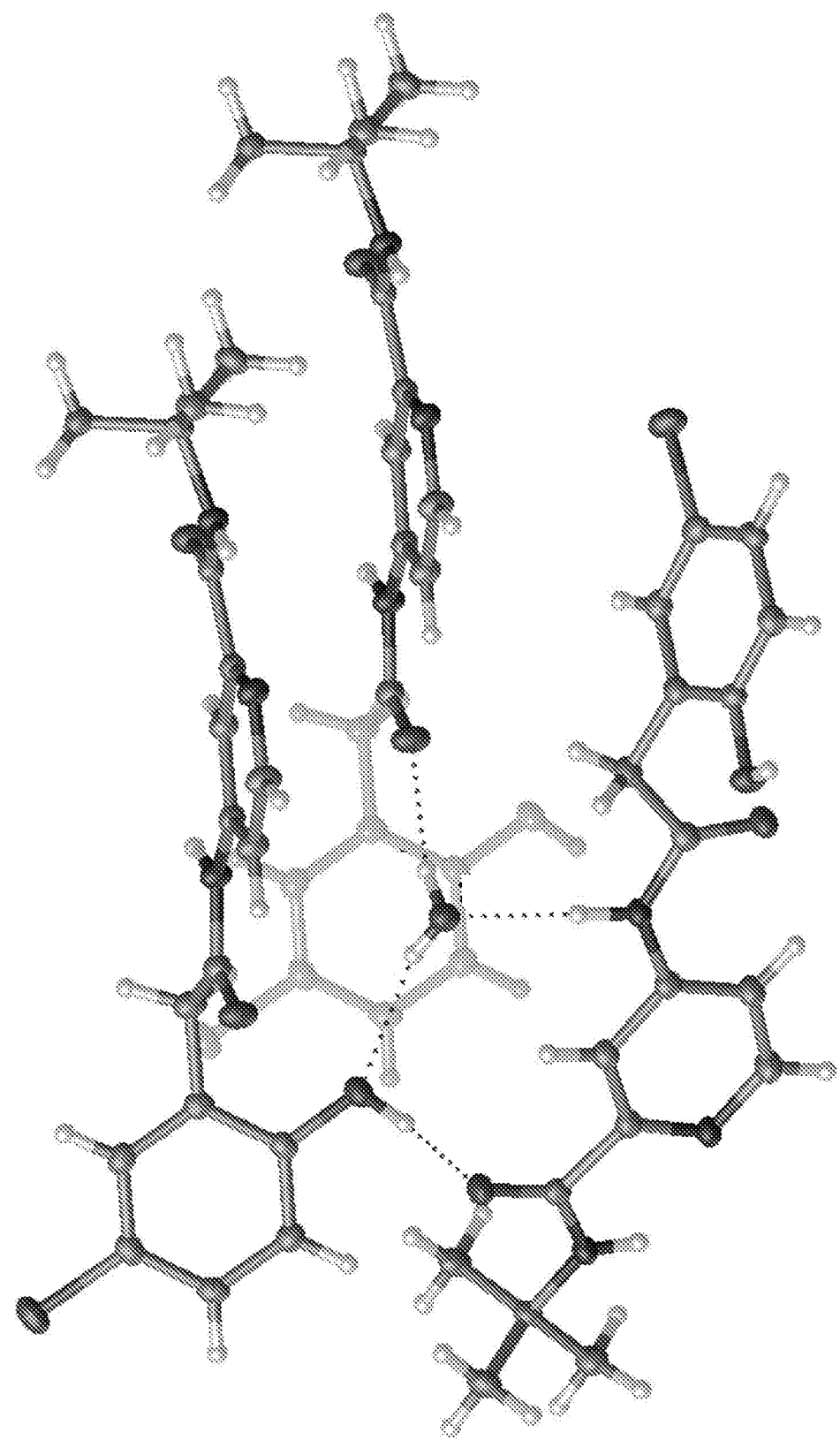
FIG. 33 shows the hydrogen bonding found between water and the molecular structure of Compound 1 in crystals of Form B(I)—thermal ellipsoids are drawn at the 50% probability level.

Compound 1 Form B is a channel hydrate, the micronisation process reduces the size of the crystals and as a result the ability of the crystal to hold water is diminished. The solid generated is isostructural with form B which is confirmed by the XRPD (FIG. 31) and DSC (FIG. 32) analyses. There is no form A detected and there is no amorphous character in the XRPD analysis.

Example 15—Conversion of Form A into Form B(I) in Aqueous Suspension

It had been observed that, when in aqueous suspension, micronised Form A transformed into Form B on standing at low temperature. Since the observed phase transition occurred at sub-ambient temperature, this implies that the process is likely to be exothermic, preceded by adsorption of water molecules onto the surface of Form A. Furthermore, the enthalpy of crystallisation of Form B into Form A is at least partially exothermic, and this is corroborated by DSC analysis of Form B (see FIG. 21a).

It was proposed that the crystallisation of Form A into Form B should be induced by the application of cold (thermodynamic) and once initiated, the turnover rate should be promoted, at least in the short-term by the application of heat (kinetic); contrasting solubility products of the two polymorphs may also be influential. Moreover, the inventor speculated that the rate determining step of Form A into Form B under aqueous conditions is likely to be bimolecular with respect to. water (Form A+water→Form B) rather than proceeding via Form A→Form B (anhydrate)+water→Form B. Therefore, the turnover into Form B should exhibit lower hydration rate kinetics in the presence of $D_2O$, by virtue of the primary kinetic isotope effect (Thomas and Jennings; *Chem. Mater.* 1999, 11, 1907-1914).

Procedure

Four separate samples of micronised Form A (4×100 mg, particle size 0.6 μm<80%<2.5 μm, supported by SEM) were charged to four separate Crystal 16 blank, glass vials and purified water (1 ml, 10.0 vol) was added to three of the four vials and heavy water (1 ml, $D_2O$, NMR solvent, high isotopic purity) was added to the fourth.

One of the vials made up in water underwent thermocycling from 20 to 40° C., and the remaining three underwent thermocycling from –10 to +10° C., over 40 h; one of which was seeded at 10% w/w with Form B (see Table 13).

TABLE 13

Thermocycling Conditions for Form A in Aqueous Suspension

| Experiment | Micronised Form A | Form B seeds | Medium | Thermo-cycle | Form B detected |
|---|---|---|---|---|---|
| A1 | 99.1 mg | None | Purified water | T1 | No |
| B1 | 99.0 mg | None | Purified water | T2 | Yes (est 1.5% w/w) |
| C1 | 100.4 mg | None | Heavy water ($D_2O$) | T2 | No |
| D1 | 90.7 mg | 10.6 mg | Purified water | T2 | Yes (est 4.2% w/w) |

T1: constant amplitude cycle 20 to 40 to 20° C. etc., at a rate of ±0.5° C./minute.
T2: constant amplitude cycle –10 to +10 to –10° C. etc., at a rate of ±0.5° C./minute In Experiment A1, Form B was not detected under aqueous conditions after 40 hours, thermocycle T1.

In Experiment B1, Form B was detected under aqueous conditions and thermocycle T2 after 40 hours, supporting the hypothesis that water adsorption onto the surface of Form A is exothermic, i.e. thermodynamically favoured by cooling and the subsequent crystallisation into Form B is also presumed to be exothermic.

In Experiment C1, Form B was not detected under aqueous conditions ($D_2O$) and thermocycle T2 after 40 hours, supporting the conjecture that water adsorption onto the surface of Form A is likely to be the rate determining step of hydration, constrained under diffusion control and influenced by the different hydrogen-bond strengths of the heavier isotope, implying that the formation of Form B hydrate is bi-molecular and therefore involves two species (i.e. Form A+water) and not uni-molecular (i.e. Form A re-organises into Form B anhydrate and the absorbent instantaneously absorbs a molecule of water to generate Form B) and the rate of hydration will be doubled by doubling the concentration of Form A or increasing the effective accessible surface area of Form A.

In Experiment D1, in which the medium was seeded with form B, as expected Form A converted to Form B more quickly than in Experiment B1.

The following conclusions could be drawn from this experiment:

lower temperature favours the conversion of Form A into Form B;

the order of hydration is bi-molecular; therefore, higher concentration of Form A should favour the conversion of Form A into Form B;

as implied above, a greater surface area of Form A should favour the conversion into Form B;

since hydrated forms are usually less soluble in aqueous media than their anhydrous counterparts, intrinsic solubility products may exert a forward effect on the equilibrium, i.e. promote Form A solute to crystallise out of solution as Form B.

Example 16—Suspension Equilibration of Form B in Anhydrous Acetonitrile

One portion of Form B(II) (1.01 g) was charged with anhydrous acetonitrile (15 vol, 15 ml).

Figure 27:
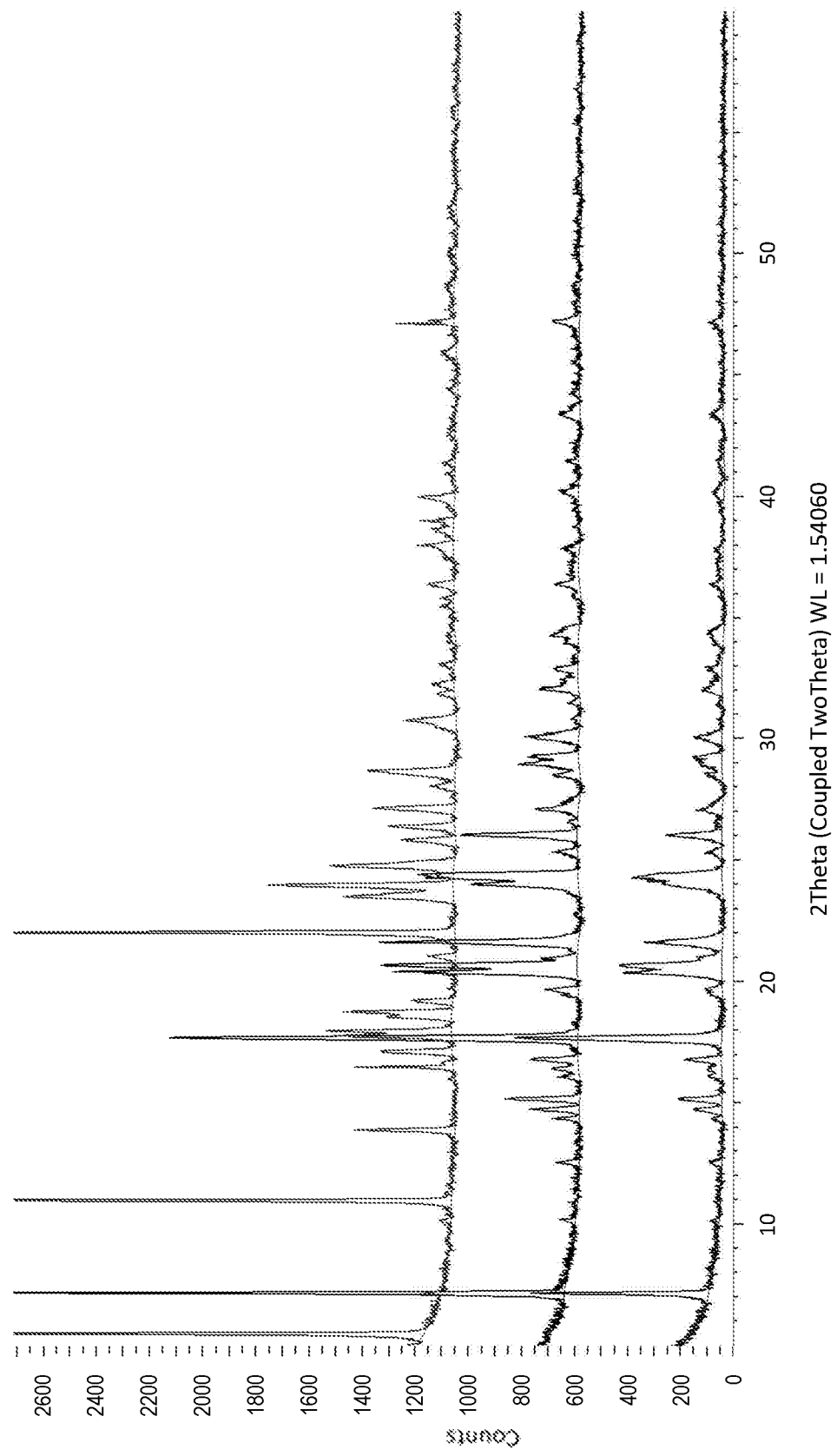
FIG. 27 is an XRPD plot of Form B(II) after suspension equilibration in anhydrous acetonitrile for 3 hours showing that the sample has converted to Form A. Upper trace: input material; middle trace: output material; lower trace: authentic Form A as reference.

This was stirred at room temperature with a flow of nitrogen. The mixture IPC was subsampled at t=3 h and t=23 h. The subsampled mixtures were centrifuged down (13400 rpm for 15 min), supernatants were removed and dried overnight in oven at 40° C. under reduced pressure. The remaining solid was dried (t=2 days) in oven overnight under reduced pressure at 40° C. overnight. The dried white solid (0.54 g, 54% yield not corr.) was analysed by XRPD and DSC. The XRPD plot for the t=3 h subsample is shown in FIG. 27. It can be seen that in anhydrous conditions, Form B(II) is rapidly converted to Form A. The DSC plot was consistent with this finding. The XRPD and DSC plots after 23 hours and 3 days were substantially the same as the 3 hour plot shown in FIG. 27.

A similar procedure was carried out for a portion of Form B(I) (1.06 g). Int his case, the mixture was subsampled at t=5 h and isolation was carried out at t=5 days. The uncorrected yield was 66%.

As with Form B(II), Form B(I) was also rapidly converted to Form A under these conditions.

Figure 28:
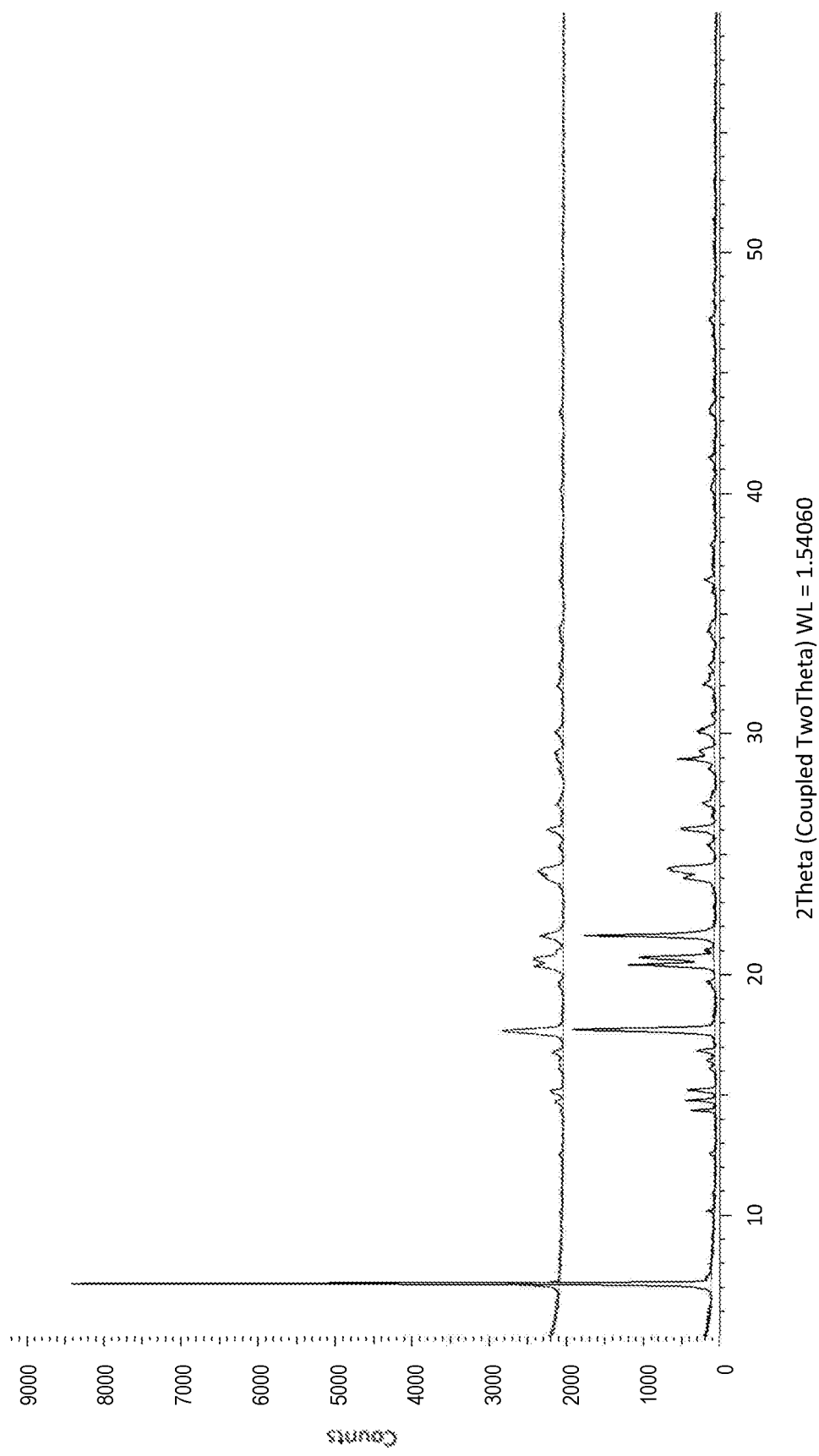
FIG. 28 is an XRPD plot of Form B(I) after suspension equilibration in anhydrous acetonitrile for 5 hours showing that the sample has converted to Form A. Upper trace: authentic Form A (reference); lower trace: Form B(I) after 5 hours suspended in anhydrous acetonitrile.

This can be seen from FIG. 28, which is a XRPD plot for the subsample taken at t=5 hours. The DSC plot was consistent with this result and the XRPD and DSC plots after 5 days were similar.

This experiment confirms that, under anhydrous conditions, Form A is the thermodynamically stable form of Compound 1.

Example 17—Further Thermocycling of Form B(I)

Form B(I) was prepared in the relevant formulation under sterile conditions. The samples were thermocycled for approximately 202 complete cycles. Off-line analyses of the suspensions were performed by polarised light microscopy and end point sampling was performed on the isolated solid pellets of the suspensions after centrifugation. The thermocycling incorporated a wide temperature range (−10° C. to +40° C.). A parallel study was performed using micronised Form A as control.

The experiments conducted are shown in Table 14. In all cases, the suspension volume was 2 ml and thermocycling was carried out over a temperature range −10° C. to +40° C. at a rate of change of 1° C./min for a duration of 336 hours (14 days) and 2020 cycles.

In the table below, the surfactants TWEEN® 80, TWEEN® 20 and SPAN®20 are as set out in Example 8.

TABLE 14

Thermocycling of Form B(I) in Buffered Aqueous Suspensions (Form A Control)

| Experiment | Suspension Type | Suspension strength (mg/ml) |
| --- | --- | --- |
| A Form B(I) | Citrate buffered Tween ® 80 | 15 |
| B Form B(I) | Citrate buffered Tween ® 20/Span ® 20 | 15 |
| C Form B(I) | Citrate buffered Tween ® 80 | 0.5 |
| D Form B(I) | Citrate buffered Tween ® 20/Span ® 20 | 0.5 |
| E Form A | Citrate buffered Tween ® 80 | 15 |
| F Form A | Citrate buffered Tween ® 20/Span ® 20 | 15 |

At daily intervals, a droplet from each thermocycle suspension was withdrawn, placed on a microscope slide and photographed. After 14 days constant thermocycling, the suspensions were filtered, isolable solids were oven dried and analysed for evidence of form change and change in chemical purity.

Figure 21A:
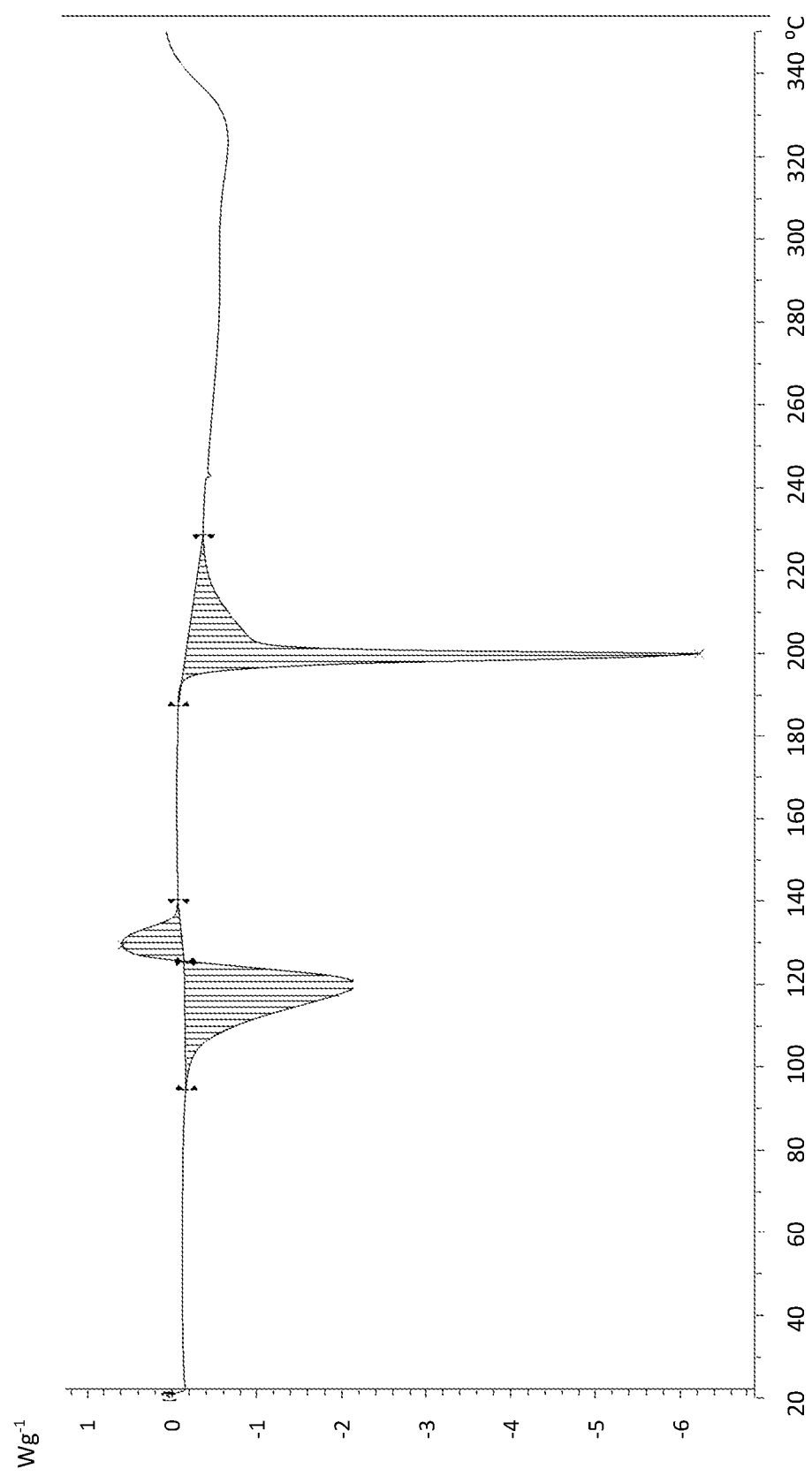
FIG. 21a is a DSC plot of Form B(I), temperature range 20-350° C.; heating at 10° C. per minute; Lobe 1: integral −23.23 W° Cg$^{-1}$, onset 107.16° C., peak 119.83° C., endset 125.41° C.; Lobe 2: integral 5.21 W° Cg$^{-1}$, onset 125.42° C., peak 129.50° C., endset 136.09° C.; Lobe 3: integral −26.07 W° Cg$^{-1}$, onset 196.66° C., peak 199.83° C., endset 201.37° C.
Figure 21B:
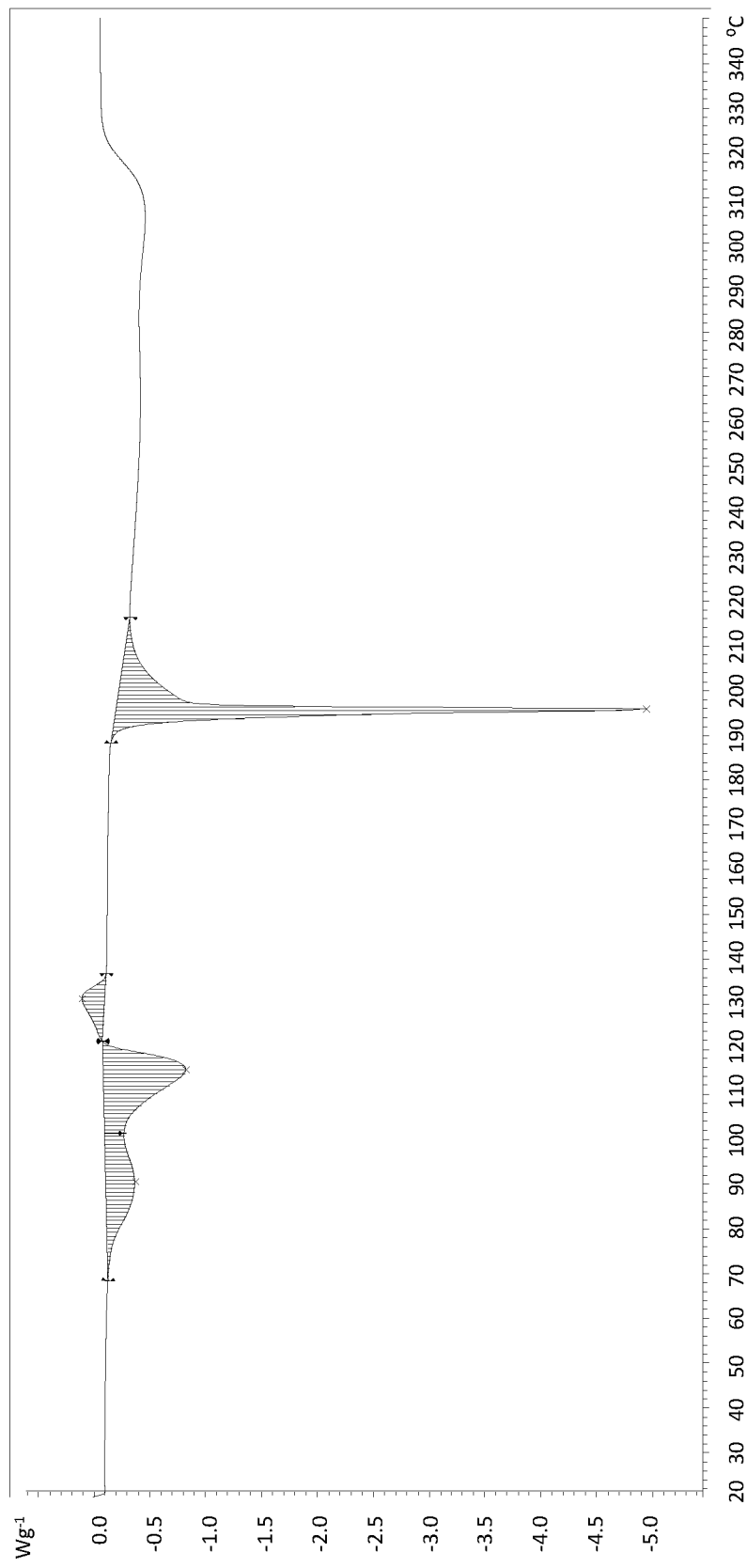
FIG. 21b is a DSC plot of Form B(II), temperature range 20-350° C.; heating at 10° C. per minute; Lobe 1: integral −4.90 W° Cg$^{-1}$, onset 75.22° C., peak 90.50° C., endset 111.38° C.; Lobe 2: integral −8.37 W° Cg$^{-1}$, onset 102.87° C., peak 115.50° C., endset 120.74° C.; Lobe 3: integral 1.59 W° Cg$^{-1}$, onset 121.83° C., peak 131.42° C., endset 135.55° C.; Lobe 4: integral −13.35 W° Cg$^{-1}$, onset 194.06° C., peak 195.92° C., endset 196.70° C.
Figure 22A:
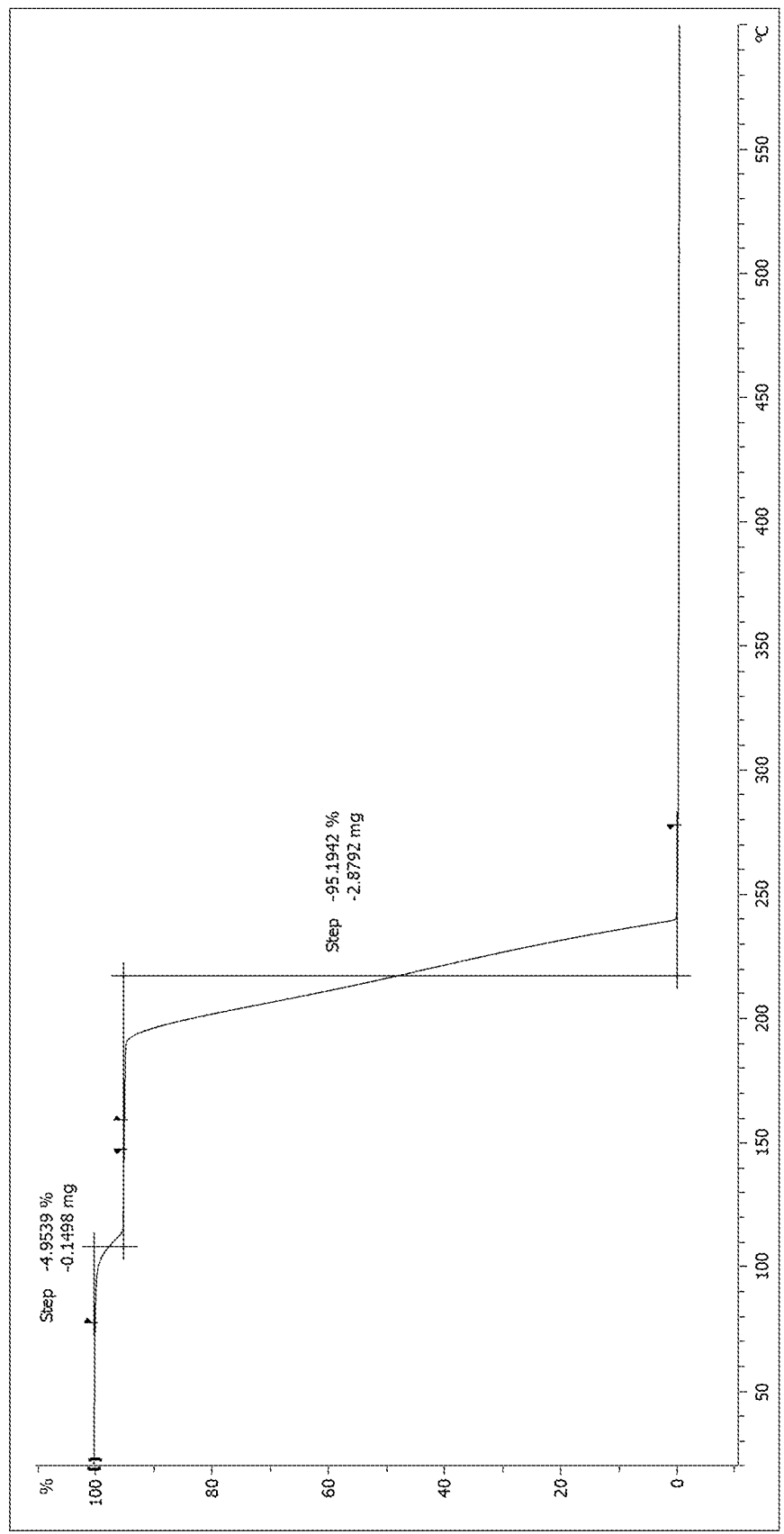
FIG. 22a shows a TGA plot for Form B(I) obtained using heating from 20-600° C. at a rate of 5° C. per minute; Step 1: −4.9539%, −0.1498 mg; Step 2: −95.1942%, −2.8792 mg.
Figure 22B:
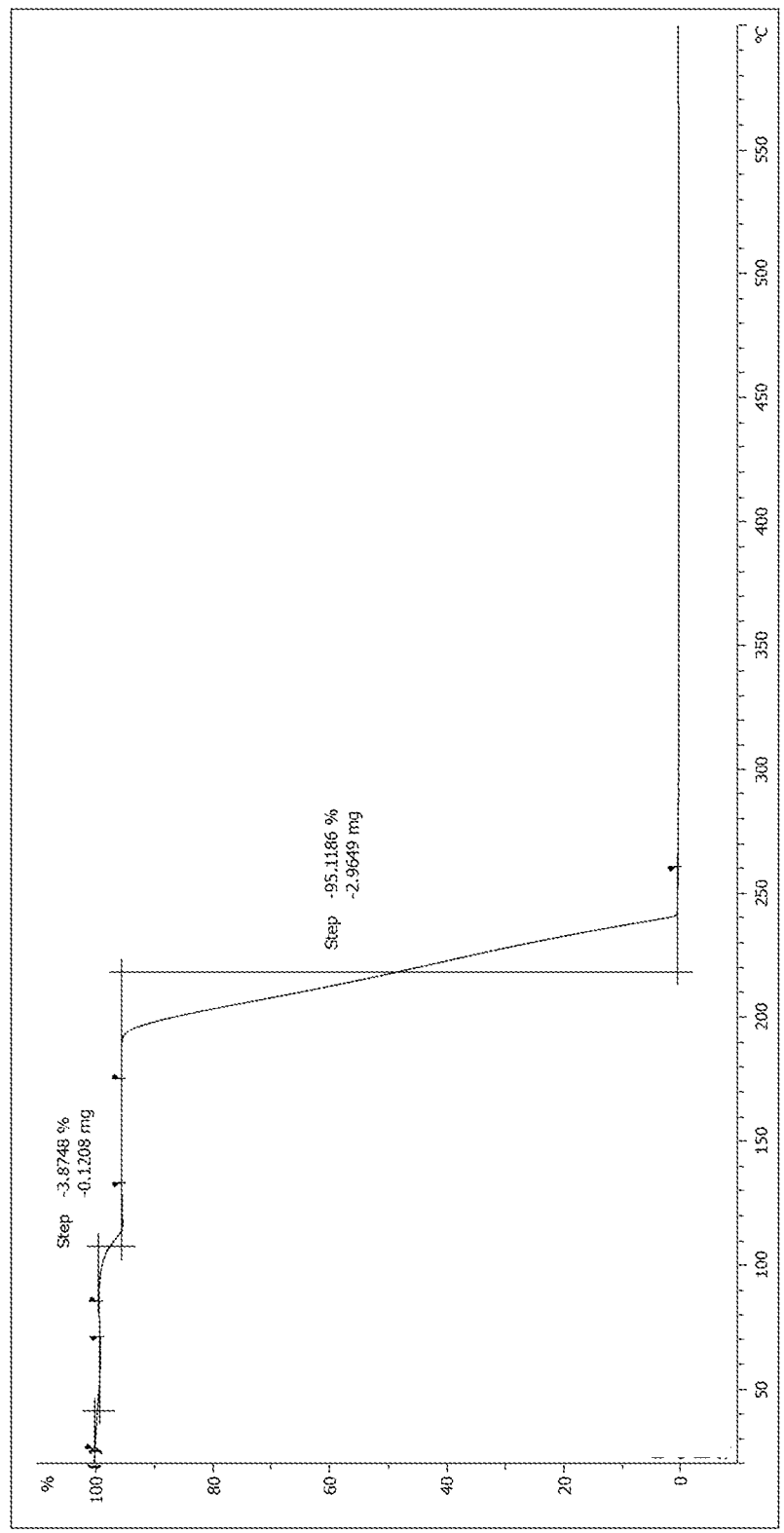
FIG. 22b shows a TGA plot for Form B(II) obtained using heating from 20-600° C. at a rate of 5° C. per minute; Step 1: −0.8685%, −0.02707 mg; Step 2 −3.8748%, −0.1208 mg; Step 3: −95.1186%, −2.9649 mg.
Figure 23A:
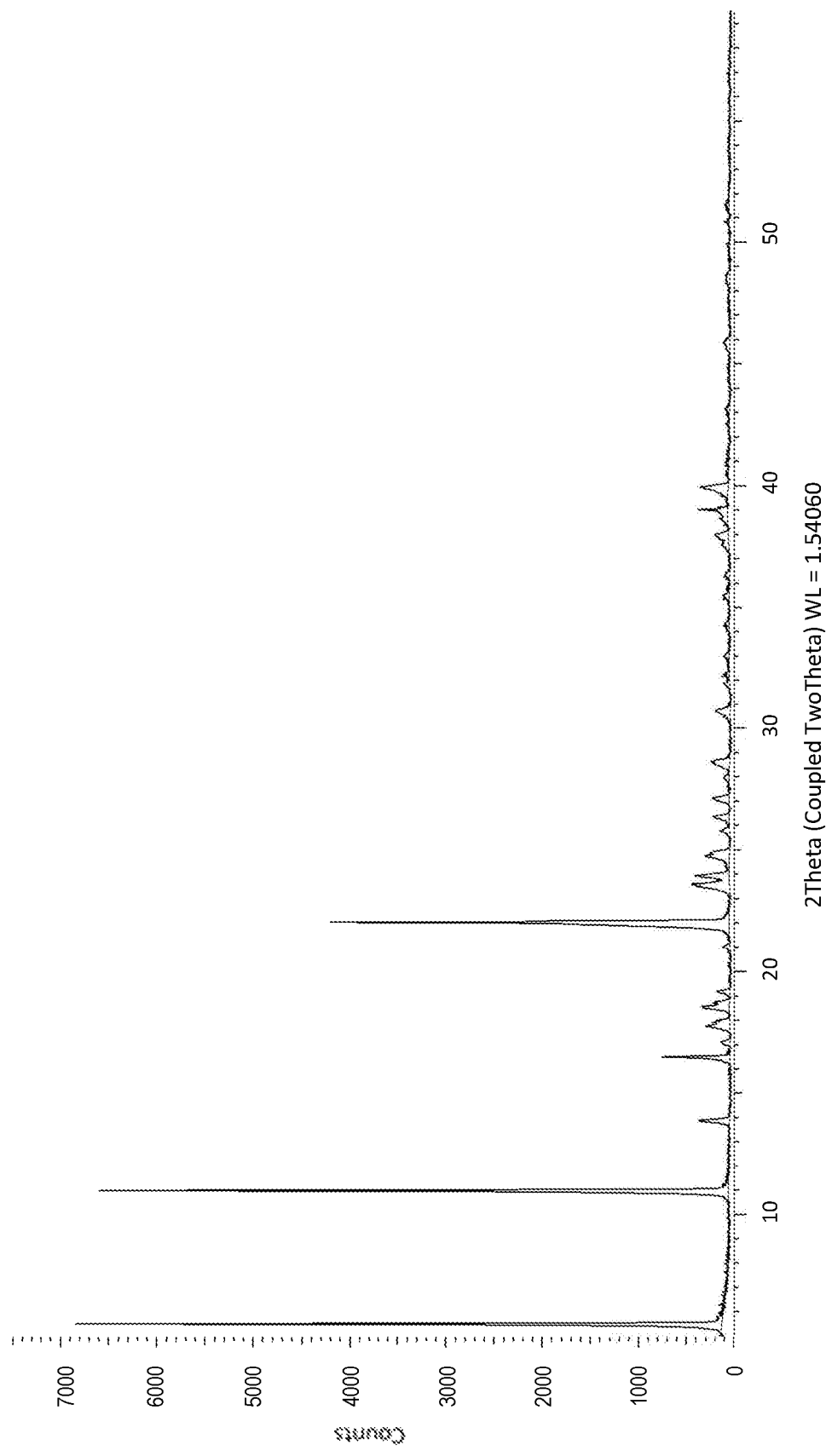
FIG. 23a is an XRPD plot for Form B(I).
Figure 23B:
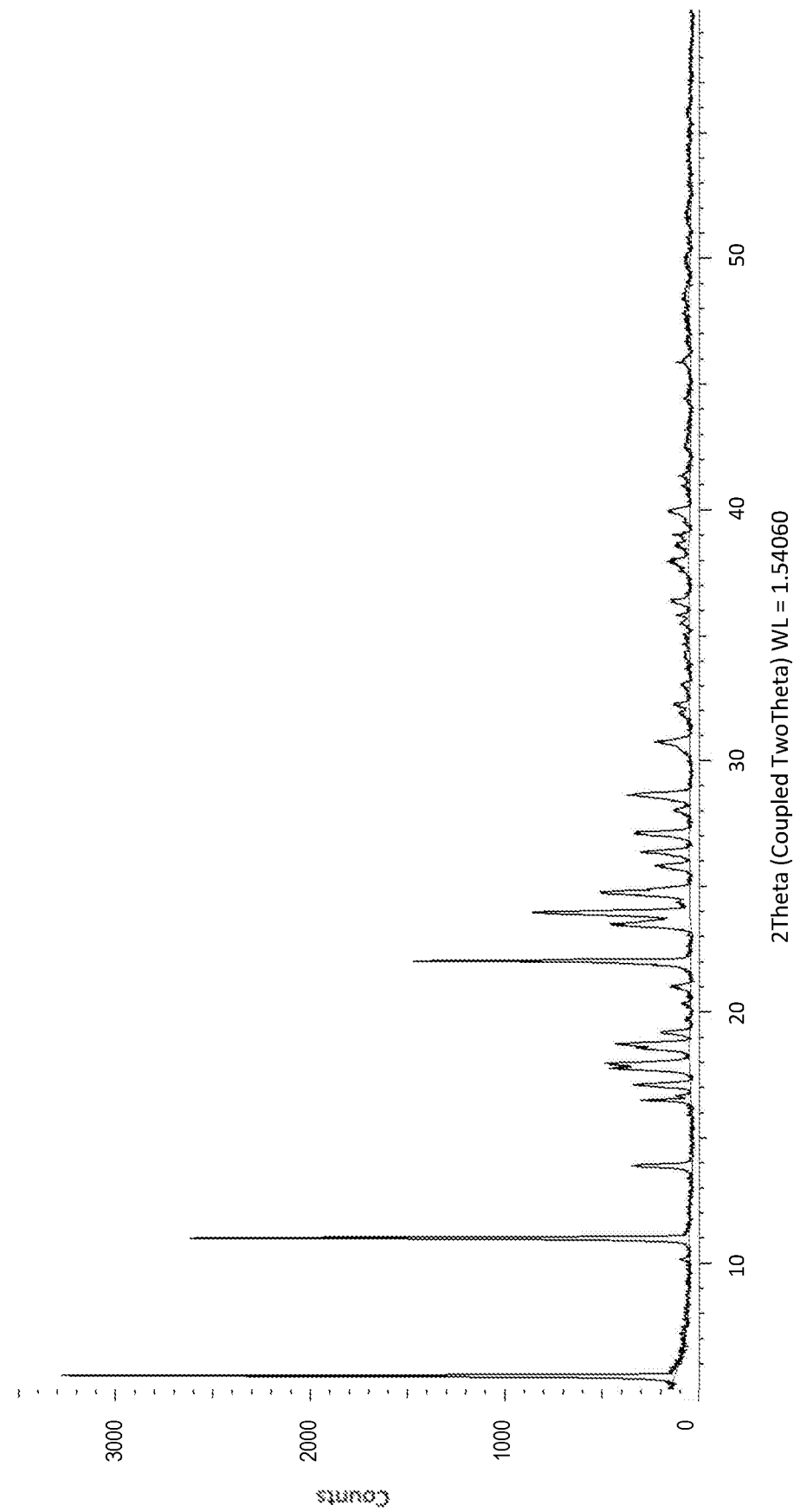
FIG. 23b is an XRPD plot for Form B(II).
Figure 29:
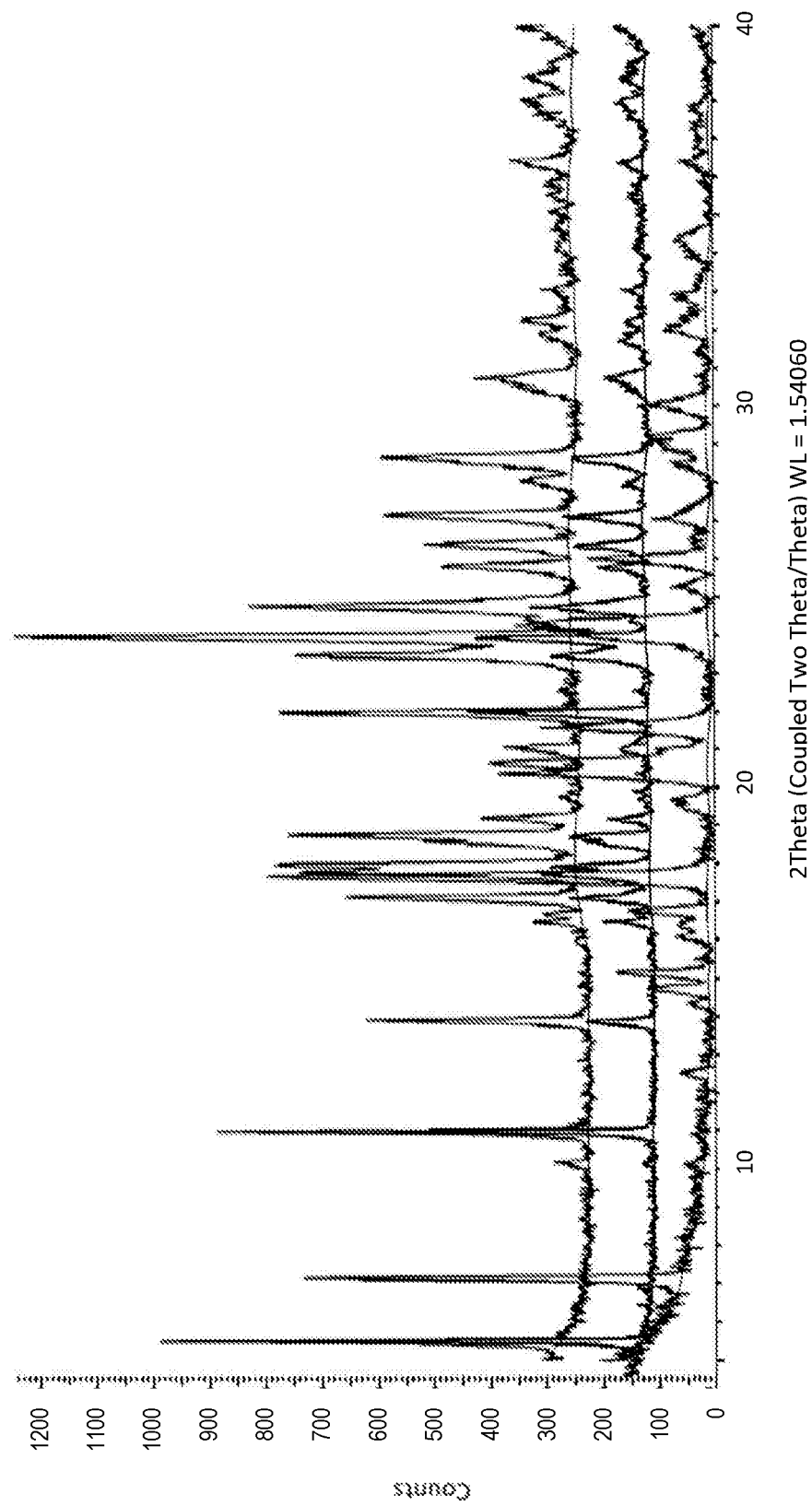
FIG. 29 is an XRPD plot of Form A suspended in citrate buffered Tween® 80 after 14 days of thermocycling at −10° C. to +40° C. at a rate of change of 1° C./min (middle trace) compared with XRPDs of authentic Form A (lower trace) and authentic Form B(I) (upper trace); and shows that the sample has converted to Form B.
Figure 30:
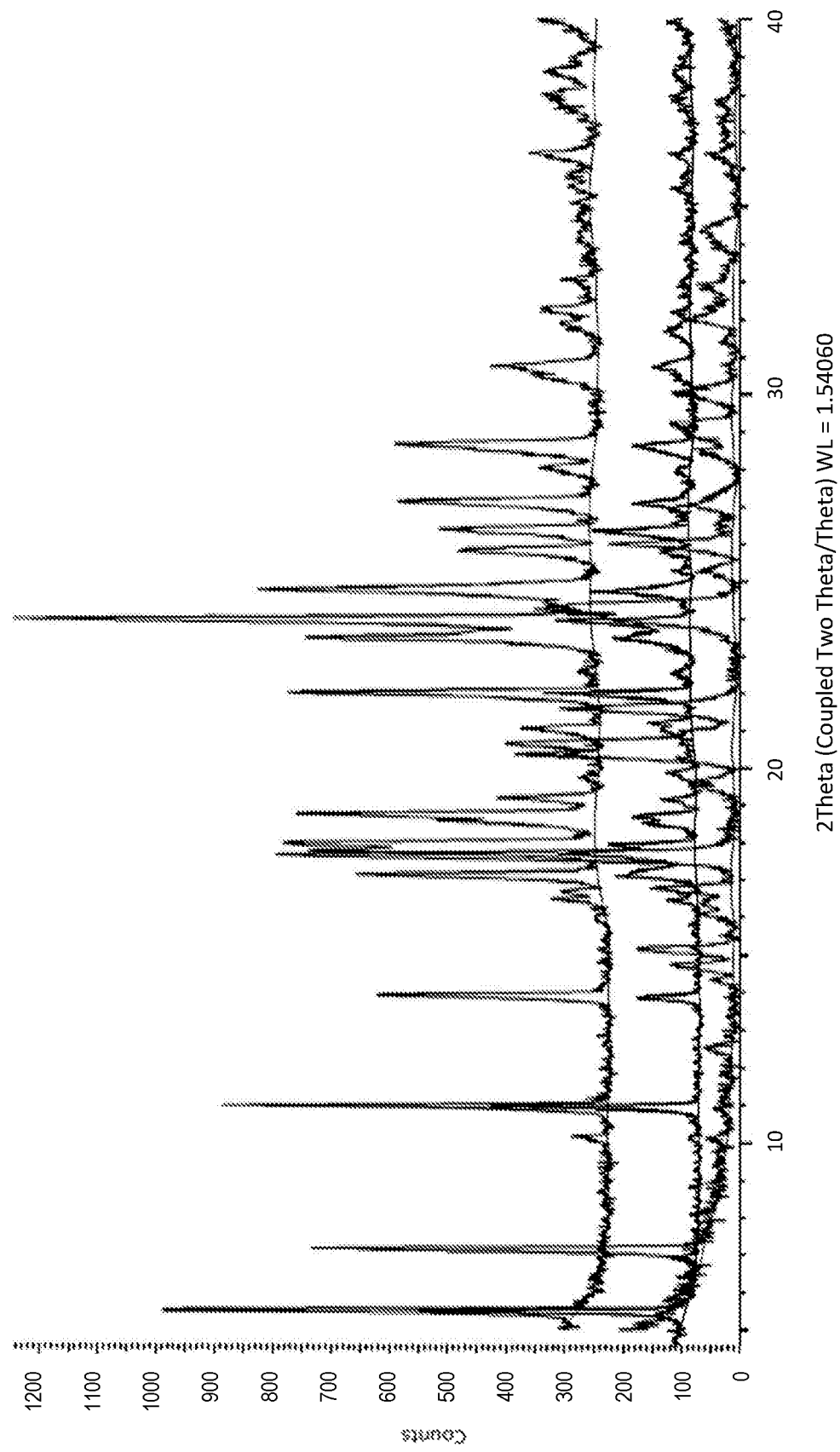
FIG. 30 is an XRPD plot Form A suspended in citrate buffered Tween® 20/Span® 22 after 14 days of thermocycling at −10° C. to +40° C. at a rate of change of 1° C./min (middle trace) compared with XRPDs of authentic Form A (lower trace) and authentic Form B(I) (upper trace)); and shows that the sample has converted to Form B.

Form B(I) was stable to the constant thermocycling treatment over 14 days as shown by the XRPD, DSC and TGA plots, which were identical to those of FIGS. 23a, 21a and 22a and no changes were detected by polarised light microscopy. Form A suspensions began to show morphological change at the eight day time point (observed by polarised light microscopy) and had completely changed at the 14 day time point. Analyses of the isolated material confirmed that Form A had changed into Form B(I). The XRPD spectra of the materials from Experiments E (form A in citrate buffered Tween® 80) and F (Form A in citrate buffered Tween® 20/Span® 20) after 14 days of thermocycling are shown in FIGS. 29 and 30 and confirms that only Form B was present. Similarly, the DSC and TGA plots confirmed the substantially complete transformation of the material into Form B(I). No reduction in chemical purity accompanied the form change.

Example 18—Characterisation of Single Crystal of Form B(I)

A small sample of Compound 1, Form B(I) was suspended in perfluoroether oil; a colourless plate-shaped crystal of size 0.110×0.040×0.022 mm$^3$ was selected and mounted on a MiTeGen™ holder with perfluoroether oil then aligned upon a Rigaku AFC11 007-HF™ diffractometer, equipped with VariMax™ confocal mirrors and an AFC11 goniometer and HyPix 6000™ detector. The crystal was kept at a steady T=100(2) K during data collection. The structure was solved with the ShelXT™ (Sheldrick, 2015) structure solution program using the Intrinsic Phasing solution method and by using Olex2™ (Dolomanov et al., 2009) as the graphical interface. The model was refined with version 2018/3 of ShelXT™ (Sheldrick, 2015) using Least Squares minimisation.

The crystal data was as follows:

$C_{18}H_{22}ClN_3O_4$, $M_r$=379.83, orthorhombic, $Pna2_1$ (No. 33), a=32.1319(3) Å, b=5.56259(5) Å, c=10.24568(9) Å, $\alpha=\beta=\gamma=90°$, V=1831.28(3) Å$^3$, T=100(2) K, Z=4, Z'=1, $\mu(CuK_\alpha)$=2.099 mm$^{-1}$, 30062 reflections measured, 3324 unique ($R_{int}$=0.0389) which were used in all calculations. The final $wR_2$ was 0.0635 (all data) and $R_1$ was 0.0238 (I>2(I)).

The invention claimed is:

1. A compound which is N-tert-Butyl-4-[[2-(5-chloro-2-hydroxy-phenyl)acetyl]amino]pyridine-2-carboxamide (Compound 1) having the following structural formula:

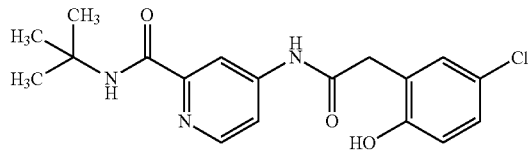 [SMILES: CC(C)(C)NC(=O)c1cc(NC(=O)Cc2cc(Cl)ccc2O)ccn1]

in the form of its Form A anhydrous solid crystalline polymorph which has an XRPD diffractogram as shown in FIG. 1; or in the form of its Form B hydrate solid crystalline polymorph has an XRPD diffractogram substantially as shown in FIG. 4.

2. A compound according to claim 1, wherein Compound 1 in the form of its Form A crystalline polymorph has an XRPD diffractogram with characteristics peaks expressed in values of degrees 2-theta at a major peak at 7.25±0.2 and at least three characteristic peaks at positions 14.44±0.2, 20.42±0.2, 21.68±0.2, 24.38±0.2, 27.21±0.2, 29.01±0.2, 30.82±0.2, 36.46±0.2 and 41.49±0.2.

3. A compound according to claim 2 characterised by an XRPD diffractogram further comprising a major characteristic peak expressed in values of degrees 2-theta at 7.25±0.2 and at least three characteristic peaks at positions 10.20±0.2, 14.44±0.2, 17.79±0.2, 20.42±0.2, 20.69±0.2, 21.68±0.2, 24.22±0.2, 24.38±0.2, 26.13±0.2, 27.21±0.2, 29.01±0.2, 30.82±0.2, 36.46 and 41.49±0.2.

4. A compound according to claim 2 characterised by an XRPD diffractogram further comprising a major characteristic peak expressed in values of degrees 2-theta at 7.25±0.2 and at least three characteristic peaks at positions 10.20±0.2, 14.44±0.2, 16.13±0.2, 17.79±0.2, 20.42±0.2, 20.69±0.2, 21.07±0.2, 21.68±0.2, 24.09±0.2, 24.22±0.2, 24.38±0.2, 26.13±0.2, 27.21±0.2, 29.01±0.2, 29.30±0.2, 30.82±0.2, 32.50±0.2, 36.46±0.2 and 41.49±0.2 degrees.

5. A compound according to claim 2, wherein the XRPD diffractogram further comprises characteristic peaks expressed in values of degrees 2-theta at positions 21.68±0.2 and 29.01±0.2 and a cluster of characteristic peaks at 24.09±0.2, 24.22±0.2 and 24.3801±0.2.

6. A compound according to claim 2, wherein Form A polymorph is substantially free of other forms of Compound 1 such that at least 97% by weight of Compound 1 is present as the Form A polymorph.

7. A compound according to claim 2 which is micronised.

8. A process for the preparation of a compound according to claim 2 comprising crystallising Compound 1 from a solvent selected from acetone, butanol, ethanol, ethyl formate, isopropyl acetate, methyl acetate, nitromethane, 2-propanol, propionitrile and acetonitrile.

9. A process according to claim 8, wherein the process comprises the steps of:
i. preparing a saturated solution of Compound 1 in a solvent at a temperature of about 50 to 70° C.;
ii. cooling the solution to a temperature of about 5 to 20° C.;
iii. allowing the cooled solution to stand until crystals of Compound 1 form; and
iv. isolating the crystallised product;
wherein the solvent is selected from acetone, butanol, ethanol, ethyl formate, isopropyl acetate, methyl acetate, nitromethane, 2-propanol, propionitrile and acetonitrile.

10. A process according to claim 8, wherein the solvent is selected from acetonitrile, ethanol, ethyl acetate, methyl acetate, butanol, 2-propanol or isopropyl acetate.

11. A compound according to claim 1, wherein Compound 1 in the form of its Form B hydrate solid crystalline polymorph has an XRPD diffractogram with characteristics peaks expressed in values of degrees 2-theta at a major peak at position 11.03±0.2 and at least three characteristic peaks at positions 5.56±0.2, 14.04±0.2, 17.28±0.2, 18.03±0.2, 18.86±0.2, 22.08±0.2, 23.69±0.2, 24.12±0.2 and 24.93±0.2.

12. A compound according to claim 11 characterised by an XRPD diffractogram further comprising a major characteristic peak expressed in values of degrees 2-theta at position 11.03±0.2 and at least three characteristic peaks at positions 5.56±0.2, 14.04±0.2, 17.28±0.2, 18.03±0.2, 18.86±0.2, 19.34±0.2, 22.08±0.2, 23.69±0.2, 24.12±0.2, 24.93±0.2, 25.98±0.2, 26.53±0.2, 27.28±0.2 and 28.79±0.2.

13. A compound according to claim 11 which has an XRPD diffractogram further comprising characteristic peaks expressed in values of degrees 2-theta at positions 5.36±0.2 and 22.08±0.2.

14. A compound according to claim 11, which is micronised.

15. A compound according to claim 11, wherein Form B polymorph is substantially free of other forms of Compound 1 such that at least 97% by weight of Compound 1 is present as the Form B polymorph.

16. A compound according to claim 11, wherein Form B polymorph is the Form B(I) pseudopolymorph and is characterised in that it undergoes unimodal dehydration.

17. A process for the preparation of a compound according to claim 11, comprising crystallising Compound 1 from an aqueous solvent such as water or water mixed with acetonitrile.

18. A process according to claim 17 comprising the steps of:
i. preparing a saturated solution of Compound 1 in a solvent at a temperature of about 60 to 80° C.;
ii. cooling the solution to a temperature of about 5 to 20° C.;
iii allowing the cooled solution to stand until crystals of Compound 1 form; and
iv. isolating the crystallised product;
wherein the solvent is an aqueous solvent such as water or water mixed with acetonitrile, for example acetonitrile/water in a ratio of from 5:1 to 1:5 v/v.

* * * * *